United States Patent
Takada et al.

(10) Patent No.: US 10,591,471 B2
(45) Date of Patent: Mar. 17, 2020

(54) SUPPRESSION OF SPLA2-INTEGRIN BINDING FOR TREATING AN INFLAMMATORY CONDITION OR SUPPRESSING CELL PROLIFERATION

(71) Applicant: THE REGENTS OF THE UNIVERSITY OF CALIFORNIA, Oakland, CA (US)

(72) Inventors: Yoshikazu Takada, Davis, CA (US); Yoko Takada, Davis, CA (US); Masaaki Fujita, Osaka (JP)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/526,573

(22) PCT Filed: Nov. 12, 2015

(86) PCT No.: PCT/US2015/060370
§ 371 (c)(1),
(2) Date: May 12, 2017

(87) PCT Pub. No.: WO2016/077579
PCT Pub. Date: May 19, 2016

(65) Prior Publication Data
US 2018/0238866 A1 Aug. 23, 2018

(51) Int. Cl.
| | |
|---|---|
| *C07K 4/00* | (2006.01) |
| *A61K 38/04* | (2006.01) |
| *A61K 39/00* | (2006.01) |
| *G01N 33/53* | (2006.01) |
| *G01N 33/543* | (2006.01) |
| *C07K 14/705* | (2006.01) |
| *A61K 38/00* | (2006.01) |
| *A61K 38/17* | (2006.01) |
| *G01N 33/52* | (2006.01) |
| *G01N 33/533* | (2006.01) |
| *G01N 33/566* | (2006.01) |
| *G01N 33/58* | (2006.01) |

(52) U.S. Cl.
CPC ....... *G01N 33/54306* (2013.01); *A61K 38/00* (2013.01); *A61K 38/177* (2013.01); *C07K 14/70546* (2013.01); *G01N 33/52* (2013.01); *G01N 33/533* (2013.01); *G01N 33/5306* (2013.01); *G01N 33/566* (2013.01); *G01N 33/582* (2013.01); *G01N 2333/70546* (2013.01); *G01N 2333/92* (2013.01); *G01N 2500/02* (2013.01)

(58) Field of Classification Search
None
See application file for complete search history.

(56) References Cited

U.S. PATENT DOCUMENTS

| | | | |
|---|---|---|---|
| 8,168,586 B1 * | 5/2012 | Fang | C12Q 1/6886 514/1.2 |
| 2009/0092595 A1 | 4/2009 | Takada et al. | |
| 2013/0078253 A1 | 3/2013 | Fang et al. | |

FOREIGN PATENT DOCUMENTS

WO   WO-2004045542 A2 *   6/2004   ........... A61K 38/178

OTHER PUBLICATIONS

Ye et al. Identification of inhibitors against interaction between pro-inflammatory sPLA2-IIA protein and integrin αvβ3. Bioorganic & Medicinal Chemistry Letters 23 (2013) 340-345. (Year: 2013).*
Saegusa et al. Pro-inflammatory Secretory Phospholipase A2 Type IIA Binds to Integrins αvβ3 and α4β1 and Induces Proliferation of Monocytic Cells in an Integrin-dependent Manner. The Journal of Biological Chemistry vol. 283, No. 38, pp. 26107-26115, Sep. 19, 2008 (Year: 2008).*
Dickerson, Tiffany Jeanette., Inhibition of Pro-inflammatory secretory Phospholipase A-IIA Binding to Integrins (alphavbeta3). Masters Abstracts International, (2011) vol. 49, No. 6, p. 3784, pp. 1-71 (Year: 2011).*

* cited by examiner

*Primary Examiner* — Maher M Haddad
(74) *Attorney, Agent, or Firm* — Kilpatrick Townsend & Stockton LLP

(57) ABSTRACT

The present invention relates to the discovery that a secretory phospholipase A2 (sPLA2-IIA) plays an active role in mediating cellular signaling leading to an inflammatory response or cell proliferation by way of its specific binding with integrin β at site 2 of integrin β. More specifically, the invention provides a method for identifying inhibitors of inflammatory or proliferative signaling by screening for compounds that interrupt the specific binding of sPLA2 and integrin β at site 2. The invention also provides the novel use of a substance that suppresses the specific binding between sPLA2 and site 2 of integrinβ for the purpose of treating or preventing a condition involving an undesired inflammatory response or cell proliferation.

13 Claims, 21 Drawing Sheets
Specification includes a Sequence Listing.

a  Adhesion of α4-K562 cells to sPLA2-IIA b  U937

SEQUENCE LISTING

```
<160> NUMBER OF SEQ ID NOS: 28

<210> SEQ ID NO 1
<211> LENGTH: 20
<212> TYPE: PRT
<213> ORGANISM: Artificial Sequence
<220> FEATURE:
<223> OTHER INFORMATION: Description of Artificial Sequence: Synthetic
      integrin beta fragment peptide

<400> SEQUENCE: 1

Leu Pro Asn Asp Gly Gln Cys His Leu Glu Asn Asn Met Tyr Thr Met
1               5                   10                  15

Ser His Tyr Tyr
            20
```

```
<210> SEQ ID NO 2
<211> LENGTH: 20
<212> TYPE: PRT
<213> ORGANISM: Artificial Sequence
<220> FEATURE:
<223> OTHER INFORMATION: Description of Artificial Sequence: Synthetic
      integrin beta fragment peptide

<400> SEQUENCE: 2

Thr Pro Asn Asp Gly Arg Cys His Leu Glu Asp Asn Leu Tyr Lys Arg
1               5                   10                  15

Ser Asn Glu Phe
            20

<210> SEQ ID NO 3
<211> LENGTH: 21
<212> TYPE: PRT
<213> ORGANISM: Artificial Sequence
<220> FEATURE:
<223> OTHER INFORMATION: Description of Artificial Sequence: Synthetic
      integrin beta fragment peptide

<400> SEQUENCE: 3

Gln Pro Asn Asp Gly Gln Cys His Val Gly Ser Asp Asn His Tyr Ser
1               5                   10                  15

Ala Ser Thr Thr Met
            20

<210> SEQ ID NO 4
<211> LENGTH: 21
<212> TYPE: PRT
<213> ORGANISM: Artificial Sequence
<220> FEATURE:
<223> OTHER INFORMATION: Description of Artificial Sequence: Synthetic
      integrin beta fragment peptide

<400> SEQUENCE: 4

Ser Arg Asn Asp Glu Arg Cys His Leu Asp Thr Thr Gly Thr Tyr Thr
1               5                   10                  15

Gln Tyr Arg Thr Gln
            20

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Leu Asn Asp Ile Phe Glu Ala Gln Lys Ile Glu Trp His Glu
1               5                   10                  15

<210> SEQ ID NO 6
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 6

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Glu Glu Glu Glu Glu Glu
1               5

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Ala Pro Val Pro Tyr Pro Asp Pro Leu Glu Pro Arg
1               5                   10

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asp Tyr Lys Asp Asp Asp Asp Lys
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Tyr Pro Tyr Asp Val Pro Asp Tyr Ala
1               5

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      His tag
<220> FEATURE:
<221> NAME/KEY: MISC_FEATURE
<222> LOCATION: (6)..(10)
<223> OTHER INFORMATION: May or may not be present
```

```
<400> SEQUENCE: 11

His His His His His His His His His His
1               5                   10

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 12

His His His His His His
1               5

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Glu Gln Lys Leu Ile Ser Glu Glu Asp Leu
1               5                   10

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Lys Glu Thr Ala Ala Ala Lys Phe Glu Arg Gln His Met Asp Ser
1               5                   10                  15

<210> SEQ ID NO 15
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro
        35

<210> SEQ ID NO 16
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 16

Ser Leu Ala Glu Leu Leu Asn Ala Gly Leu Gly Gly Ser
1               5                   10

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Thr Gln Asp Pro Ser Arg Val Gly
1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Trp Ser His Pro Gln Phe Glu Lys
1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Cys Cys Pro Gly Cys Cys
1               5

<210> SEQ ID NO 20
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Lys Pro Ile Pro Asn Pro Leu Leu Gly Leu Asp Ser Thr
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Tyr Thr Asp Ile Glu Met Asn Arg Leu Gly Lys
1               5                   10
```

```
<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Asp Leu Tyr Asp Asp Asp Asp Lys
1               5

<210> SEQ ID NO 23
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Thr Asp Lys Asp Met Thr Ile Thr Phe Thr Asn Lys Lys Asp Ala Glu
1               5                   10                  15

<210> SEQ ID NO 24
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ala His Ile Val Met Val Asp Ala Tyr Lys Pro Thr Lys
1               5                   10

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gatctcatca tcaccatcac catg                                          24

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gatccatggt gatggtgatg atga                                          24

<210> SEQ ID NO 27
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 27

Gln Pro Asn Asp Gly Gln Ser His Val Gly Ser Asp Asn His Tyr Ser
1               5                   10                  15

Ala Ser Thr Thr Met
            20

<210> SEQ ID NO 28
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Val His Asp Ser His Tyr Ser Gly Gln Gly Ala Met Ser Asp Asn Thr
1               5                   10                  15

Asn Ser Pro Gln Thr
            20
```

SUPPRESSION OF SPLA2-INTEGRIN BINDING FOR TREATING AN INFLAMMATORY CONDITION OR SUPPRESSING CELL PROLIFERATION

STATEMENT AS TO RIGHTS TO INVENTIONS MADE UNDER FEDERALLY SPONSORED RESEARCH OR DEVELOPMENT

This invention was made with support under Grant No. CA13015, provided by the National Institutes of Health. The government has certain rights in this invention.

RELATED APPLICATIONS

This application claims priority to U.S. Provisional Patent Application No. 62/079,943, filed on Nov. 14, 2014, the contents of which are hereby incorporated by reference in the entirety for all purposes.

REFERENCE TO A "SEQUENCE LISTING" A TABLE, OR A COMPUTER PROGRAM LISTING APPENDIX SUBMITTED IN ELECTRONIC FORMAT

The instant application contains a sequence listing which has been submitted electronically in ascii format and is hereby incorporated by reference in its entirety. said ascii copy, created on Oct. 24, 2019, is named 081906-1049237-219210us_sl.txt and is 8,174 bytes in size.

BACKGROUND OF THE INVENTION

Integrins are activated by signaling from inside the cell (inside-out signaling) through global conformational changes of integrins. The present inventors recently discovered that fractalkine activates integrins in the absence of CX3CR1 through the direct binding of fractalkine to a ligand-binding site in the integrin headpiece (site 2) that is distinct from the classical RGD-binding site (site 1). The inventors propose that fractalkine binding to the newly identified site 2 induces activation of site 1 though conformational changes (in an allosteric mechanism). It is reasoned that site 2-mediated activation of integrins is not limited to fractalkine. Human secreted phospholipase A2 type IIA (sPLA2-IIA), a pro-inflammatory protein, binds to integrins αvβ3 and α4β1 (site 1) and this interaction initiates a signaling pathway that leads to cell proliferation and inflammation. Human sPLA2-IIA does not bind to M-type receptor very well. Here the inventors describe that sPLA2-IIA directly activated purified soluble integrin αvβ3 and transmembrane αvβ3 on the cell surface. This activation did not require catalytic activity or M-type receptor. Docking simulation predicted that sPLA2-IIA binds to site 2 in the closed-headpiece of αvβ3. A peptide from site 2 of integrin β1 specifically bound to sPLA2-IIA and suppressed sPLA2-IIA-induced integrin activation. This suggests that sPLA2-IIA activates αvβ3 through binding to site 2. sPLA2-IIA also activated integrins α4β1 and α5β1 in a site 2-mediated manner. The present inventors recently identified small compounds that bind to sPLA2-IIA and suppress integrin-sPLA2-IIA interaction (e.g., Compound 21 or Cmpd21). Cmpd21 effectively suppressed sPLA2-IIA-induced integrin activation. These results define a novel mechanism of pro-inflammatory action of sPLA2-IIA through integrin activation.

BRIEF SUMMARY OF THE INVENTION

In one aspect, the present invention provides a method for identifying an inhibitor for integrin-sPLA2-IIA binding. The method comprises the steps of: (a) contacting a test compound with sPLA2-IIA and an integrin β fragment, i.e., a polypeptide comprising a site 2 sequence of an integrin β (e.g., any one of SEQ ID NO:1, 2, 3, or 4) but not the full length of the integrin, under conditions that permit specific binding between sPLA2-IIA and the polypeptide; and (b) determining the level of specific binding between sPLA2-IIA and the polypeptide, wherein a decrease in the level of specific binding compared to a control level of specific binding between sPLA2-IIA and polypeptide under the same conditions but in the absence of the test compound indicates the compound as an inhibitor for integrin-sPLA2-IIA binding.

In some embodiments, the integrin β fragment is present on the surface of a cell (e.g., the U937 human monocytic lymphoma cell or the K562 cell). In some embodiments, the integrin β fragment is recombinantly expressed. In some embodiments, sPLA2-IIA is immobilized on a solid support. In some embodiments, the integrin β fragment is immobilized on a solid support. In some embodiments, sPLA2-IIA is labeled with a fluorescent dye, for example, fluorescein isothiocyanate (FITC). The integrin β fragment may be in the length range of no more than 200, 150, 100, 80, 70, 60, 50, 40, 30, or 25 amino acids. In some embodiments, the integrin β fragment comprises the amino acid sequence set forth in SEQ ID NO:1. In some embodiments, the integrin β fragment comprises the amino acid sequence set forth in SEQ ID NO:2. In some embodiments, the integrin β fragment comprises the amino acid sequence set forth in SEQ ID NO:3. In some embodiments, the integrin β fragment comprises the amino acid sequence set forth in SEQ ID NO:4. In some embodiments, the integrin β fragment further comprises at least one heterologous amino acid sequence at the C- and/or N-terminus of the amino acid sequence set forth in SEQ ID NO:1, 2, 3, or 4.

In a second aspect, the invention provides a method for treating an inflammatory condition or suppressing cell proliferation. The method includes the step of administering to a subject an effective amount of an inhibitor for sPLA2-IIA and integrin binding. In some embodiments, the inhibitor is an integrin β fragment comprising the amino acid sequence set forth in SEQ ID NO:1. In some embodiments, the inhibitor is an integrin β fragment comprising the amino acid sequence set forth in SEQ ID NO:2. In some embodiments, the inhibitor is an integrin β fragment comprising the amino acid sequence set forth in SEQ ID NO:3. In some embodiments, the inhibitor is an integrin β fragment comprising the amino acid sequence set forth in SEQ ID NO:4. In some embodiments, the inhibitor is an integrin β fragment comprising the amino acid sequence set forth in SEQ ID NO:1, 2, 3, or 4 but not the full length integrin β. The fragment may be in the length range of less than 200, 150, 100, 80, 70, 60, 50, 40, 30, or 25 amino acids. The fragment may further have one or two heterologous amino acid sequences located at its N-terminus and/or C-terminus, such as a tag for affinity to facilitate identification or isolation during a recombinant production process. In some embodiments, the inhibitor is an integrin β fragment consisting of the amino acid sequence set forth in SEQ ID NO:1, 2, 3, or 4, optionally with one or two heterologous amino acid sequences located at its N-terminus and/or C-terminus. When the inhibitor is a polypeptide, e.g., an integrin β fragment described herein, it could be either a linear or cyclic polypeptide, for example, a linear peptide or a cyclic peptide having the amino acid sequence of SEQ ID NO:1 or 3. In some embodiments, the inhibitor is Compound 21. In some embodiments, the inhibitor is a nucleic acid encoding an integrin β fragment comprising the amino acid sequence set forth in any one of SEQ ID NO:1, 2, 3, or 4. Optionally, more than one inhibitor can be used simultaneously, including a known anti-inflammatory agent or anti-tumor agent such as chemotherapeutic agent.

In a third aspect, the present invention provides a composition that may be useful for treating a condition involving an inflammatory condition or undesirable cell proliferation. The composition comprises: (1) an effective amount of an inhibitor for sPLA2-IIA and integrin binding and (2) a pharmaceutically acceptable carrier. In some embodiments, the inhibitor is an integrin β fragment comprising the amino acid sequence set forth in any one of SEQ ID NO:1, 2, 3, or 4. In some embodiments, the inhibitor is an integrin β fragment comprising the amino acid sequence set forth in SEQ ID NO:1 or SEQ ID NO:3. In some embodiments, the inhibitor is an integrin β fragment comprising the amino acid sequence set forth in SEQ ID NO:1, 2, 3, or 4 but not the full length integrin β. The fragment may be in the length range of less than 200, 150, 100, 80, 70, 60, 50, 40, 30, or 25 amino acids. The fragment may further have one or two heterologous amino acid sequences located at its N-terminus and/or C-terminus, such as a tag for affinity to facilitate identification or isolation during a recombinant production process. In some embodiments, the inhibitor is an integrin β fragment consisting of the amino acid sequence set forth in SEQ ID NO:1, 2, 3, or 4, optionally with one or two heterologous amino acid sequences located at its N-terminus and/or C-terminus. When the inhibitor is a polypeptide, e.g., an integrin β fragment described herein, it could be either a linear or cyclic polypeptide, for example, a linear peptide or a cyclic peptide having the amino acid sequence of SEQ ID NO:1 or 3. In some embodiments, wherein the inhibitor is Compound 21. In some embodiments, the inhibitor is a nucleic acid encoding an integrin β fragment comprising the amino acid sequence set forth in SEQ ID NO:1. In some embodiments, the inhibitor is a nucleic acid encoding an integrin β fragment comprising the amino acid sequence set forth in SEQ ID NO:2. In some embodiments, the inhibitor is a nucleic acid encoding an integrin β fragment comprising the amino acid sequence set forth in SEQ ID NO:3. In some embodiments, the inhibitor is a nucleic acid encoding an integrin β fragment comprising the amino acid sequence set forth in SEQ ID NO:4. Optionally, the composition can further contain an additional therapeutic compound, for example, an anti-inflammatory or anti-tumor agent (e.g., chemotherapeutic agent).

In a fourth aspect, the present invention provides a kit for treating an inflammatory condition or a condition involving undesirable cell proliferation. The kit contains a composition effective for suppressing inflammatory and/or cell proliferation described in this disclosure. In some cases, the kit contains a plurality of separate containers each containing a pre-determined dose of the composition. In some cases, user instructions for the application of the composition are included in the kit.

and site 2 peptides (200 µg/ml) were used. f. Suppression of γC399tr to β3-CHO cells by site 2 peptide. The binding of FITC-labeled γC399tr to αvβ3 on β3-CHO was measured in flow cytometry as described in the Methods section. Data are shown as means±SEM of MFI of three independent experiments. sPLA2-IIA (20 µg/ml) and site 2 peptides (200 µg/ml) were used.

Figure 4:
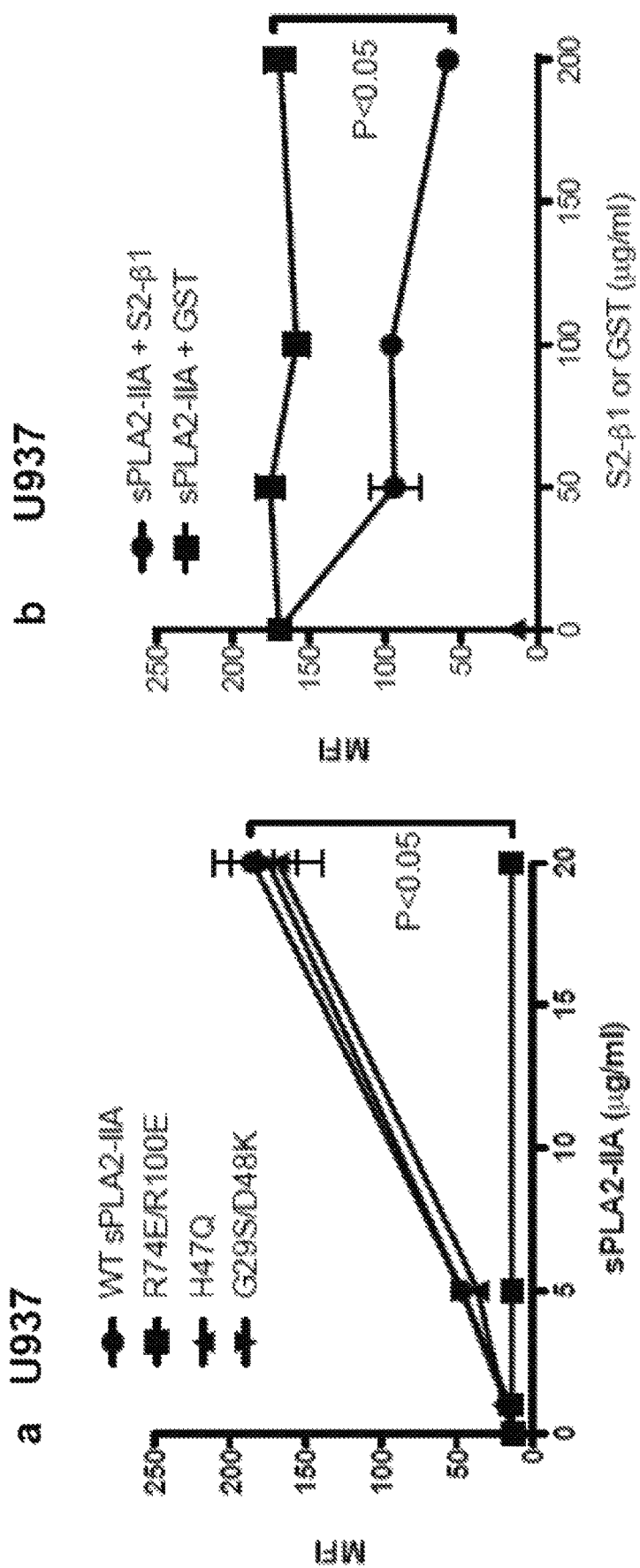
Figure 4:
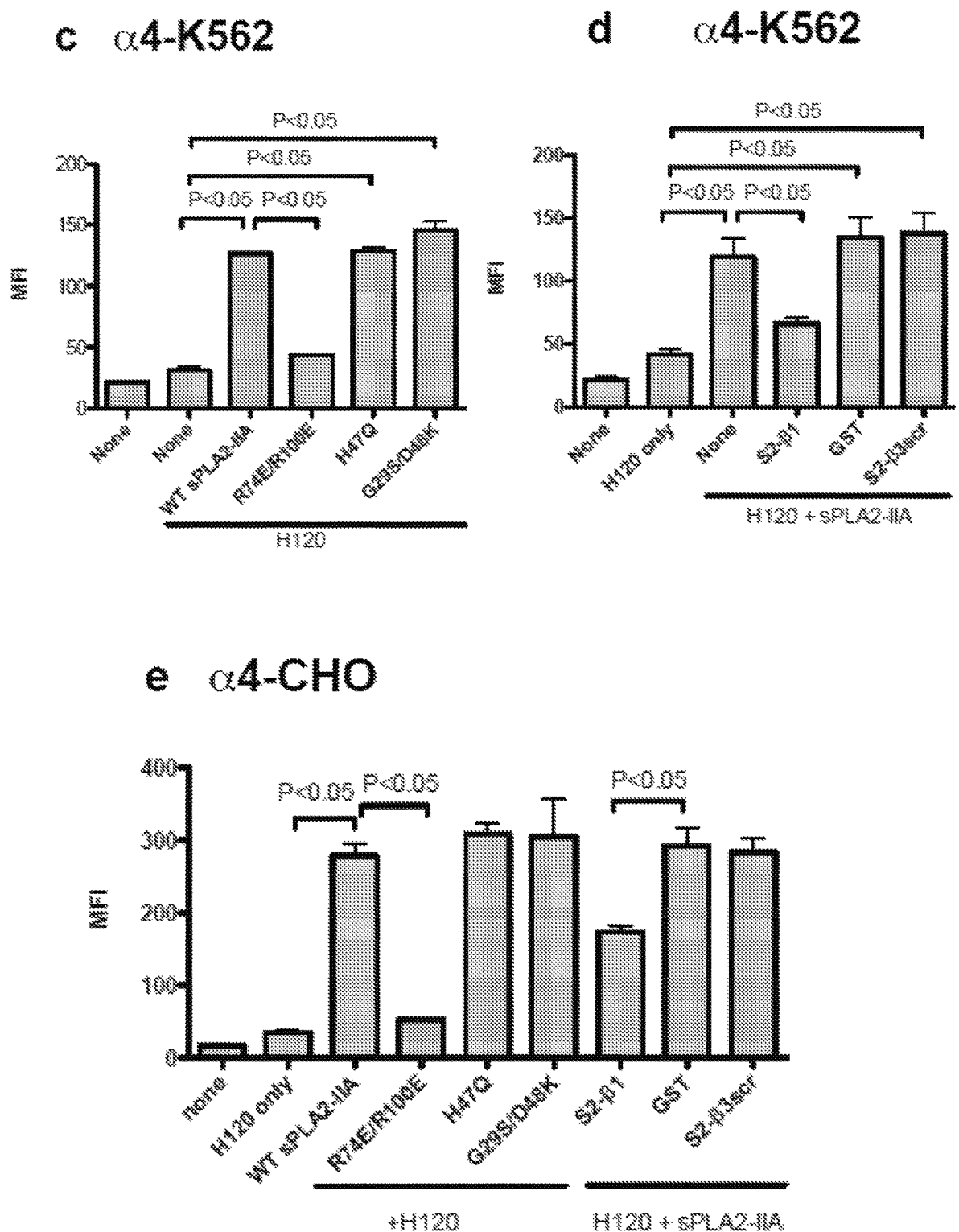

FIG. 4. sPLA2-IIA enhances the binding of the fibronectin fragment that contains CS-1 (H120) to α4β1 through binding to site 2. a. The binding of FITC-labeled FN H120 fragment (an α4β1-specific ligand) to α4β1 on U937 cells was measured by flow cytometry. WT sPLA2-IIA, catalytically inactive mutant (H47A), and the receptor-binding mutant (G29S/D48K) enhance the binding of H120 to α4β1, but the integrin-binding defective mutant (R74E/R100E) does not. Data are shown as means±SEM of MFI of three independent experiments. b. Site 2 peptide from β1 (S2-β1) suppressed sPLA2-IIA-induced α4β1 activation in U937 cells (20 µg/ml WT sPLA2-IIA was used). Data are shown as means±SEM of MFI of three independent experiments. c, d, e. sPLA2-IIA mutations and S2-β1 peptide affect α4β1 activation by sPLA2-IIA in α4-K562 (c and d), and α4-CHO (e) cells. The binding of FITC-labeled FN H120 fragment to α4β1+ cells was measured by flow cytometry. sPLA2-IIA (20 µg/ml) and site 2 peptides (200 µg/ml) were used. Data are shown as means±SEM of MFI of three independent experiments.

Figure 5:
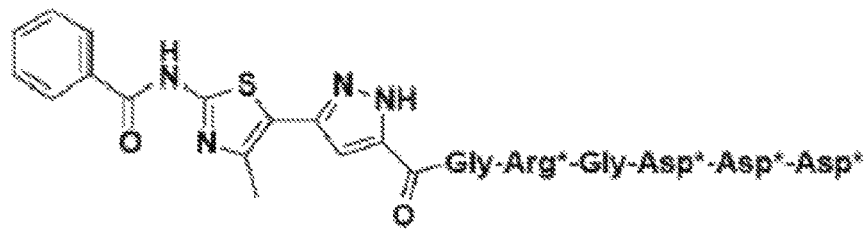
Figure 5:
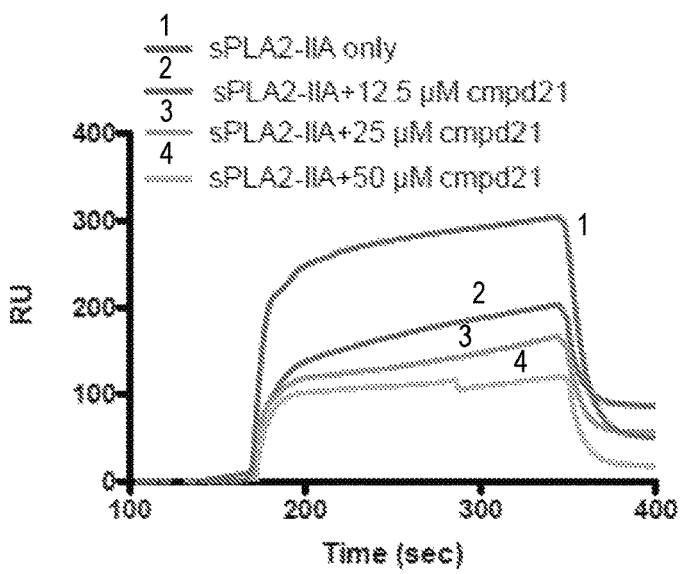
Figure 5:
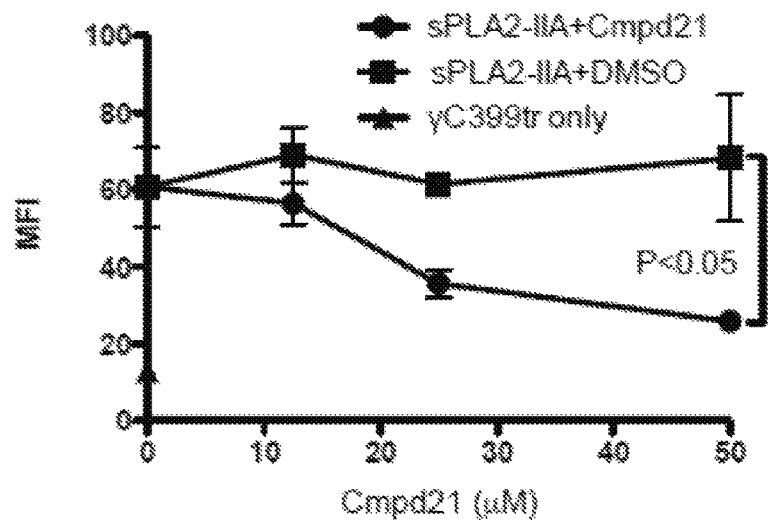
Figure 5:
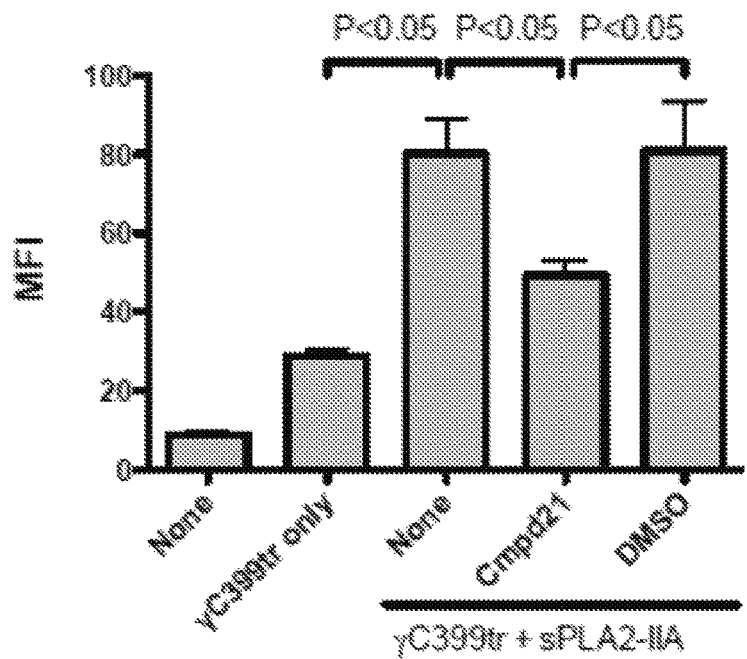
Figure 5:
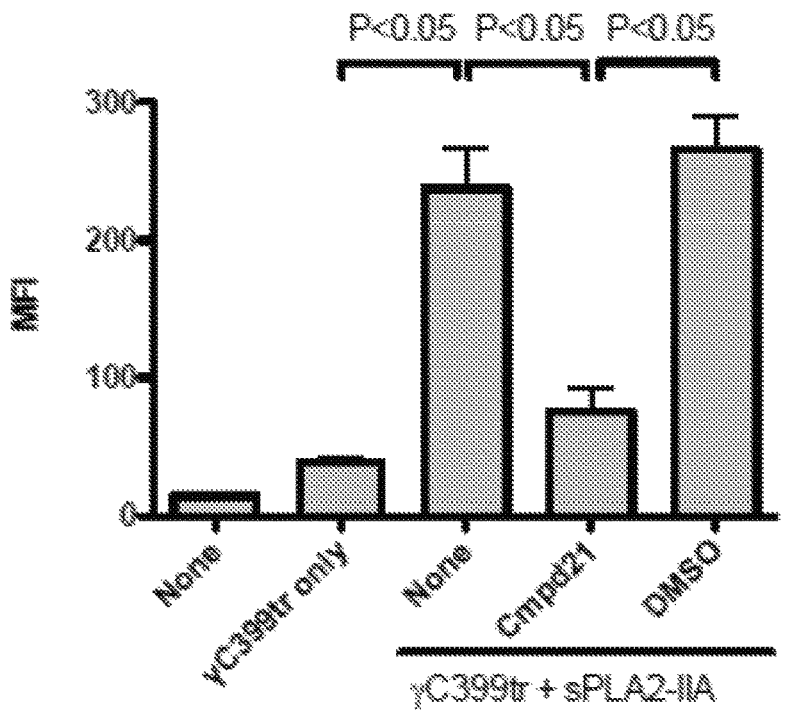

FIG. 5. Cmpd21 blocks the binding of γC399tr to α3 on the cell surface through binding to site 2. The effect of Cmpd21 on the binding of γC399tr to αvβ3 and on the sPLA2-IIA-induced integrin activation was studied. a. Structure of Cmpd21. Amino acids with asterisk are D isomers. b. Cmpd21 suppresses the binding of sPLA2-IIA to αvβ3. Soluble αvβ3 was immobilized to a sensor chip and Cmpd21 was added to the solution phase together with sPLA2-IIA in surface plasmon resonance (SPR) study. c-e. Cmpd21 suppressed the binding of FITC-labeled γC399tr enhanced by sPLA2-IIA (20 µg/ml) to αvβ3 on U937 (c), αvβ3-K562 (d), and β3-CHO cells (e). The concentration of Cmpd21 in d and e is 50 µM. Data are shown as means±SEM of MFI of three independent experiments.

Figure 6:
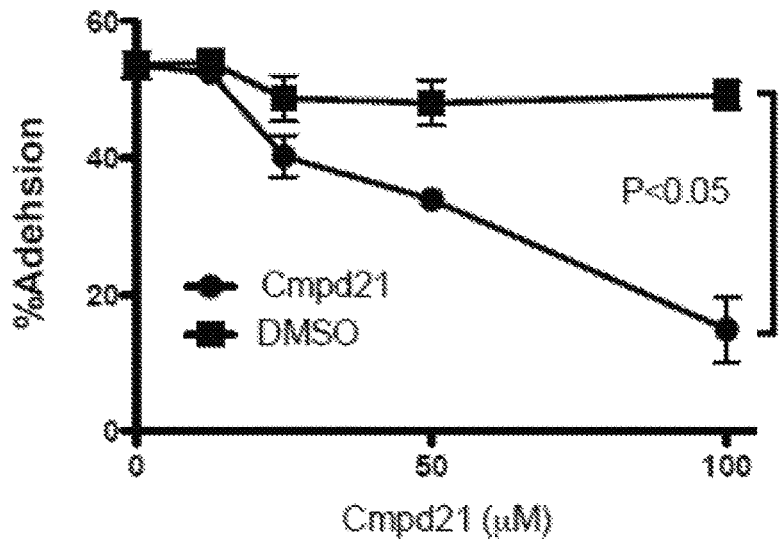
Figure 6:
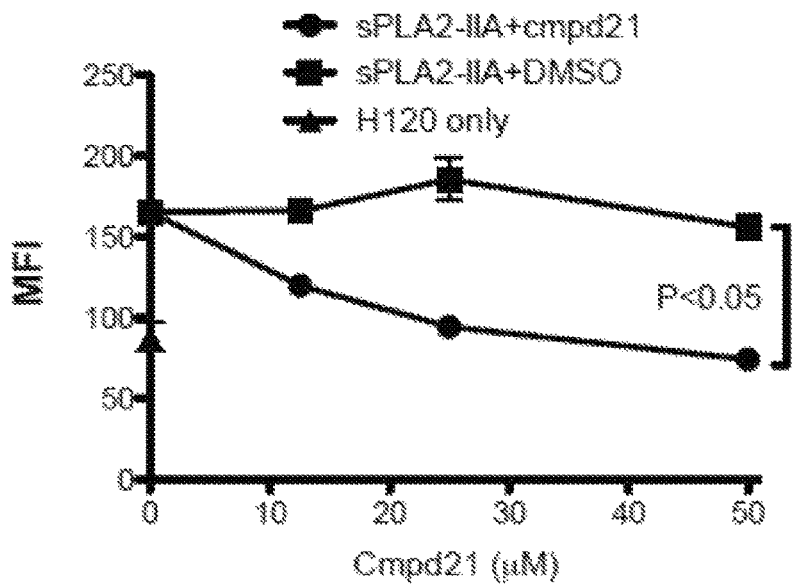
Figure 6:
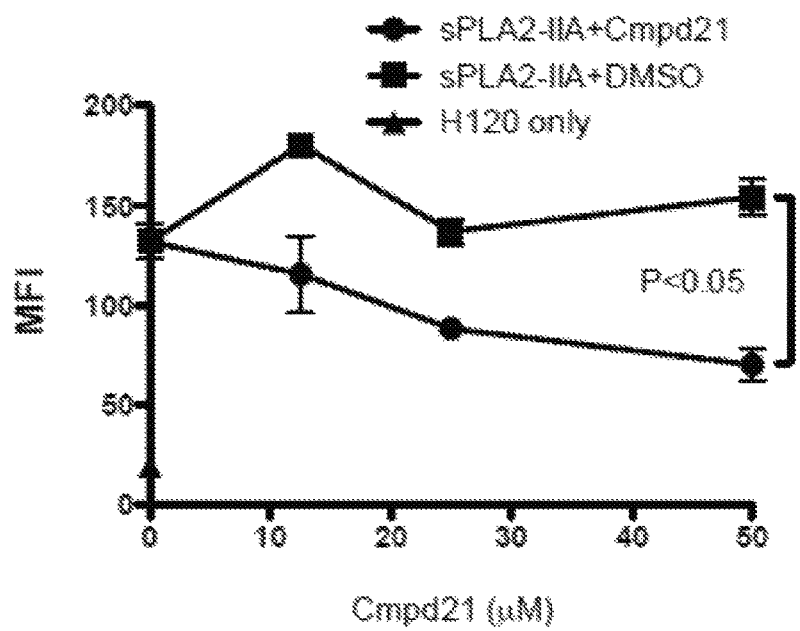
Figure 6:
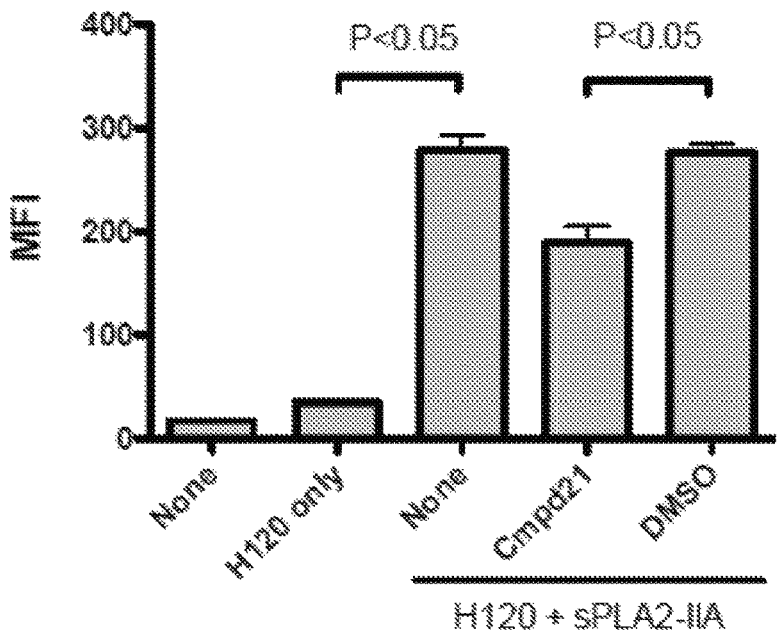

FIG. 6. Cmpd21 suppresses sPLA2-IIA-induced α4β1 activation in U937, α4-K562, and α4-CHO cells. a. Cmpd21 suppressed the binding of α4β1 to sPLA2-IIA. Adhesion of α4-K562 cells to sPLA2-IIA (at 10 µg/ml coating concentration) in RPMI1640 medium was measured. Data are shown as means±SEM of three independent experiments. b-d. Cmpd21 suppressed the binding of FITC-labeled H120 enhanced by sPLA2-IIA (20 µg/ml) to α4β1 on U937 (b), α4-K562 (c), and α4-CHO cells (d). The concentration of Cmpd21 in c and d is 50 µM in d. Data are shown as means±SEM of MFI of three independent experiments.

Figure 7:
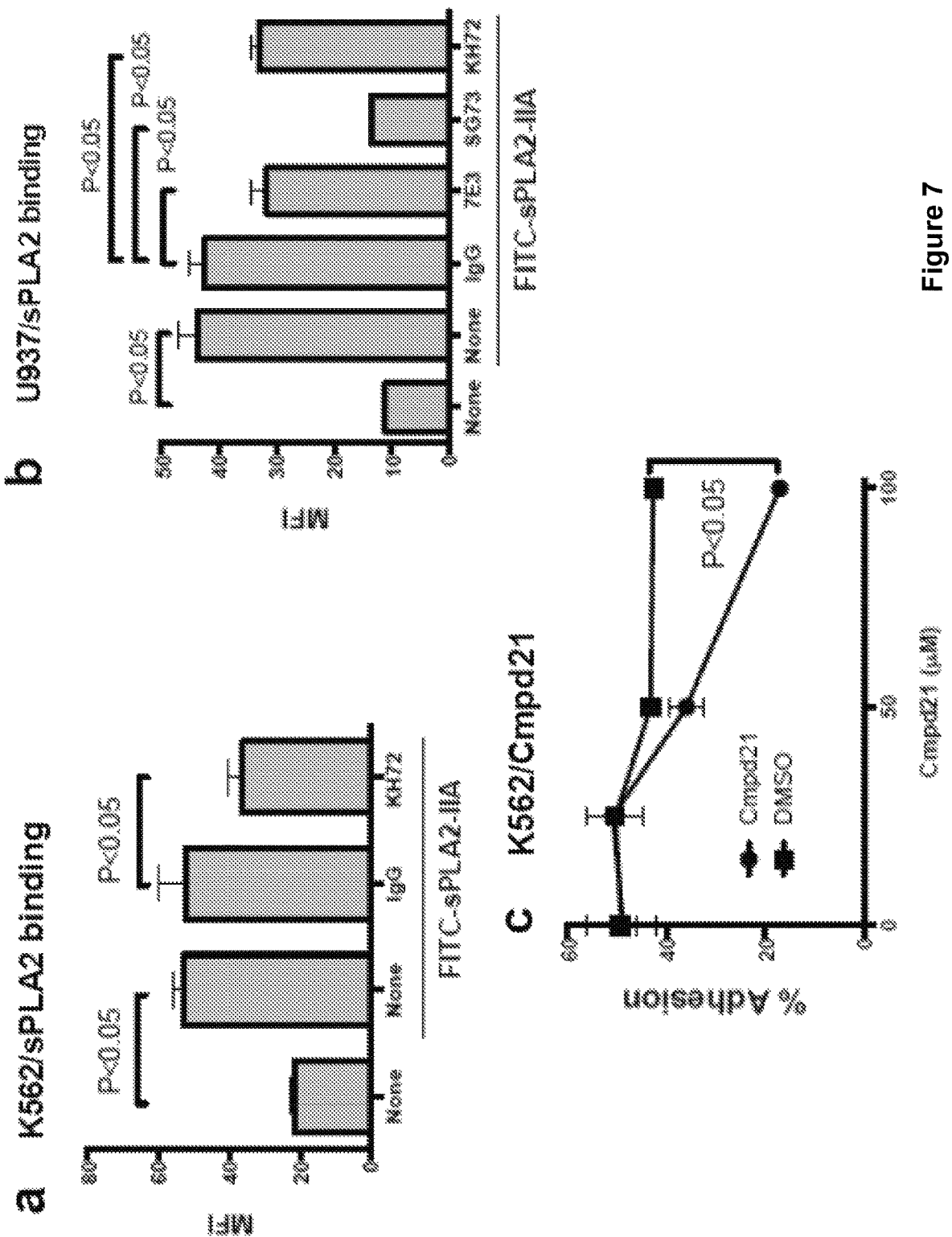
Figure 7:
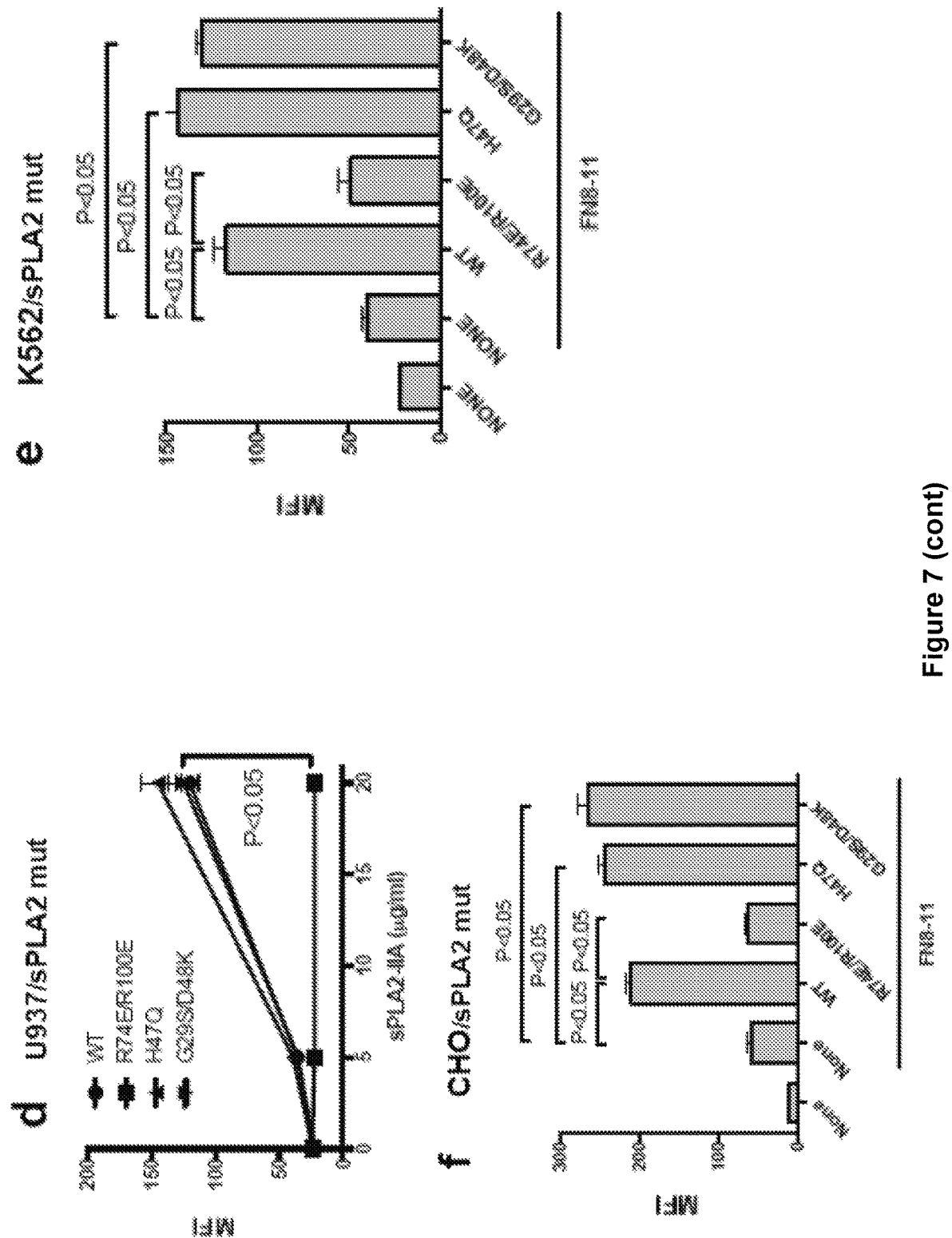
Figure 7:
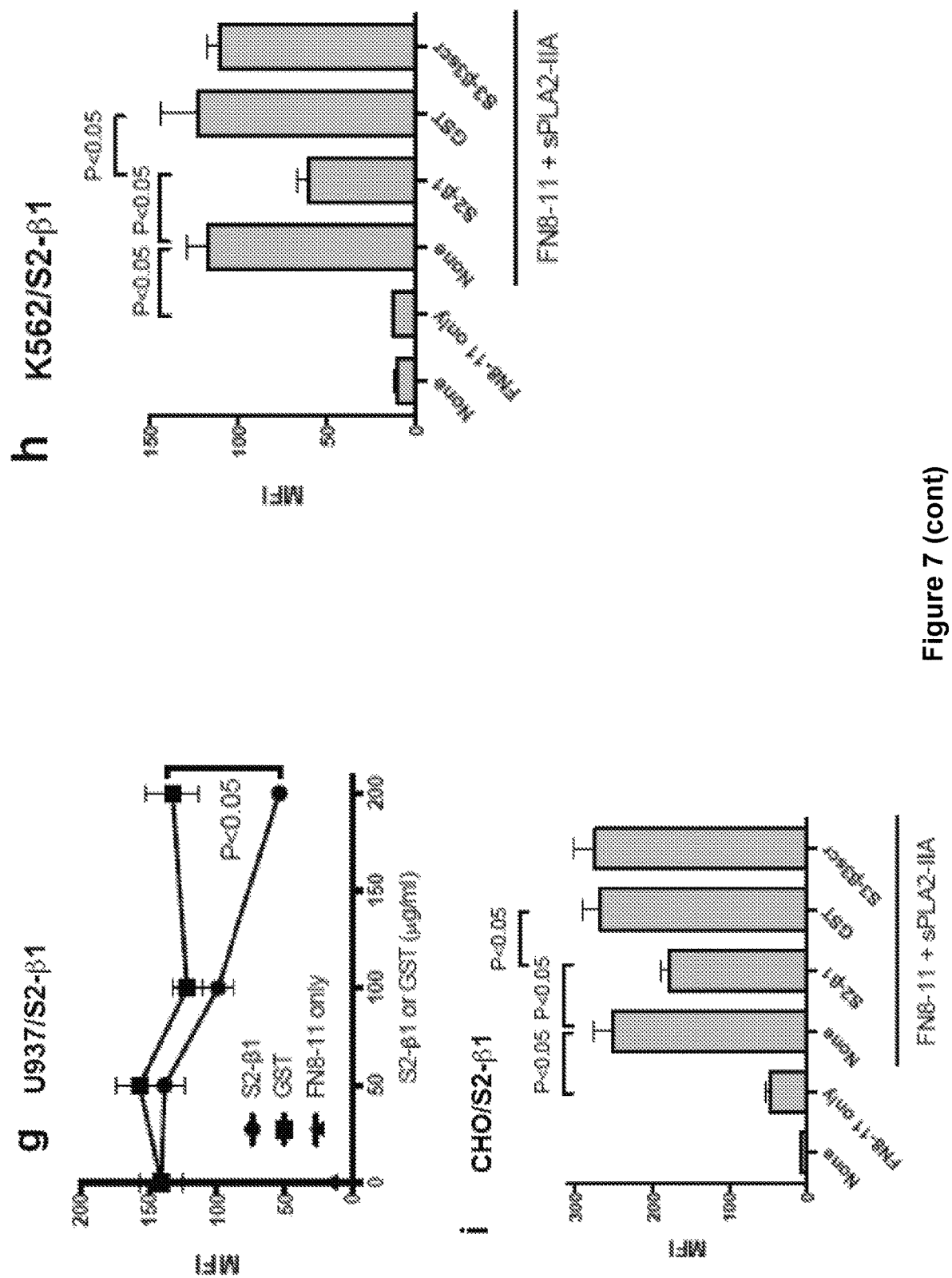
Figure 7:
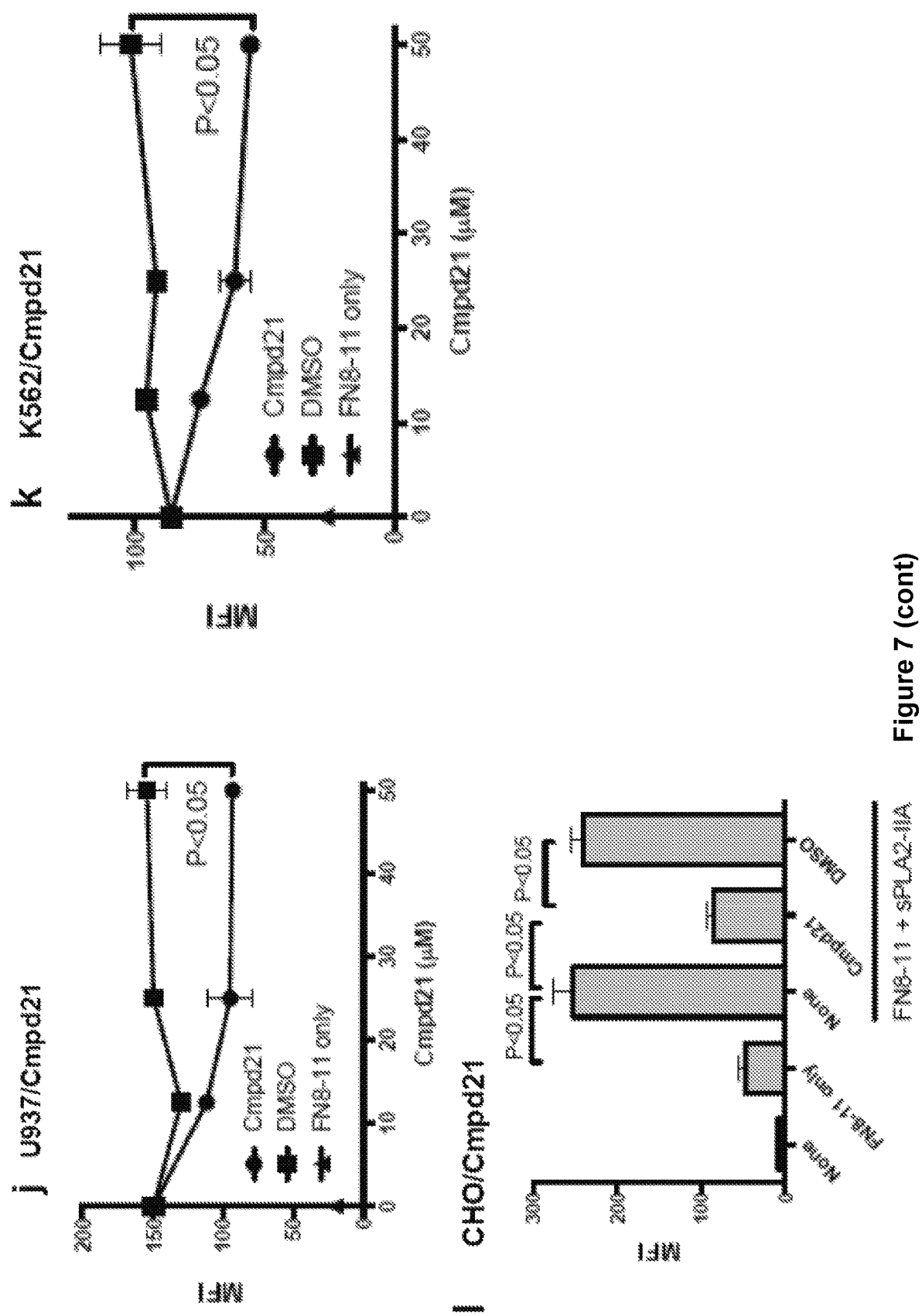

FIG. 7. sPLA2-IIA enhances the binding of the RGD-containing fibronectin fragment (FNS-11) to α5β1 through binding to site 2. sPLA2-IIA at 20 µg/ml and FN8-11 at 20 µg/ml were used if not indicated otherwise. a and b. Specific binding of sPLA2-IIA to integrin α5β1. FITC-labeled sPLA2-IIA (10 µg/ml) was incubated with K562 cells (a) or U937 cells (b) in the presence of mouse IgG, KH72 (anti-α5 mAb), SG73 (anti-α4) or 7E3 (anti-β3 mAb) (10 µg/ml). Bound FITC was measured using flow cytometry. Data are shown as means±SEM of MFI of three independent experiments. c. Comp21 suppresses sPLA2 binding to α5β1. Adhesion of K562 cells to sPLA2-IIA (coating concentration 10 µg/ml) was measured in the presence of Cmpd21. Data are shown as means±SEM of % adhesion of three independent experiments. d-f. The effect of sPLA2-IIA mutants on the binding of FITC-FN8-11 was measured in U937 cells (d), K562 cells (e), and CHO cells (f). Data are shown as means±SEM of MFI of three independent experiments. FITC-sPLA2-IIA was used at 20 µg/ml if not indicated otherwise. g-i. The binding of FITC-FN8-11 to U937 cells (g), K562 cells (h), or CHO cells (i) was measured in the presence of S2-β1 peptide. Data are shown as means±SEM of MFI of three independent experiments. j-l. The binding of FITC-FN8-11 to U937 cells (j), K562 cells (k) or CHO cells (l) was measured in the presence of Cmpd21. Data are shown as means±SEM of MFI of three independent experiments.

Figure 8:
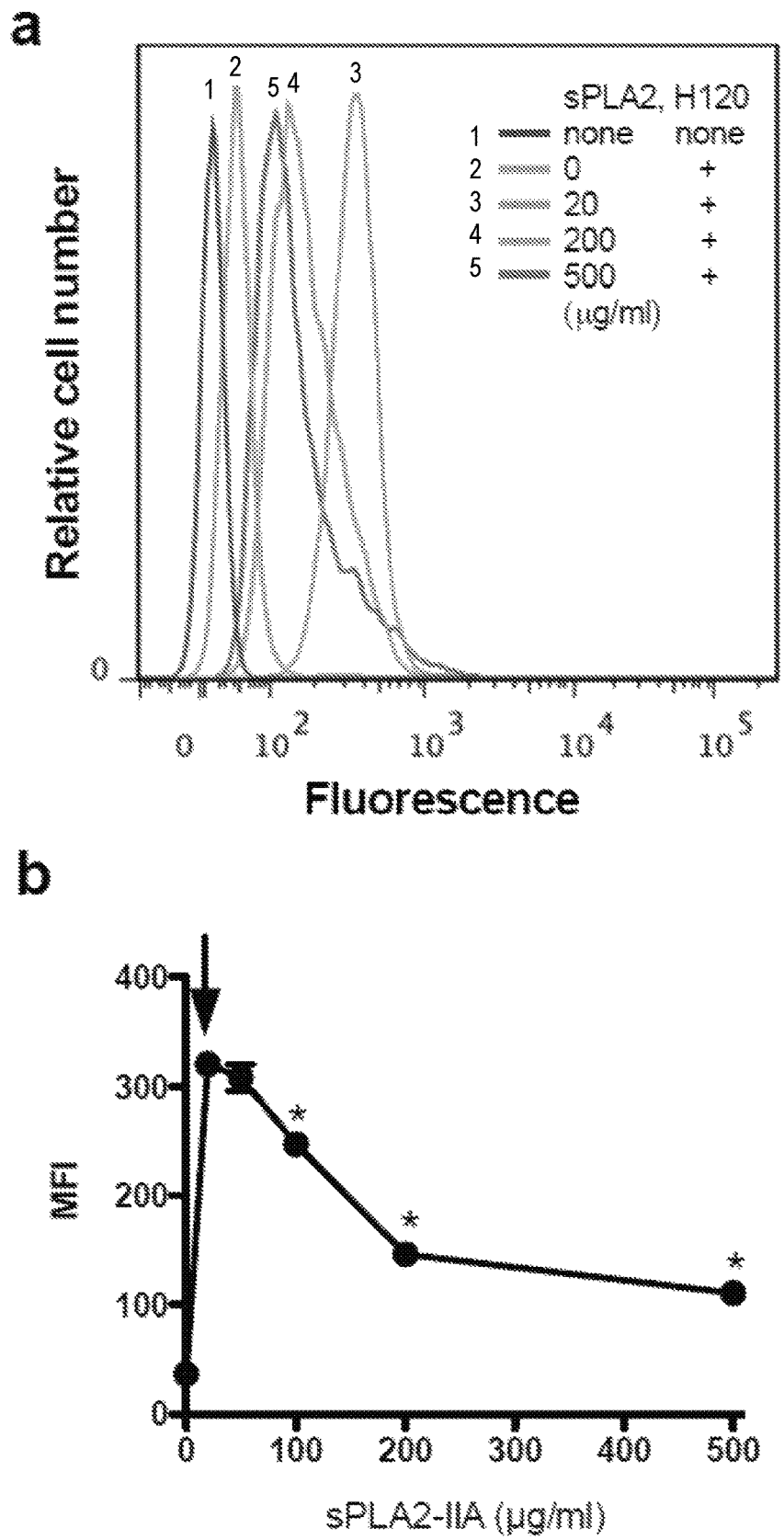

FIG. 8. sPLA2-IIA suppresses the binding of H120 to site 1 in α4β1. The binding of H120 to α4-CHO cells as a function of sPLA2-IIA concentrations. The binding of FITC-H120 (10 µg/ml) was measured in flow cytometry (a). Data are shown as means±SEM of MFI of three independent experiments (b). * $P<0.05$ compared to the MFI at 20 µg/ml sPLA2-IIA (arrow).

Figure 9:
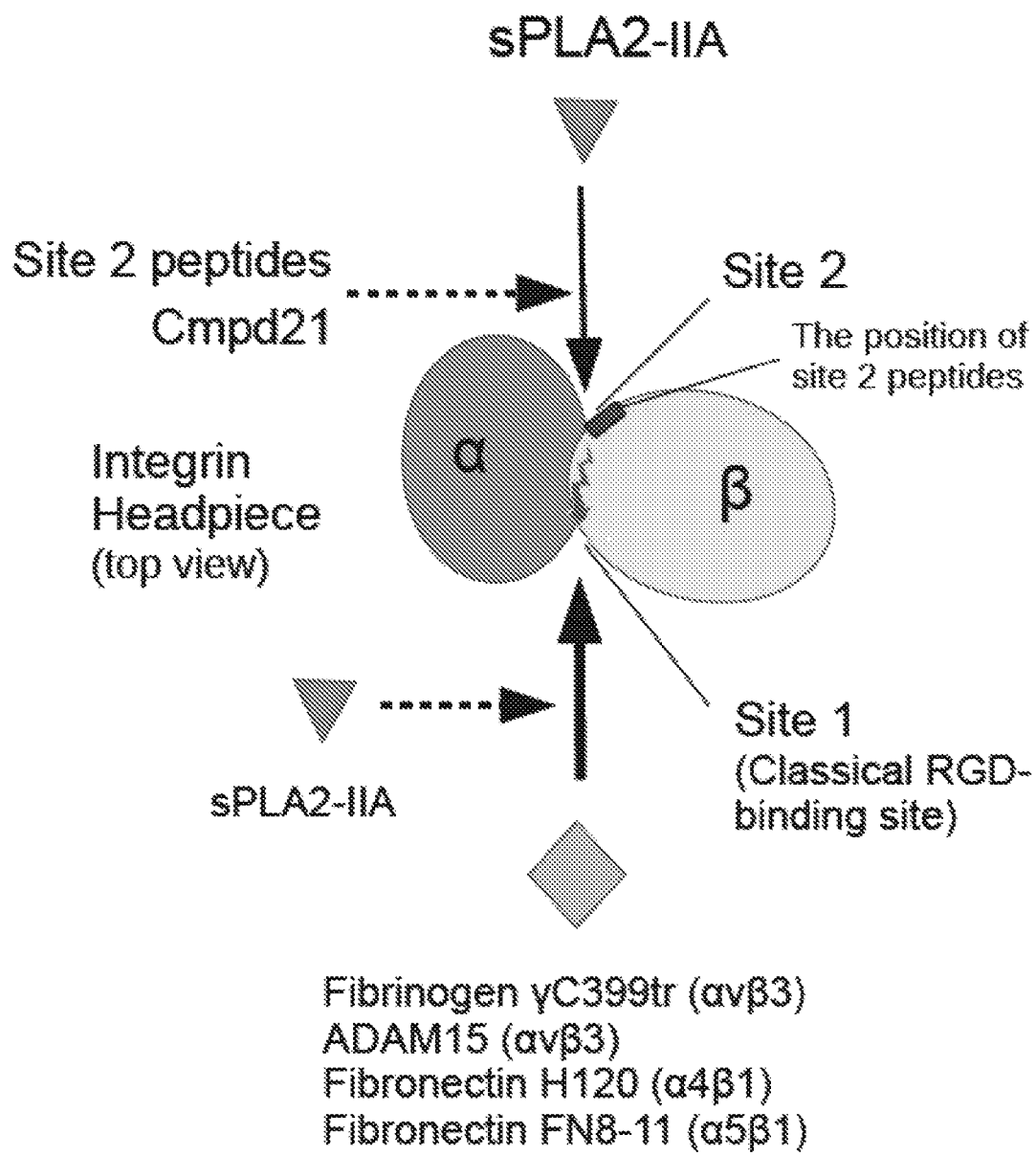

FIG. 9. A model of sPLA2-IIA-induced integrin activation through site 2. A model is proposed, in which sPLA2-IIA binds to site 2 of inactive/closed-headpiece integrins and induces conformational changes and enhance ligand binding to site 1 (the classical RGD-binding site). This activation is blocked by a peptide that is derived from site 2 or a small compound (Cmpd21) that binds to the integrin-binding site of sPLA2-IIA.

Figure 10:
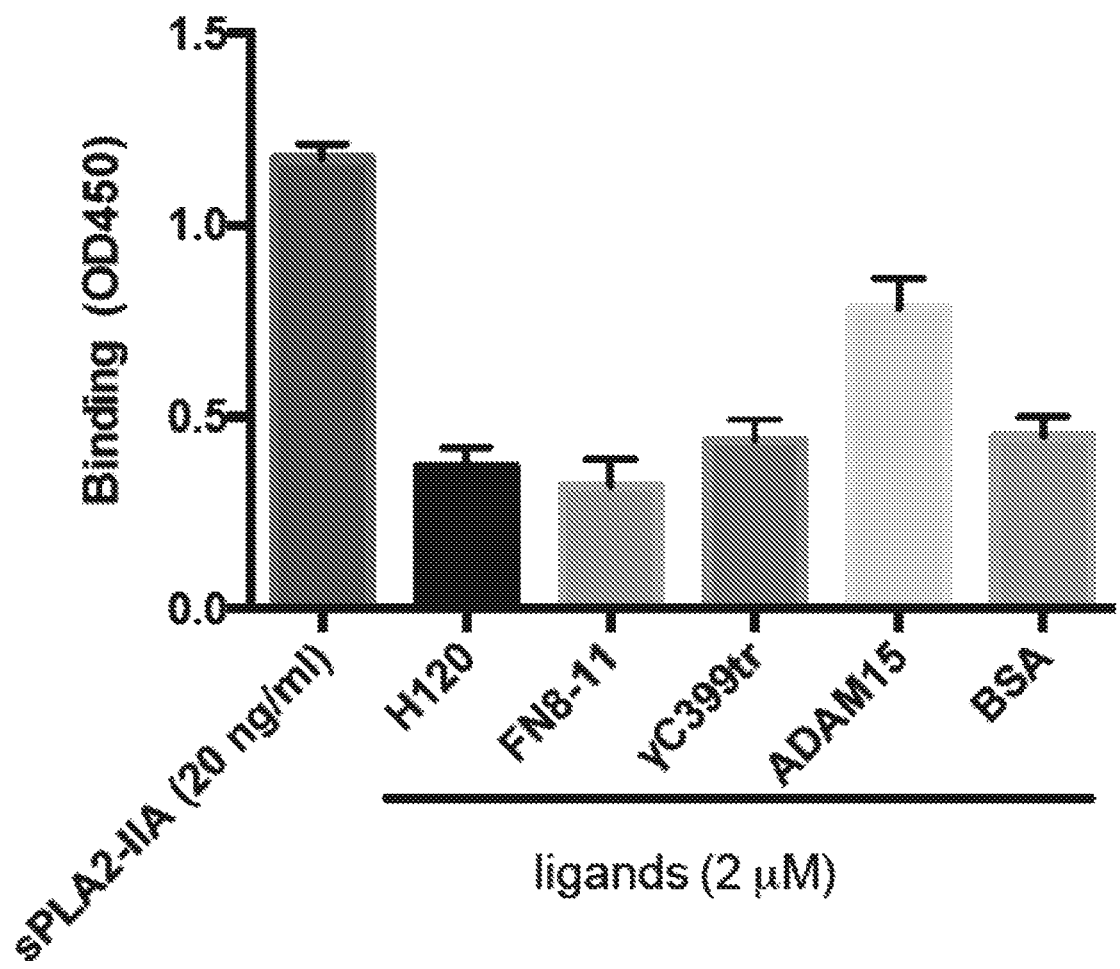

FIG. 10. Lack of binding of sPLA2-IIA to integrin ligands used in the present study. Wells of 96-well microtiter plates were coated with ligands (2 µM coating concentration) and the remaining protein-binding sites were blocked with BSA. The wells were then incubated with sPLA2-IIA (2 µM/ml in PBS) for 2 hours at room temperature, and bound sPLA2-IIA was determined using HRP-conjugated anti-6His antibody. sPLA2-IIA (20 ng/ml coating concentration, 1% of input sPLA2-IIA) was used as a positive control. Data are shown as means+/−SEM of triplicate experiments. Results indicate that there is little or no binding of sPLA2-IIA to the integrin ligands used in this study.

Figure 11:
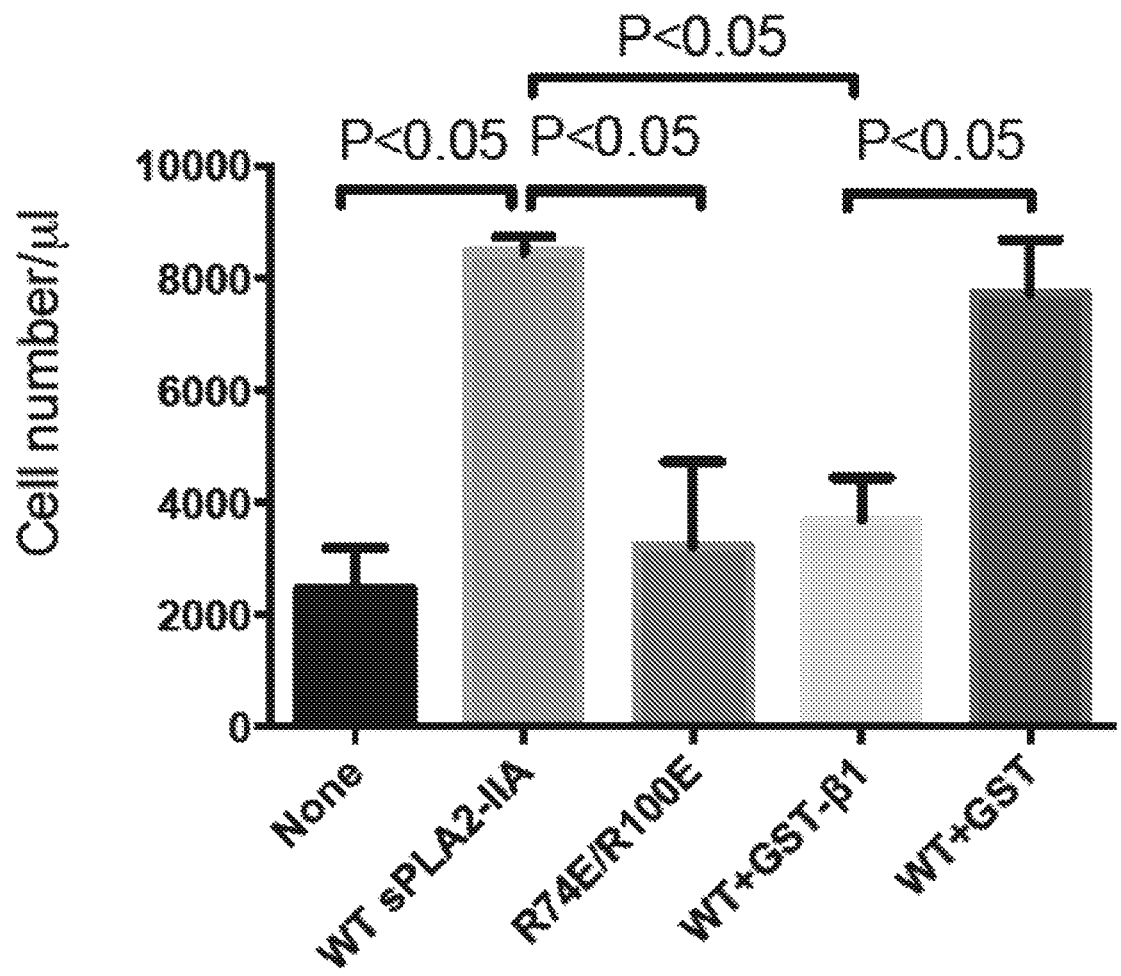

FIG. 11. S2-β1 peptide suppresses sPLA2-IIA-induced chemotaxis. Chemotaxis was measured in modified Boyden chambers. 1 µg/ml sPLA2-IIA and 20 µg/ml S2-β1 peptide or control peptides in 600 µl RPMI 1640 medium were placed in lower chamber, and U937 cells ($2\times10^5$ cells in 100 µl RPMI 1640 medium) were placed in the upper chamber. After 5 hours of incubation at 37° C., cells in the lower chamber was counted. Data indicate that site-2 peptides can be developed for therapeutic use.

Figure 12:
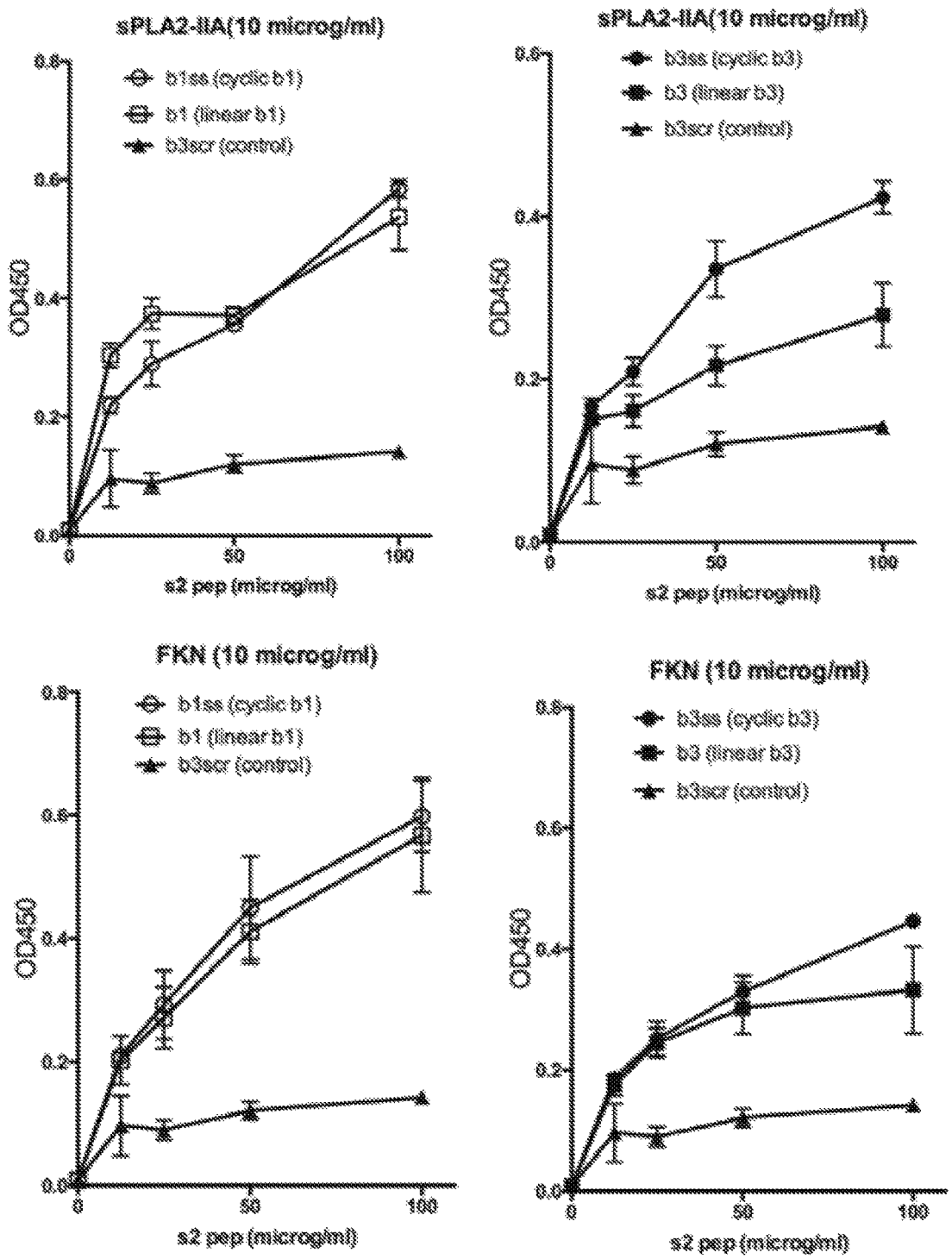

FIG. 12. Binding of linear and cyclic site 2 peptides to sPLA2-IIA and FKN. Cyclic site 2 peptides (β1 and β3) binding to sPLA2-IIA or fractalkine (FKN) was compared in ELISA binding assays. Cyclic β1 peptide was very similar to linear β1 peptide in its binding to sPLA2-IIA or FKN, but cyclic β3 peptide showed stronger binding ability than linear β3 peptide.

DEFINITIONS

"Inflammation" or an "inflammatory response" refers to an organism's immune response to irritation, toxic substances, pathogens, or other stimuli. The response can involve innate immune components and/or adaptive immunity. Inflammation is generally characterized as either chronic or acute. Acute inflammation is characterized by redness, pain, heat, swelling, and/or loss of function due to infiltration of plasma proteins and leukocytes to the affected area. Chronic inflammation is characterized by persistent inflammation, tissue destruction, and attempts at repair. Monocytes, macrophages, plasma B cells, and other lymphocytes are recruited to the affected area, and angiogenesis and fibrosis occur, often leading to scar tissue.

An "inflammatory condition" is one characterized by or involving an inflammatory response, as described above. A list of exemplary inflammatory conditions includes: asthma, autoimmune disease, chronic inflammation, chronic prostatitis, glomerulonephritis, hypersensitivities and allergies, skin disorders such as eczema, inflammatory bowel disease, pelvic inflammatory disease, reperfusion injury, rheumatoid arthritis, transplant rejection, and vasculitis.

As used herein, "sPLA2-IIA" refers to a member of the phospholipase A2 (PLA2) family, a secreted phospholipase. In this application, an "sPLA2-IIA protein" refers to a full-length sPLA2-IIA polypeptide sequence, including the human sPLA2-IIA (GenBank Accession No. P14555, encoded by GenBank Accession No. M22430), its polymorphic variants and species orthologs or homologs. An "sPLA2-IIA polynucleotide" refers to a nucleic acid sequence from the gene encoding the sPLA2-IIA protein and may include both the coding and non-coding regions. "sPLA2-IIA cDNA," "sPLA2-IIA mRNA," "sPLA2-IIA coding sequence," and their variations refer to a nucleic acid sequence that encodes an sPLA2-IIA polypeptide.

Similarly, the amino acid sequences of integrin chains 131, 32, 133, and 04 are provided in GenBank Accession Nos. P05556, M15395, P05106, and X51841, encoded by GenBank Accession Nos. X07979, AAA59490.1, J02703, and CAA36134.1, respectively. Each of these terms encompasses its corresponding polymorphic variants and interspecies orthologs/homologs.

"An integrin β fragment" as used in the context of interference of sPLA2-IIA and integrin binding refers to a non-naturally occurring polypeptide that (1) comprises a core sequence or a sequence corresponding to the integrin β site 2 sequence, such as those set forth in SEQ ID NOs: 1-4, which may fully correspond to a segment of the native integrin β protein or may contain one or two amino acid residues having been modified (e.g., inserted, deleted, or substituted) from the native the native integrin β protein sequence; (2) does not include the full length of an integrin β amino acid sequence (i.e., including at most a fragment of the integrin β) but optionally may include an additional 1, 2, 3, 4, 5, 6, 7, 8, 9, 10, 11, 12, 13, 14, 15, 16, 17, 18, 19, 20, 25, 30, 35, 40, 45, or up to 50 amino acids of the native integrin (3 sequence immediately next to the site 2 sequence at C- and/or N-terminus of the site 2 sequence. The fragment may be in the length range of no more than 200, 150, 100, 80, 70, 60, 50, 40, 30, or 25 amino acids. An integrin β fragment is capable of specifically binding to sPLA2-IIA due to the presence of the integrin β site-2 sequence but is not capable of signal transduction carried out by wild-type integrin due to the absence of the remainder of the integrin β chain. The integrin β fragment is therefore able to interfere with the binding between sPLA2-IIA and integrin by outcompeting integrin β for sPLA2-IIA binding. Optionally, the "integrin β fragment" may further comprise at least one peptide sequence of a heterologous origin (i.e., not derived from the same integrin β protein sequence), for example, any one of the "tags" known and used in the field of recombinant proteins: a peptide tag such as an AviTag, a peptide allowing biotinylation by the enzyme BirA and so the protein can be isolated by streptavidin (GLNDIFEAQKIEWHE (SEQ ID NO: 5)), a Calmodulin-tag, a peptide bound by the protein calmodulin (KRRWKKNFIAVSAANRFKKISSSGAL (SEQ ID NO: 6)), a polyglutamate tag, a peptide binding efficiently to anion-exchange resin such as Mono-Q (EEEEEE (SEQ ID NO: 7)), an E-tag, a peptide recognized by an antibody (GAPVPYPDPLEPR (SEQ ID NO: 8)), a FLAG-tag, a peptide recognized by an antibody (DYKDDDDK (SEQ ID NO: 9)), an HA-tag, a peptide recognized by an antibody (YPYDVPDYA (SEQ ID NO: 10)), a His-tag, 5-10 histidines (SEQ ID NO: 11) bound by a nickel or cobalt chelate (HHHHHH (SEQ ID NO: 12)), a Myc-tag, a short peptide recognized by an antibody (EQKLISEEDL (SEQ ID NO: 13)), an S-tag (KETAAAKFERQHMDS (SEQ ID NO: 14)), an SBP-tag, a peptide that specifically binds to streptavidin (MDEKTTGWRGGHVVEGLAGELEQLRARLEHHPQGQREP (SEQ ID NO: 15)), a Softag 1 for mammalian expression (SLAELLNAGLGGS (SEQ ID NO: 16)), a Softag 3 for prokaryotic expression (TQDPSRVG (SEQ ID NO: 17)), a Strep-tag, a peptide that binds to streptavidin or the modified streptavidin called streptactin (Strep-tag II: WSHPQFEK (SEQ ID NO: 18)), a TC tag, a tetracysteine tag that is recognized by FlAsH and ReAsH biarsenical compounds (CCPGCC (SEQ ID NO: 19)), a V5 tag, a peptide recognized by an antibody (GKPIPNPLLGLDST (SEQ ID NO: 20)), a VSV-tag, a peptide recognized by an antibody (YTDIEMNRLGK (SEQ ID NO: 21)), an Xpress tag (DLYDDDDK (SEQ ID NO: 22)); or a covalent peptide tags such as an Isopeptag, a peptide that binds covalently to pilin-C protein (TDKDMTITFTNKKDAE (SEQ ID NO: 23)), a SpyTag, a peptide that binds covalently to SpyCatcher protein (AHIVMVDAYKPTK (SEQ ID NO: 24)); or a protein tag such as a BCCP tag (Biotin Carboxyl Carrier Protein), a protein domain biotinylated by BirA enabling recognition by streptavidin, a Glutathione-S-transferase (GST) tag, a protein that binds to immobilized glutathione, a Green fluorescent protein (GFP) tag, a protein that is spontaneously fluorescent and can be bound by nanobodies, a Maltose binding protein (MBP) tag, a protein that binds to amylose agarose, a Nus-tag, a Thioredoxin-tag, an Fc-tag, derived from immunoglobulin Fc domain, allow dimerization and solubilization. Can be used for purification on Protein-A Sepharose; as well as other types of tags such as the Ty tag. Furthermore, the integrin β fragment may also include one or more D-amino acids or include chemical modifications such as glycosylation, PEGylation, crosslinking, and the like.—please insert SEQ ID NOs in this paragraph "Inhibitors" or "suppressors" of sPLA2-IIA and integrin binding refer to compounds that have an inhibitory or disruptive effect on the specific binding between sPLA2-IIA and an integrin β chain, as identified in in vitro and in vivo binding assays described herein. In some cases, an inhibitor directly binds to either sPLA2-IIA or integrin β chain, especially the β1 or β3 chain, such that specific binding between sPLA2-IIA and integrin β is suppressed or abolished. For instance, a polypeptide such as an integrin β fragment that specifically binds sPLA2-IIA may serve as an inhibitor. An exemplary integrin β fragment as an inhibitor is a peptide consisting of the amino acid sequence set forth in SEQ ID NO:1, 2, 3, or 4, and the peptide can be linear or cyclic. The peptide may optionally further include one or more heterologous amino acid sequence located at the N-terminus and/or C-terminus of the peptide. Inhibitors also include compounds such as small molecules that are capable of reducing or eliminating the binding between sPLA2-IIA and integrin β, e.g., Compound 21. Assays for inhibitors of sPLA2-IIA-integrin binding include, e.g., applying putative inhibitor compounds to a cell expressing the integrin β fragment in the presence of sPLA2-IIA under conditions that permit sPLA2-IIA-integrin binding and then determining the effect of the compounds on the binding, as described herein. Assays for the inhibitors also include cell-free systems, where samples comprising sPLA2-IIA and the integrin β fragment treated with a candidate inhibitor are compared to a control sample without the inhibitor to examine the extent of inhibition on the sPLA2-IIA-integrin binding. Control samples (not treated with inhibitors) are assigned a relative binding level of 100%. Inhibition of binding is achieved when the level of binding or relative to the control is about 90%, 80%, 70%, 50%, 20%, 10% or close to 0%.

A composition "consisting essentially of a sPLA2-IIA-integrin binding inhibitor" is one that includes an inhibitor of specific binding between sPLA2-IIA and integrin β (especially integrin β1 or β3) but no other compounds that contribute significantly to the inhibition of the binding. Such compounds may include inactive excipients, e.g., for formulation or stability of a pharmaceutical composition, or active ingredients that do not significantly contribute to the inhibition of sPLA2-integrin binding. Exemplary compounds consisting essentially of a sPLA2-integrin inhibitor include therapeutics, medicaments, and pharmaceutical compositions.

As used herein, an "effective amount" or a "therapeutically effective amount" means the amount of a compound that, when administered to a subject or patient for treating a disorder, is sufficient to prevent, reduce the frequency of, or alleviate the symptoms of the disorder. The effective amount will vary depending on a variety of the factors, such as a particular compound used, the disease and its severity, the age, weight, and other factors of the subject to be treated. Amelioration of a symptom of a particular condition by administration of a pharmaceutical composition described herein refers to any lessening, whether permanent or temporary, that can be associated with the administration of the pharmaceutical composition. For example, the amount of an inhibitor of sPLA2-IIA-integrin binding is considered therapeutically effective for treating an inflammatory condition or a condition involving undesired cell proliferation when treatment results in eliminated symptoms, delayed onset of symptoms, or reduced frequency or severity of symptoms such as discomfort, irritation, swelling, etc.

A "subject," or "subject in need of treatment," as used herein, refers to an individual who seeks medical attention due to risk of, or actual sufference from, a condition involving an undesirable inflammatory reaction or cell proliferation. The term subject can include both animals and humans. Subjects or individuals in need of treatment include those that demonstrate symptoms of the inflammatory condition and/or undesirable cell proliferation or are at risk of later developing these symptoms.

The term "nucleic acid" or "polynucleotide" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.*, 19:5081 (1991); Ohtsuka et al., *J. Biol. Chem.*, 260:2605-2608 (1985); and Cassol et al., (1992); Rossolini et al., *Mol. Cell. Probes*, 8:91-98 (1994)). The terms nucleic acid and polynucleotide are used interchangeably with gene, cDNA, and mRNA encoded by a gene.

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full length proteins (i.e., antigens), wherein the amino acid residues are linked by covalent peptide bonds.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

An "antibody" refers to a polypeptide substantially encoded by an immunoglobulin gene or immunoglobulin genes, or fragments thereof, which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains, respectively.

Antibodies exist, e.g., as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)′₂ dimer into an Fab′ monomer. The Fab′ monomer is essentially an Fab with part of the hinge region (see Paul, *Fundamental Immunology*, Third Ed., Raven Press, NY (1993)). While various antibody fragments are defined in terms of the digestion of an intact antibody, one of skill will appreciate that such fragments may be synthesized de novo either chemically or by utilizing recombinant DNA methodology. Thus, the term "antibody," as used herein, also includes antibody fragments either produced by the modification of whole antibodies or those synthesized de novo using recombinant DNA methodologies (e.g., single chain Fv). These antibody fragments are also useful for methods requiring antigen recognition.

Chimeric antibodies combine the antigen binding regions (variable regions) of an antibody from one animal with the constant regions of an antibody from another animal. Generally, the antigen binding regions are derived from a non-human animal, while the constant regions are drawn from human antibodies. The presence of the human constant regions reduces the likelihood that the antibody will be rejected as foreign by a human recipient.

"Humanized" antibodies combine an even smaller portion of the non-human antibody with human components. Generally, a humanized antibody comprises the hypervariable regions, or complementarily determining regions (CDR), of a non-human antibody grafted onto the appropriate framework regions of a human antibody. Antigen binding sites may be wild type or modified by one or more amino acid substitutions, e.g., modified to resemble human immunoglobulin more closely. Both chimeric and humanized antibodies are made using recombinant techniques, which are well-known in the art (see, e.g., Jones et al., *Nature*, 321: 522-525 (1986)).

The phrase "specifically (or selectively) binds to an antibody" or "specifically (or selectively) immunoreactive with," when referring to a protein or peptide, refers to a binding reaction that is determinative of the presence of the protein in the presence of a heterogeneous population of proteins and other biologics. Thus, under designated immunoassay conditions, the specified antibodies bind to a particular protein and do not bind in a significant amount to other proteins present in the sample. Specific binding to an antibody under such conditions may require an antibody that is selected for its specificity for a particular protein, e.g., sPLA2-IIA or an integrin α or β chain. For example, antibodies raised against sPLA2-IIA can be selected to obtain antibodies specifically immunoreactive with that protein and not with other proteins, except for polymorphic variants, e.g., proteins at least 80%, 85%, 90%, 95%, or 99% identical to sPLA2-IIA or a fragment thereof, e.g., a domain or unique subsequence. A variety of immunoassay formats may be used to select antibodies specifically immunoreactive with a particular protein. For example, solid-phase ELISA immunoassays, Western blots, or immunohistochemistry are routinely used to select monoclonal antibodies specifically immunoreactive with a protein. See Harlow and Lane *Antibodies, A Laboratory Manual*, Cold Spring Harbor Publications, NY (1988) for a description of immunoassay formats and conditions that can be used to determine specific immunoreactivity. Typically, a specific or selective reaction will be at least twice the background signal or noise and more typically more than 10 to 100 times background.

DETAILED DESCRIPTION OF THE INVENTION

I. Introduction

Secreted PLA2 type IIA (sPLA2-IIA) was first isolated and purified from rheumatoid synovial fluid (1). sPLA2-IIA is an acute phase reactant and its plasma concentration markedly increases in diseases that involve systemic inflammation such as sepsis, rheumatoid arthritis, and cardiovascular disease (up to 1000-fold and >1 µg/ml). Inflammatory cytokines such as IL-6, TNF-α, and IL-1β induce synthesis and release of sPLA2-IIA in arterial smooth muscle cells and hepatocytes, which are the major sources of the plasma sPLA2-IIA in these systemic inflammatory conditions (2,3). In addition to being a pro-inflammatory protein, sPLA2-IIA expression is elevated in neoplastic prostatic tissue (4) and dysregulation of sPLA2-IIA may play a role in prostatic carcinogenesis (5), and is a potential therapeutic target in prostate cancer (6).

Notably some biological effects associated with sPLA2-IIA are independent of its catalytic function (7). Catalytically inactive sPLA2-IIA mutants retaines the ability to enhance cyclooxygenase-2 expression in connective tissue mast cells (7). Also inactivation of sPLA2-IIA by bromophenacyl bromide does not affect the ability of sPLA2-IIA to induce secretion of 0-glucuronidase, IL-6, and IL-8 from human eosinophils (8). It has thus been proposed that sPLA2-IIA action is mediated through interaction with specific receptors. Indeed the enzyme binds to a high affinity receptor of 180 kDa present on rabbit skeletal muscle (9). This so-called M (muscle)-type receptor belongs to the superfamily of C-type lectins and mediates some of the physiological effects of mammalian sPLA2-IIA, and binding of sPLA2-IIA to this receptor induces internalization of sPLA2-IIA (10). However, the interaction between sPLA2-IIA and the M-type receptor is species-specific, and human sPLA2-IIA binds to the human or mouse M-type receptor very weakly (11).

Integrins are a family of cell adhesion receptors that recognize ECM ligands and cell surface ligands (12). Integrins are transmembrane heterodimers, and at least 18 α and 8 β subunits are known (13). Integrins transduce signals to the cell upon ligand binding (12). The inventors previously reported that sPLA2-IIA binds to integrins αvβ3 and α4β1 and induces proliferative signals in an integrin-dependent manner. sPLA2-IIA specifically binds to integrin αvβ3 and α4β1 (14). The integrin-binding site does not include the catalytic center or the M-type receptor-binding site. WT and the catalytically inactive mutant (the H47Q mutant) of sPLA2-IIA induces intracellular signals in monocytic cells, but an integrin-binding defective mutant (the R74E/R100E mutant) does not (14). These results suggest that integrins may serve as receptors for sPLA2-IIA and mediate pro-inflammatory action of sPLA2-IIA in human. The inventors screened for small compounds that bind to sPLA-IIA and inhibit integrin binding and obtained several compounds and compound 21 (Cmpd21), which suppressed αvβ3-mediated cell adhesion and migration (15). These findings indicate direct binding of sPLA2-IIA to integrins is critical for pro-inflammatory actions of sPLA2-IIA.

It has been proposed that integrin activation is mediated by signaling from inside the cell (inside-out signaling), and that integrin activation is associated with global conformational changes of the integrin molecule (16,17). The inventors recently discovered that the chemokine domain of fractalkine (FKN-CD) directly binds to several integrins and this interaction is critical for fractalkine/CX3CR1 signaling (18). FKN-CD induces ternary complex formation (integrin-FKN-CD-CX3CR1) on the cell surface, suggesting that integrins act as co-receptor for FKN-CD in FKN/CX3CR1 signaling (18). Notably the inventors discovered that FKN-CD can activate integrins in the absence of CX3CR1 through direct binding to integrins probably in an allosteric mechanism (19). The inventors identified a new FKN-CDbinding site in integrins (site 2) that is distinct from the classical RGD-binding site (site 1). The position of site 2 was predicted by docking simulation of interaction between FKN-CD and integrin αvβ3 that has a closed-headpiece conformation. This is based on the premise that site 2 is open in the closed-headpiece αvβ3. A peptide from site 2 (residues 267-286 of 13) directly binds to FKN-CD and suppresses FKN-CD-induced integrin activation (19). The inventors thus proposed a model, in which FKN-CD binding to site 2 induces activation of site 1 though conformational changes (in an allosteric mechanism).

The site 2-mediated activation of integrins may not be limited to FKN-CD. In the present paper the inventors describe that sPLA2-IIA directly activates integrins (αvβ3, α4β1, and α5β1) in cell-free conditions and/or on the cell surface. sPLA2-IIA mutants that are catalytically inactive or defective in binding to M-type receptor still activate integrins, while the integrin-binding defective mutant did not. This suggests that direct integrin binding is required, but catalytic activity or M-type receptor is not. sPLA2-IIA is predicted to bind to site 2 in αvβ3 in a closed-headpiece conformation in docking simulation. Consistently, the inventors obtained evidence that a peptide from site 2 effectively suppressed the sPLA-IIA-induced integrin activation, suggesting that this activation involves the binding of sPLA-IIA to site 2. Cmpd21 effectively suppressed sPLA2-IIA-induced integrin activation. These results define a novel mechanism of pro-inflammatory action of sPLA2-IIA through integrin activation.

II. Recombinant Expression of Polypeptides

A. General Recombinant Technology

Basic texts disclosing general methods and techniques in the field of recombinant genetics include Sambrook and Russell, *Molecular Cloning, A Laboratory Manual* (3rd ed. 2001); Kriegler, Gene *Transfer and Expression: A Laboratory Manual* (1990); and Ausubel et al., eds., *Current Protocols in Molecular Biology* (1994).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage & Caruthers, *Tetrahedron Lett.* 22: 1859-1862 (1981), using an automated synthesizer, as described in Van Devanter et. al., *Nucleic Acids Res.* 12: 6159-6168 (1984). Purification of oligonucleotides is performed using any art-recognized strategy, e.g., native acrylamide gel electrophoresis or anion-exchange HPLC as described in Pearson & Reanier, *J. Chrom.* 255: 137-149 (1983).

The polynucleotide sequence encoding a polypeptide of interest, e.g., an integrin β fragment polypeptide, and synthetic oligonucleotides can be verified after cloning or subcloning using, e.g., the chain termination method for sequencing double-stranded templates of Wallace et al., *Gene* 16: 21-26 (1981).

B. Cloning and Subcloning of a Coding Sequence

The polynucleotide sequences encoding human integrin β1, β2, β3, and β4 are known as GenBank Accession No. X07979, AAA59490.1, J02703, and CAA36134.1, respectively. The corresponding amino acid sequences are GenBank Accession Nos. P05556, M15395, P05106, and X51841, respectively. These polynucleotide sequences may be obtained from a commercial supplier or by amplification methods such as polymerase chain reaction (PCR).

The rapid progress in the studies of human genome has made possible a cloning approach where a human DNA sequence database can be searched for any gene segment that has a certain percentage of sequence homology to a known nucleotide sequence. Any DNA sequence so identified can be subsequently obtained by chemical synthesis and/or PCR technique such as overlap extension method. For a short sequence, completely de novo synthesis may be sufficient; whereas further isolation of full length coding sequence from a human cDNA or genomic library using a synthetic probe may be necessary to obtain a larger gene.

Alternatively, a polynucleotide sequence encoding an integrin chain can be isolated from a cDNA or genomic DNA library using standard cloning techniques such as PCR, where homology-based primers can often be derived from a known nucleic acid sequence encoding an integrin polypeptide. This approach is particularly useful for identifying variants, orthologs, or homologs of integrin chains such as β1, β2, β3, and β4. Most commonly used techniques for this purpose are described in standard texts, e.g., Sambrook and Russell, supra.

cDNA libraries suitable for obtaining a coding sequence for a human integrin chain may be commercially available or can be constructed. The general methods of isolating mRNA, making cDNA by reverse transcription, ligating cDNA into a recombinant vector, transfecting into a recombinant host for propagation, screening, and cloning are well known (see, e.g., Gubler and Hoffman, *Gene,* 25: 263-269 (1983); Ausubel et al., supra). Upon obtaining an amplified segment of nucleotide sequence by PCR, the segment can be further used as a probe to isolate the full length polynucleotide sequence encoding the gene of interest (e.g., integrin β1 or β3 chain) from the cDNA library. A general description of appropriate procedures can be found in Sambrook and Russell, supra. A similar procedure can be followed to obtain a sequence encoding a human integrin chain from a human genomic library, which may be commercially available or can be constructed according to various art-recognized methods. Based on sequence homology, degenerate oligonucleotides can be designed as primer sets and PCR can be performed under suitable conditions (see, e.g., White et al., *PCR Protocols: Current Methods and Applications,* 1993; Griffin and Griffin, *PCR Technology*, CRC Press Inc. 1994) to amplify a segment of nucleotide sequence from a cDNA or genomic library.

Upon acquiring a polynucleotide sequence encoding an integrin β site-2 sequence, the sequence can then be subcloned into a vector, for instance, an expression vector, so that a recombinant polypeptide (e.g., an integrin β fragment) can be produced from the resulting construct. Further modifications to the coding sequence, e.g., nucleotide substitutions, may be subsequently made to alter the characteristics of the polypeptide.

C. Modification of a Polynucleotide Coding Sequence

The amino acid sequence of an integrin β fragment polypeptide may be modified while maintaining or enhancing the polypeptide's capability to inhibit endothelial cell proliferation, as determined by the in vitro or in vivo methods described below. Possible modifications to the amino acid sequence may include conservative substitutions; deletion or addition of one or more amino acid residues (e.g., addition at one terminal of the polypeptide of a tag sequence such as 6×His to facilitate purification or identification) at either or both of the N- and C-termini.

A variety of mutation-generating protocols are established and described in the art, and can be readily used to modify a polynucleotide sequence encoding an integrin β fragment polypeptide. See, e.g., Zhang et al., *Proc. Natl. Acad. Sci. USA,* 94: 4504-4509 (1997); and Stemmer, *Nature,* 370: 389-391 (1994). The procedures can be used separately or in combination to produce variants of a set of nucleic acids, and hence variants of encoded polypeptides. Kits for mutagenesis, library construction, and other diversity-generating methods are commercially available.

Mutational methods of generating diversity include, for example, site-directed mutagenesis (Botstein and Shortle, *Science,* 229: 1193-1201 (1985)), mutagenesis using uracil-containing templates (Kunkel, *Proc. Natl. Acad. Sci. USA,* 82: 488-492 (1985)), oligonucleotide-directed mutagenesis (Zoller and Smith, *Nucl. Acids Res.,* 10: 6487-6500 (1982)), phosphorothioate-modified DNA mutagenesis (Taylor et al., *Nucl. Acids Res.,* 13: 8749-8764 and 8765-8787 (1985)), and mutagenesis using gapped duplex DNA (Kramer et al., *Nucl. Acids Res.,* 12: 9441-9456 (1984)).

Other possible methods for generating mutations include point mismatch repair (Kramer et al., *Cell,* 38: 879-887 (1984)), mutagenesis using repair-deficient host strains (Carter et al., *Nucl. Acids Res.,* 13: 4431-4443 (1985)), deletion mutagenesis (Eghtedarzadeh and Henikoff, *Nucl. Acids Res.,* 14: 5115 (1986)), restriction-selection and restriction-purification (Wells et al., *Phil. Trans. R. Soc. Lond. A,* 317: 415-423 (1986)), mutagenesis by total gene synthesis (Nambiar et al., *Science,* 223: 1299-1301 (1984)), double-strand break repair (Mandecki, *Proc. Natl. Acad. Sci. USA,* 83: 7177-7181 (1986)), mutagenesis by polynucleotide chain termination methods (U.S. Pat. No. 5,965,408), and error-prone PCR (Leung et al., *Biotechniques,* 1: 11-15 (1989)).

D. Modification of Nucleic Acids for Preferred Codon Usage in a Host Organism

The polynucleotide sequence encoding an integrin β fragment can be further altered to coincide with the preferred codon usage of a particular host. For example, the preferred codon usage of one strain of bacterial cells can be used to derive a polynucleotide that encodes an integrin β fragment and includes the codons favored by this strain. The frequency of preferred codon usage exhibited by a host cell can be calculated by averaging frequency of preferred codon usage in a large number of genes expressed by the host cell (e.g., calculation service is available from web site of the Kazusa DNA Research Institute, Japan). This analysis is preferably limited to genes that are highly expressed by the host cell.

At the completion of modification, the coding sequences are verified by sequencing and are then subcloned into an appropriate expression vector for recombinant production of the integrin β fragment polypeptides.

E. Chemical Synthesis of Polypeptides

The amino acid sequences of human integrin β1, β2, β3, and β4 chains have been established (e.g., GenBank Accession Nos. P05556, M15395, P05106, and X51841, respectively). Polypeptides of known sequences, especially those of relatively short length such as an integrin β fragment, may be synthesized by solid-phase peptide synthesis methods using procedures similar to those described by Merrifield et al., *J. Am. Chem. Soc.,* 85:2149-2156 (1963); Barany and Merrifield, *Solid-Phase Peptide Synthesis, in The Peptides: Analysis, Synthesis, Biology* Gross and Meienhofer (eds.), Academic Press, N.Y., vol. 2, pp. 3-284 (1980); and Stewart et al., *Solid Phase Peptide Synthesis* 2nd ed., Pierce Chem. Co., Rockford, Ill. (1984). During synthesis, N-α-protected amino acids having protected side chains are added stepwise to a growing polypeptide chain linked by its C-terminal and to a solid support, i.e., polystyrene beads. The peptides are synthesized by linking an amino group of an N-α-deprotected amino acid to an α-carboxy group of an N-α-protected amino acid that has been activated by reacting it with a reagent such as dicyclohexylcarbodiimide. The attachment of a free amino group to the activated carboxyl leads to peptide bond formation. The most commonly used N-α-protecting groups include Boc, which is acid labile, and Fmoc, which is base labile.

Materials suitable for use as the solid support are well known to those of skill in the art and include, but are not limited to, the following: halomethyl resins, such as chloromethyl resin or bromomethyl resin; hydroxymethyl resins; phenol resins, such as 4-(α-[2,4-dimethoxyphenyl]-Fmoc-aminomethyl)phenoxy resin; tert-alkyloxycarbonyl-hydrazidated resins, and the like. Such resins are commercially available and their methods of preparation are known by those of ordinary skill in the art.

Briefly, the C-terminal N-α-protected amino acid is first attached to the solid support. The N-α-protecting group is then removed. The deprotected α-amino group is coupled to the activated α-carboxylate group of the next N-α-protected amino acid. The process is repeated until the desired peptide is synthesized. The resulting peptides are then cleaved from the insoluble polymer support and the amino acid side chains deprotected. Longer peptides can be derived by condensation of protected peptide fragments. Details of appropriate chemistries, resins, protecting groups, protected amino acids and reagents are well known in the art and so are not discussed in detail herein (See, Atherton et al., *Solid Phase Peptide Synthesis: A Practical Approach*, IRL Press (1989), and Bodanszky, *Peptide Chemistry, A Practical Textbook*, 2nd Ed., Springer-Verlag (1993)).

III. Expression and Purification of Recombinant Polypeptides

Following verification of the coding sequence, a polypeptide of interest (e.g., an integrin β fragment) can be produced using routine techniques in the field of recombinant genetics, relying on the polynucleotide sequences encoding the polypeptide disclosed herein.

A. Expression Systems

To obtain high level expression of a nucleic acid encoding a polypeptide of interest, one typically subclones the polynucleotide coding sequence into an expression vector that contains a strong promoter to direct transcription, a transcription/translation terminator and a ribosome binding site for translational initiation. Suitable bacterial promoters are well known in the art and described, e.g., in Sambrook and Russell, supra, and Ausubel et al., supra. Bacterial expression systems for expressing the sPLA2-IIA or integrin polypeptide are available in, e.g., *E. coli, Bacillus* sp., *Salmonella,* and *Caulobacter.* Kits for such expression systems are commercially available. Eukaryotic expression systems for mammalian cells, yeast, and insect cells are well known in the art and are also commercially available. In one embodiment, the eukaryotic expression vector is an adenoviral vector, an adeno-associated vector, or a retroviral vector.

The promoter used to direct expression of a heterologous nucleic acid depends on the particular application. The promoter is optionally positioned about the same distance from the heterologous transcription start site as it is from the transcription start site in its natural setting. As is known in the art, however, some variation in this distance can be accommodated without loss of promoter function.

In addition to the promoter, the expression vector typically includes a transcription unit or expression cassette that contains all the additional elements required for the expression of the desired polypeptide in host cells. A typical expression cassette thus contains a promoter operably linked to the nucleic acid sequence encoding the polypeptide and signals required for efficient polyadenylation of the transcript, ribosome binding sites, and translation termination. The nucleic acid sequence encoding the desired polypeptide is typically linked to a cleavable signal peptide sequence to promote secretion of the recombinant polypeptide by the transformed cell. Such signal peptides include, among others, the signal peptides from tissue plasminogen activator, insulin, and neuron growth factor, and juvenile hormone esterase of Heliothis virescens. If, however, a recombinant polypeptide (such as an integrin β fragment) is intended to be expressed on the host cell surface, an appropriate anchoring sequence is used in concert with the coding sequence. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A$^+$, pMTO10/A$^+$, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as a baculovirus vector in insect cells, with a polynucleotide sequence encoding the desired polypeptide under the direction of the polyhedrin promoter or other strong baculovirus promoters.

The elements that are typically included in expression vectors also include a replicon that functions in E. coli, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are optionally chosen such that they do not interfere with the replication of the DNA in eukaryotic cells, if necessary. Similar to antibiotic resistance selection markers, metabolic selection markers based on known metabolic pathways may also be used as a means for selecting transformed host cells.

When periplasmic expression of a recombinant protein (e.g., an integrin β fragment) is desired, the expression vector further comprises a sequence encoding a secretion signal, such as the E. coli OppA (Periplasmic Oligopeptide Binding Protein) secretion signal or a modified version thereof, which is directly connected to 5' of the coding sequence of the protein to be expressed. This signal sequence directs the recombinant protein produced in cytoplasm through the cell membrane into the periplasmic space. The expression vector may further comprise a coding sequence for signal peptidase 1, which is capable of enzymatically cleaving the signal sequence when the recombinant protein is entering the periplasmic space. More detailed description for periplasmic production of a recombinant protein can be found in, e.g., Gray et al., Gene 39: 247-254 (1985), U.S. Pat. Nos. 6,160,089 and 6,436,674.

As discussed above, a person skilled in the art will recognize that various conservative substitutions can be made to an integrin β fragment or its coding sequence while still retaining the biological activity of the polypeptide, e.g., the ability to transduce pro-inflammatory signals. Moreover, modifications of a polynucleotide coding sequence may also be made to accommodate preferred codon usage in a particular expression host without altering the resulting amino acid sequence.

B. Transfection Methods

Standard transfection methods are used to produce bacterial, mammalian, yeast, insect, or plant cell lines that express large quantities of a recombinant polypeptide, which are then purified using standard techniques (see, e.g., Colley et al., J. Biol. Chem. 264: 17619-17622 (1989); Guide to Protein Purification, in Methods in Enzymology, vol. 182 (Deutscher, ed., 1990)). Transformation of eukaryotic and prokaryotic cells are performed according to standard techniques (see, e.g., Morrison, J. Bact. 132: 349-351 (1977); Clark-Curtiss & Curtiss, Methods in Enzymology 101: 347-362 (Wu et al., eds, 1983).

Any of the well-known procedures for introducing foreign nucleotide sequences into host cells may be used. These include the use of calcium phosphate transfection, polybrene, protoplast fusion, electroporation, liposomes, microinjection, plasma vectors, viral vectors and any of the other well-known methods for introducing cloned genomic DNA, cDNA, synthetic DNA, or other foreign genetic material into a host cell (see, e.g., Sambrook and Russell, supra). It is only necessary that the particular genetic engineering procedure used be capable of successfully introducing at least one gene into the host cell capable of expressing the recombinant polypeptide.

C. Purification of Recombinantly Produced Polypeptides

Once the expression of a recombinant polypeptide in transfected host cells is confirmed, e.g., by an immunological assay, the host cells are then cultured in an appropriate scale for the purpose of purifying the recombinant polypeptide.

1. Purification of Recombinantly Produced Polypeptide from Bacteria

When desired polypeptides are produced recombinantly by transformed bacteria in large amounts, typically after promoter induction, although expression can be constitutive, the polypeptides may form insoluble aggregates. There are several protocols that are suitable for purification of protein inclusion bodies. For example, purification of aggregate proteins (hereinafter referred to as inclusion bodies) typically involves the extraction, separation and/or purification of inclusion bodies by disruption of bacterial cells, e.g., by incubation in a buffer of about 100-150 µg/ml lysozyme and 0.1% Nonidet P40, a non-ionic detergent. The cell suspension can be ground using a Polytron grinder (Brinkman Instruments, Westbury, N.Y.). Alternatively, the cells can be sonicated on ice. Alternate methods of lysing bacteria are described in Ausubel et al. and Sambrook and Russell, both supra, and will be apparent to those of skill in the art.

The cell suspension is generally centrifuged and the pellet containing the inclusion bodies resuspended in buffer which does not dissolve but washes the inclusion bodies, e.g., 20 mM Tris-HCl (pH 7.2), 1 mM EDTA, 150 mM NaCl and 2% Triton-X 100, a non-ionic detergent. It may be necessary to repeat the wash step to remove as much cellular debris as possible. The remaining pellet of inclusion bodies may be resuspended in an appropriate buffer (e.g., 20 mM sodium phosphate, pH 6.8, 150 mM NaCl). Other appropriate buffers will be apparent to those of skill in the art.

Following the washing step, the inclusion bodies are solubilized by the addition of a solvent that is both a strong hydrogen acceptor and a strong hydrogen donor (or a combination of solvents each having one of these properties). The proteins that formed the inclusion bodies may then be renatured by dilution or dialysis with a compatible buffer. Suitable solvents include, but are not limited to, urea (from about 4 M to about 8 M), formamide (at least about 80%, volume/volume basis), and guanidine hydrochloride (from about 4 M to about 8 M). Some solvents that are capable of solubilizing aggregate-forming proteins, such as SDS (sodium dodecyl sulfate) and 70% formic acid, may be inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of the immunologically and/or biologically active protein of interest. After solubilization, the protein can be separated from other bacterial proteins by standard separation techniques. For further description of purifying recombinant polypeptides from bacterial inclusion body, see, e.g., Patra et al., *Protein Expression and Purification* 18: 182-190 (2000).

Alternatively, it is possible to purify recombinant polypeptides from bacterial periplasm. Where the recombinant protein is exported into the periplasm of the bacteria, the periplasmic fraction of the bacteria can be isolated by cold osmotic shock in addition to other methods known to those of skill in the art (see e.g., Ausubel et al., supra). To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

2. Standard Protein Separation Techniques for Purification

When a recombinant polypeptide is expressed in host cells in a soluble form, its purification can follow the standard protein purification procedure described below. This standard purification procedure is also suitable for purifying polypeptides obtained from chemical synthesis (e.g., an integrin β fragment).

i. Solubility Fractionation

Often as an initial step, and if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol is to add saturated ammonium sulfate to a protein solution so that the resultant ammonium sulfate concentration is between 20-30%. This will precipitate the most hydrophobic proteins. The precipitate is discarded (unless the protein of interest is hydrophobic) and ammonium sulfate is added to the supernatant to a concentration known to precipitate the protein of interest. The precipitate is then solubilized in buffer and the excess salt removed if necessary, through either dialysis or diafiltration. Other methods that rely on solubility of proteins, such as cold ethanol precipitation, are well known to those of skill in the art and can be used to fractionate complex protein mixtures.

ii. Size Differential Filtration

Based on a calculated molecular weight, a protein of greater and lesser size can be isolated using ultrafiltration through membranes of different pore sizes (for example, Amicon or Millipore membranes). As a first step, the protein mixture is ultrafiltered through a membrane with a pore size that has a lower molecular weight cut-off than the molecular weight of a protein of interest, e.g., an integrin β fragment polypeptide. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

iii. Column Chromatography

The proteins of interest (such as an integrin β fragment) can also be separated from other proteins on the basis of their size, net surface charge, hydrophobicity, or affinity for ligands. In addition, antibodies raised against an integrin β fragment can be conjugated to column matrices and the corresponding polypeptide immunopurified. All of these methods are well known in the art.

It will be apparent to one of skill that chromatographic techniques can be performed at any scale and using equipment from many different manufacturers (e.g., Pharmacia Biotech).

IV. Inhibitors of sPLA2-IIA and Integrin Binding

A. Inhibitory Nucleic Acids

Inhibition of sPLA2-IIA or integrin gene expression can be achieved through the use of inhibitory nucleic acids. Inhibitory nucleic acids can be single-stranded nucleic acids or oligonucleotides that can specifically bind to a complementary nucleic acid sequence. By binding to the appropriate target sequence, an RNA-RNA, a DNA-DNA, or RNA-DNA duplex or triplex is formed. These nucleic acids are often termed "antisense" because they are usually complementary to the sense or coding strand of the gene, although recently approaches for use of "sense" nucleic acids have also been developed. The term "inhibitory nucleic acids" as used herein, refers to both "sense" and "antisense" nucleic acids. In addition, inhibition of sPLA2-IIA-integrin binding can be achieved by administration of a nucleic acid encoding and directing the expression of an integrin β fragment.

In one embodiment, the inhibitory nucleic acid can specifically bind to a target sPLA2-IIA or integrin polynucleotide. Administration of such inhibitory nucleic acids can inhibit undesired inflammatory responses by reducing or eliminating the effects of sPLA2-IIA-integrin binding and its downstream signals. Nucleotide sequences encoding sPLA2-IIA and integrin α and β chains are known for several species, including the human cDNA. One can derive a suitable inhibitory nucleic acid from the human sPLA2-IIA or integrin α or β chain, and their polymorphic variants or interspecies orthologs/homologs.

By binding to the target nucleic acid, the inhibitory nucleic acid can inhibit the function of the target nucleic acid. This could, for example, be a result of blocking DNA transcription, processing or poly(A) addition to mRNA, DNA replication, translation, or promoting inhibitory mechanisms of the cells, such as promoting RNA degradation. Inhibitory nucleic acid methods therefore encompass a number of different approaches to altering expression of specific genes that operate by different mechanisms. These different types of inhibitory nucleic acid technology are described in Helene and Toulme, *Biochim. Biophys. Acta.*, 1049:99-125 (1990).

Inhibitory nucleic acid therapy approaches can be classified into those that target DNA sequences, those that target RNA sequences (including pre-mRNA and mRNA), those that target proteins (sense strand approaches), and those that cause cleavage or chemical modification of the target nucleic acids.

Approaches targeting DNA fall into several categories. Nucleic acids can be designed to bind to the major groove of the duplex DNA to form a triple helical or "triplex" structure. Alternatively, inhibitory nucleic acids are designed to bind to regions of single stranded DNA resulting from the opening of the duplex DNA during replication or transcription. See Helene and Toulme, supra.

More commonly, inhibitory nucleic acids are designed to bind to mRNA or mRNA precursors. Inhibitory nucleic acids are used to prevent maturation of pre-mRNA. Inhibitory nucleic acids may be designed to interfere with RNA processing, splicing or translation. The inhibitory nucleic acids are often targeted to mRNA. In this approach, the inhibitory nucleic acids are designed to specifically block translation of the encoded protein. Using this approach, the inhibitory nucleic acid can be used to selectively suppress certain cellular functions by inhibition of translation of mRNA encoding critical proteins. For example, an inhibitory antisense nucleic acid complementary to regions of a target mRNA inhibits protein expression (see, e.g., Wickstrom et al., *Proc. Nat'l. Acad. Sci.* USA, 85:1028-1032 (1988); and Harel-Bellan et al., *Exp. Med.*, 168:2309-2318 (1988)). As described in Helene and Toulme, supra, inhibitory nucleic acids targeting mRNA have been shown to work by several different mechanisms in order to inhibit translation of the encoded protein(s).

The inhibitory nucleic acids introduced into the cell can also encompass the "sense" strand of the gene or mRNA to trap or compete for the enzymes or binding proteins involved in mRNA translation. See Helene and Toulme, supra.

The inhibitory nucleic acids can also be used to induce chemical inactivation or cleavage of the target genes or mRNA. Chemical inactivation can occur by the induction of crosslinks between the inhibitory nucleic acid and the target nucleic acid within the cell. Alternatively, irreversible photochemical reactions can be induced in the target nucleic acid by means of a photoactive group attached to the inhibitory nucleic acid. Other chemical modifications of the target nucleic acids induced by appropriately derivatized inhibitory nucleic acids may also be used.

Cleavage, and therefore inactivation, of the target nucleic acids can be affected by attaching to the inhibitory nucleic acid a substituent that can be activated to induce cleavage reactions. The substituent can be one that affects either chemical, photochemical or enzymatic cleavage. For example, one can contact an mRNA:antisense oligonucleotide hybrid with a nuclease which digests mRNA:DNA hybrids. Alternatively cleavage can be induced by the use of ribozymes or catalytic RNA. In this approach, the inhibitory nucleic acids would comprise either naturally occurring RNA (ribozymes) or synthetic nucleic acids with catalytic activity.

Inhibitory nucleic acids can also include RNA aptamers, which are short, synthetic oligonucleotide sequences that bind to proteins (see, e.g., Li et al., *Nuc. Acids Res.*, 34:6416-24 (2006)). They are notable for both high affinity and specificity for the targeted molecule, and have the additional advantage of being smaller than antibodies (usually less than 6 kD). RNA aptamers with a desired specificity are generally selected from a combinatorial library, and can be modified to reduce vulnerability to ribonucleases, using methods known in the art.

B. Inactivating Antibodies

Inhibition of signal transduction by sPLA2-IIA and integrin binding can be achieved with an inactivating antibody. An inactivating antibody can comprise an antibody or antibody fragment that specifically binds to any one of sPLA2-IIA and integrin α and β chains and subsequently abolishes or reduces the binding between sPLA2-IIA and integrin. Inactivating antibody fragments include, e.g., Fab fragments, heavy or light chain variable regions, single complementary determining regions (CDRs), or combinations of CRDs with the desired target protein binding activity. An inactivating antibody for sPLA2-IIA-integrin binding can be a naturally occurring antibody derived from any appropriate organism, e.g., mouse, rat, rabbit, gibbon, goat, horse, sheep, etc., or an artificial antibody such as a single chain antibody (scFv), a chimeric antibody, or a humanized antibody.

The chimeric antibodies of the invention may be monovalent, divalent, or polyvalent immunoglobulins. For example, a monovalent chimeric antibody is a dimer (HL) formed by a chimeric H chain associated through disulfide bridges with a chimeric L chain, as noted above. A divalent chimeric antibody is a tetramer ($H_2 L_2$) formed by two HL dimers associated through at least one disulfide bridge. A polyvalent chimeric antibody is based on an aggregation of chains.

C. Identification of sPLA2-IIA and Integrin Binding Inhibitors

One can identify compounds that are effective inhibitors of sPLA2-IIA and integrin binding by screening a variety of compounds and mixtures of compounds for their ability to suppress the binding between sPLA2-IIA and an integrin β fragment comprising an site-2 sequence. The testing can be performed in a cell-based system or in a cell-free system, using either the full length sequence of the sPLA2-IIA and an integrin β fragment, or a minimal region or subsequence of sPLA2-IIA (which is sufficient to support the specific binding between sPLA2-IIA and integrin β) and an integrin β fragment.

One aspect of the present invention is directed to methods for screening compounds that have the activity to inhibit sPLA2-IIA specific binding with integrin β at the site-2 of integrin β. Such compounds can be in the form of a mixture of suitable inhibitors, or each in substantially isolated form. An example of an in vitro binding assay can comprise an sPLA2-IIA polypeptide and an integrin β fragment, where the level of sPLA2-IIA binding to the integrin β fragment is determined in the presence or absence of a test compound. Optionally, one of the sPLA2-IIA or the an integrin β fragment is immobilized to a solid substrate or support. A detectable label, e.g., a radioactive or fluorescent label, can be provided for sPLA2-IIA or the integrin β fragment, either directly or indirectly (through a second molecule that specifically recognizes sPLA2-IIA or the integrin β fragment), to facilitate detection of sPLA2-IIA and integrin binding.

Another typical binding assay comprises cells expressing an integrin β fragment on their surface and a free sPLA2-IIA polypeptide, where the level of sPLA2-IIA binding to the integrin β fragment is determined in the presence or absence of a test compound. Suitable cells include any cultured cells such as mammalian, insect, microbial (e.g., bacterial, yeast, fungal), or plant cells. In some embodiments, the cells recombinantly express the integrin β fragment. In this type of cell-based system, the level of sPLA2-IIA binding to the integrin β fragment can be determined directly by measuring the binding.

In some embodiments, the assays are designed to screen large chemical libraries by automating the assay steps and providing compounds from any convenient source to assays, which are typically run in parallel (e.g., in microtiter formats on microtiter plates in robotic assays).

In these screening assays it is optional to have positive controls to ensure that the components of the assays are performing properly. For example, a known inhibitor of sPLA2-IIA and integrin binding can be incubated with one sample of the assay, and the resulting change in signal determined according to the methods herein.

Essentially any chemical compound can be tested as a potential inhibitor of sPLA2-IIA and integrin binding by using methods of the present invention. Most preferred are generally compounds that can be dissolved in aqueous or organic (especially DMSO-based) solutions are used. It will be appreciated that there are many suppliers of chemical compounds, such as Sigma (St. Louis, Mo.), Aldrich (St. Louis, Mo.), Sigma-Aldrich (St. Louis, Mo.), and Fluka Chemika-Biochemica Analytika (Buchs, Switzerland).

Inhibitors of sPLA2-IIA and integrin binding can be identified by screening a combinatorial library containing a large number of potential therapeutic compounds (potential modulator compounds). Such "combinatorial chemical libraries" can be screened in one or more assays, as described herein, to identify those library members (particular chemical species or subclasses) that display a desired characteristic activity. The compounds thus identified can serve as conventional "lead compounds" subject to modification and further testing or can be directly used as potential or actual therapeutics.

Preparation and screening of combinatorial chemical libraries are well known to those of skill in the art. Such combinatorial chemical libraries include, but are not limited to, peptide libraries (see, e.g., U.S. Pat. No. 5,010,175; Furka, *Int. J. Pept. Prot. Res.*, 37:487-493 (1991); and Houghton et al., *Nature*, 354:84-88 (1991)) and carbohydrate libraries (see, e.g., Liang et al., *Science*, 274:1520-1522 (1996); and U.S. Pat. No. 5,593,853). Other chemistries for generating chemical diversity libraries can also be used. Such chemistries include, but are not limited to: peptoids (PCT Pub. No. WO 91/19735); encoded peptides (PCT Pub. No. WO 93/20242); random bio-oligomers (PCT Pub. No. WO 92/00091); benzodiazepines (U.S. Pat. No. 5,288,514); diversomers, such as hydantoins, benzodiazepines and dipeptides (Hobbs et al., *Proc. Nat. Acad. Sci. USA*, 90:6909-6913 (1993)); vinylogous polypeptides (Hagihara et al., *J. Amer. Chem. Soc.*, 114:6568 (1992)); nonpeptidal peptidomimetics with β-D-glucose scaffolding (Hirschmann et al., *J Amer. Chem. Soc.*, 114:9217-9218 (1992)); analogous organic syntheses of small compound libraries (Chen et al., *J. Amer. Chem. Soc.*, 116:2661 (1994)); oligocarbamates (Cho et al., *Science*, 261:1303 (1993)); and/or peptidyl phosphonates (Campbell et al., *J. Org. Chem.*, 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), small organic molecule libraries (see, e.g., benzodiazepines, Baum C&EN, January 18, page 33 (1993); isoprenoids (U.S. Pat. No. 5,569,588); thiazolidinones and metathiazanones (U.S. Pat. No. 5,549,974); pyrrolidines (U.S. Pat. Nos. 5,525,735 and 5,519,134); morpholino compounds (U.S. Pat. No. 5,506,337); and benzodiazepines (U.S. Pat. No. 5,288,514)).

Alternatively, one can identify compounds that are suitable inhibitors of sPLA2-IIA and integrin specific binding by screening a variety of compounds and mixtures of compounds for their ability to suppress sPLA2-IIA or integrin α or β chain expression. Methods of detecting expression levels are well known in the art, and include both protein- and nucleic acid-based methods.

For example, a test agent can be contacted in vitro with cells expressing sPLA2-IIA. An agent that inhibits sPLA2-IIA expression is one that results in a decrease in the level of sPLA2-IIA polypeptide or transcript, as measured by any appropriate assay common in the art (e.g., Northern blot, RT-PCR, Western blot, or other hybridization or affinity assays), when compared to expression without the test agent. In some embodiments, a test nucleic acid inhibitor can be introduced into a cell, e.g., using standard transfection or transduction techniques, and the level of sPLA2-IIA expression detected. A typical decrease is a reduction in the expression level by at least 10%, or higher (e.g., at least 20%, 30%, 50%, 75%, 80%, or 90%) compared the level of expression in the absence of the test inhibitor.

V. Conditions Involving Inflammatory Responses and Cell Proliferation

Identification and diagnosis of conditions involving inflammation or undesirable cell proliferation, as well as methods of monitoring the effectiveness of a therapeutic regimen as described herein, are included in the present invention. As explained above, inflammation is generally characterized by redness, swelling, pain, and occasional loss of function. However, symptoms vary among tissues, so that some inflammatory conditions are not easily detectable (e.g., atherosclerosis). Undesirable cell proliferation, on the other hand, is often determined by way of detecting a benign or malignant growth, including an abnormal expansion of a particular cell or tissue type, such as various types of tumors and cancers.

Although the inflammatory response can play a role in the healing process by destroying, diluting, and isolating injurious agents and stimulating repair of the affected tissue, inflammatory responses can also be harmful. For example, inflammation results in leakage of plasma from the blood vessels. Although this leakage can have beneficial effects, it causes pain and when uncontrolled can lead to loss of function and death (such as adult respiratory distress syndrome). Anaphylactic shock, arthritis, and gout are among the conditions that are characterized by uncontrolled or inappropriate inflammation.

On a cellular level, an inflammatory response is typically initiated by endothelial cells producing molecules that attract and detain inflammatory cells (e.g., myeloid cells such as neutrophils, eosinophils, and basophils) at the site of injury or irritation. The inflammatory cells then are transported through the endothelial barrier into the surrounding tissue. The result is accumulation of inflammatory cells, in particular neutrophils. Such accumulation is easily detectable by one of skill.

Adaptive immune cells (T and B cells) are often involved in inflammatory conditions. These cells release cytokines and antibodies in response to the source of the irritation. Thus, an inflammatory response can also be detected by detecting a change in the level of inflammatory cytokines, e.g., in a localized region of irritation or in the serum or plasma of an individual. It will be appreciated by those of skill in the art that each of these symptoms can be detected in an individual for the purposes of diagnosis. Further, a subject undergoing therapy for an inflammatory condition can be monitored, for instance, by detecting any changes in severity of the symptoms. Such inflammatory conditions include rheumatoid arthritis, Alzheimer's disease, multiple sclerosis, and atherosclerosis.

VI. Pharmaceutical Compositions and Administration

The present invention also provides pharmaceutical compositions comprising an effective amount of an inhibitor of sPLA2-IIA and integrin binding for inhibiting a pro-inflammatory signal or a pro-proliferation signal, therefore useful in both prophylactic and therapeutic applications designed for various diseases and conditions involving undesired inflammation and/or cell proliferation. Pharmaceutical compositions of the invention are suitable for use in a variety of drug delivery systems. Suitable formulations for use in the present invention are found in *Remington's Pharmaceutical Sciences*, Mack Publishing Company, Philadelphia, Pa., 17th ed. (1985). For a brief review of methods for drug delivery, see, Langer, *Science* 249: 1527-1533 (1990).

The pharmaceutical compositions of the present invention can be administered by various routes, e.g., oral, subcutaneous, transdermal, intramuscular, intravenous, or intraperitoneal. The routes of administering the pharmaceutical compositions include systemic or local delivery to a subject suffering from a condition exacerbated by inflammation at daily doses of about 0.01-5000 mg, preferably 5-500 mg, of an inhibitor of sPLA2-IIA-integrin binding for a 70 kg adult human per day. The appropriate dose may be administered in a single daily dose or as divided doses presented at appropriate intervals, for example as two, three, four, or more subdoses per day.

For preparing pharmaceutical compositions containing an inhibitor of sPLA2-IIA-integrin binding, inert and pharmaceutically acceptable carriers are used. The pharmaceutical carrier can be either solid or liquid. Solid form preparations include, for example, powders, tablets, dispersible granules, capsules, cachets, and suppositories. A solid carrier can be one or more substances that can also act as diluents, flavoring agents, solubilizers, lubricants, suspending agents, binders, or tablet disintegrating agents; it can also be an encapsulating material.

In powders, the carrier is generally a finely divided solid that is in a mixture with the finely divided active component, e.g., an inhibitor of sPLA2-IIA and integrin binding. In tablets, the active ingredient (the inhibitor) is mixed with the carrier having the necessary binding properties in suitable proportions and compacted in the shape and size desired.

For preparing pharmaceutical compositions in the form of suppositories, a low-melting wax such as a mixture of fatty acid glycerides and cocoa butter is first melted and the active ingredient is dispersed therein by, for example, stirring. The molten homogeneous mixture is then poured into convenient-sized molds and allowed to cool and solidify.

Powders and tablets preferably contain between about 5% to about 70% by weight of the active ingredient. Suitable carriers include, for example, magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The pharmaceutical compositions can include the formulation of the active compound of an sPLA2-IIA-integrin binding inhibitor with encapsulating material as a carrier providing a capsule in which the inhibitor (with or without other carriers) is surrounded by the carrier, such that the carrier is thus in association with the compound. In a similar manner, cachets can also be included. Tablets, powders, cachets, and capsules can be used as solid dosage forms suitable for oral administration.

Liquid pharmaceutical compositions include, for example, solutions suitable for oral or parenteral administration, suspensions, and emulsions suitable for oral administration. Sterile water solutions of the active component (e.g., an inhibitor of sPLA2-IIA and integrin binding) or sterile solutions of the active component in solvents comprising water, buffered water, saline, PBS, ethanol, or propylene glycol are examples of liquid compositions suitable for parenteral administration. The compositions may contain pharmaceutically acceptable auxiliary substances as required to approximate physiological conditions, such as pH adjusting and buffering agents, tonicity adjusting agents, wetting agents, detergents, and the like.

Sterile solutions can be prepared by dissolving the active component (e.g., an inhibitor of sPLA2-IIA and integrin binding) in the desired solvent system, and then passing the resulting solution through a membrane filter to sterilize it or, alternatively, by dissolving the sterile compound in a previously sterilized solvent under sterile conditions. The resulting aqueous solutions may be packaged for use as is, or lyophilized, the lyophilized preparation being combined with a sterile aqueous carrier prior to administration. The pH of the preparations typically will be between 3 and 11, more preferably from 5 to 9, and most preferably from 7 to 8.

The pharmaceutical compositions containing the inhibitor can be administered for prophylactic and/or therapeutic treatments. In therapeutic applications, compositions are administered to a patient already suffering from a condition that may be exacerbated by an undesirable inflammatory reaction in an amount sufficient to prevent, cure, reverse, or at least partially slow or arrest the symptoms of the condition and its complications. An amount adequate to accomplish this is defined as a "therapeutically effective dose." Amounts effective for this use will depend on the severity of the disease or condition and the weight and general state of the patient, but generally range from about 0.1 mg to about 2,000 mg of the inhibitor per day for a 70 kg patient, with dosages of from about 5 mg to about 500 mg of the inhibitor per day for a 70 kg patient being more commonly used.

In prophylactic applications, pharmaceutical compositions containing an inhibitor of sPLA2-IIA-integrin binding are administered to a patient susceptible to or otherwise at risk of developing a disease or condition involving an undesirable inflammatory response and/or undesirable cell proliferation in an amount sufficient to delay or prevent the onset of the symptoms. Such an amount is defined to be a "prophylactically effective dose." In this use, the precise amounts of the inhibitor again depend on the patient's state of health and weight, but generally range from about 0.1 mg to about 2,000 mg of the inhibitor for a 70 kg patient per day, more commonly from about 5 mg to about 500 mg for a 70 kg patient per day.

Single or multiple administrations of the compositions can be carried out with dose levels and pattern being selected by the treating physician. In any event, the pharmaceutical formulations should provide a quantity of a compound sufficient to effectively inhibit the undesirable inflammatory response mediated by sPLA2-integrin binding in the patient, either therapeutically or prophylactically.

VII. Therapeutic Applications Using Nucleic Acids

A variety of inflammatory conditions or undesirable cell proliferation can be treated by therapeutic approaches that involve introducing into a cell an inhibitory nucleic acid encoding an inhibitor of sPLA2-IIA and integrin binding (e.g., an integrin β fragment) such that the expression of the inhibitor leads to reduced or abolished sPLA2-IIA-integrin binding in the cell. Those amenable to treatment by this approach include a broad spectrum of conditions involving undesirable inflammation and/or cell proliferation. For discussions on the application of gene therapy towards the treatment of genetic as well as acquired diseases, see, Miller Nature 357:455-460 (1992); and Mulligan Science 260:926-932 (1993).

A. Vectors for Nucleic Acid Delivery

For delivery to a cell or organism, an inhibitory nucleic acid of the invention can be incorporated into a vector. Examples of vectors used for such purposes include expression plasmids capable of directing the expression of the inhibitors in the target cell. In other instances, the vector is a viral vector system wherein the polynucleotide is incorporated into a viral genome that is capable of transfecting the target cell. In a preferred embodiment, the inhibitory nucleic acid can be operably linked to expression and control sequences that can direct transcription of sequence in the desired target host cells. Thus, one can achieve reduced binding of sPLA2-IIA and integrin under appropriate conditions in the target cell.

B. Gene Delivery Systems

As used herein, "gene delivery system" refers to any means for the delivery of an inhibitory nucleic acid of the invention to a target cell. Viral vector systems useful in the introduction and expression of an inhibitory nucleic acid include, for example, naturally occurring or recombinant viral vector systems. Depending upon the particular application, suitable viral vectors include replication competent, replication deficient, and conditionally replicating viral vectors. For example, viral vectors can be derived from the genome of human or bovine adenoviruses, vaccinia virus, herpes virus, adeno-associated virus, minute virus of mice (MVM), HIV, sindbis virus, and retroviruses (including but not limited to Rous sarcoma virus), and MoMLV. Typically, the inhibitory nucleic acid is inserted into such vectors to allow packaging of the gene construct, typically with accompanying viral DNA, followed by infection of a sensitive host cell and expression of the gene of interest.

Similarly, viral envelopes used for packaging gene constructs that include the inhibitory nucleic acid can be modified by the addition of receptor ligands or antibodies specific for a receptor to permit receptor-mediated endocytosis into specific cells (see, e.g., WO 93/20221, WO 93/14188, and WO 94/06923).

Retroviral vectors may also be useful for introducing the inhibitory nucleic acid of the invention into target cells or organisms. Retroviral vectors are produced by genetically manipulating retroviruses. The viral genome of retroviruses is RNA. Upon infection, this genomic RNA is reverse transcribed into a DNA copy which is integrated into the chromosomal DNA of transduced cells with a high degree of stability and efficiency. The integrated DNA copy is referred to as a provirus and is inherited by daughter cells as is any other gene. The wild type retroviral genome and the proviral DNA have three genes: the gag, the pol and the env genes, which are flanked by two long terminal repeat (LTR) sequences. The gag gene encodes the internal structural (nucleocapsid) proteins; the pol gene encodes the RNA directed DNA polymerase (reverse transcriptase); and the env gene encodes viral envelope glycoproteins. The 5' and 3' LTRs serve to promote transcription and polyadenylation of virion RNAs. Adjacent to the 5' LTR are sequences necessary for reverse transcription of the genome (the tRNA primer binding site) and for efficient encapsulation of viral RNA into particles (the Psi site) (see, Mulligan, In: Experimental Manipulation of Gene Expression, Inouye (ed), 155-173 (1983); Mann et al., Cell 33:153-159 (1983); Cone and Mulligan, Proceedings of the National Academy of Sciences, U.S.A., 81:6349-6353 (1984)).

The design of retroviral vectors is well known to those of ordinary skill in the art. In brief, if the sequences necessary for encapsidation (or packaging of retroviral RNA into infectious virions) are missing from the viral genome, the result is a cis acting defect which prevents encapsidation of genomic RNA. However, the resulting mutant is still capable of directing the synthesis of all virion proteins. Retroviral genomes from which these sequences have been deleted, as well as cell lines containing the mutant genome stably integrated into the chromosome are well known in the art and are used to construct retroviral vectors. Preparation of retroviral vectors and their uses are described in many publications including, e.g., European Patent Application EPA 0 178 220; U.S. Pat. No. 4,405,712, Gilboa Biotechniques 4:504-512 (1986); Mann et al., Cell 33:153-159 (1983); Cone and Mulligan Proc. Natl. Acad. Sci. USA 81:6349-6353 (1984); Eglitis et al. Biotechniques 6:608-614 (1988); Miller et al. Biotechniques 7:981-990 (1989); Miller (1992) supra; Mulligan (1993), supra; and WO 92/07943.

The retroviral vector particles are prepared by recombinantly inserting the desired inhibitory nucleic acid sequence into a retrovirus vector and packaging the vector with retroviral capsid proteins by use of a packaging cell line. The resultant retroviral vector particle is incapable of replication in the host cell but is capable of integrating into the host cell genome as a proviral sequence containing the desired nucleotide sequence. As a result, the patient is capable of producing, for example, the inhibitory nucleic acid, thus eliminating or reducing unwanted inflammatory conditions.

Packaging cell lines that are used to prepare the retroviral vector particles are typically recombinant mammalian tissue culture cell lines that produce the necessary viral structural proteins required for packaging, but which are incapable of producing infectious virions. The defective retroviral vectors that are used, on the other hand, lack these structural genes but encode the remaining proteins necessary for packaging. To prepare a packaging cell line, one can construct an infectious clone of a desired retrovirus in which the packaging site has been deleted. Cells comprising this construct will express all structural viral proteins, but the introduced DNA will be incapable of being packaged. Alternatively, packaging cell lines can be produced by transforming a cell line with one or more expression plasmids encoding the appropriate core and envelope proteins. In these cells, the gag, pol, and env genes can be derived from the same or different retroviruses.

A number of packaging cell lines suitable for the present invention are also available in the prior art. Examples of these cell lines include Crip, GPE86, PA317 and PG13 (see Miller et al., *J. Virol.* 65:2220-2224 (1991)). Examples of other packaging cell lines are described in Cone and Mulligan *Proceedings of the National Academy of Sciences, USA,* 81:6349-6353 (1984); Danos and Mulligan *Proceedings of the National Academy of Sciences, USA,* 85:6460-6464 (1988); Eglitis et al. (1988), supra; and Miller (1990), supra.

C. Pharmaceutical Formulations

When used for pharmaceutical purposes, the inhibitory nucleic acid is generally formulated in a suitable buffer, which can be any pharmaceutically acceptable buffer, such as phosphate buffered saline or sodium phosphate/sodium sulfate, Tris buffer, glycine buffer, sterile water, and other buffers known to the ordinarily skilled artisan such as those described by Good et al. *Biochemistry* 5:467 (1966).

The compositions can further include a stabilizer, an enhancer, and/or other pharmaceutically acceptable carriers or vehicles. A pharmaceutically acceptable carrier can contain a physiologically acceptable compound that acts, for example, to stabilize the inhibitory nucleic acids of the invention and any associated vector. A physiologically acceptable compound can include, for example, carbohydrates, such as glucose, sucrose or dextrans, antioxidants, such as ascorbic acid or glutathione, chelating agents, low molecular weight proteins or other stabilizers or excipients. Other physiologically acceptable compounds include wetting agents, emulsifying agents, dispersing agents or preservatives, which are particularly useful for preventing the growth or action of microorganisms. Various preservatives are well known and include, for example, phenol and ascorbic acid. Examples of carriers, stabilizers or adjuvants can be found in Remington's *Pharmaceutical Sciences,* Mack Publishing Company, Philadelphia, Pa., 17th ed. (1985).

D. Administration of Formulations

The formulations containing an inhibitory nucleic acid can be delivered to any tissue or organ using any delivery method known to the ordinarily skilled artisan. In some embodiments of the invention, the nucleic acid is formulated in mucosal, topical, and/or buccal formulations, particularly mucoadhesive gel and topical gel formulations. Exemplary permeation enhancing compositions, polymer matrices, and mucoadhesive gel preparations for transdermal delivery are disclosed in U.S. Pat. No. 5,346,701.

The formulations containing the inhibitory nucleic acid are typically administered to a cell. The cell can be provided as part of a tissue or as an isolated cell, such as in tissue culture. The cell can be provided in vivo, ex vivo, or in vitro.

The formulations can be introduced into the tissue of interest in vivo or ex vivo by a variety of methods. In some embodiments of the invention, the inhibitory nucleic acid is introduced into cells by such methods as microinjection, calcium phosphate precipitation, liposome fusion, ultrasound, electroporation, or biolistics. In further embodiments, the nucleic acid is taken up directly by the tissue of interest.

In some embodiments of the invention, the inhibitory nucleic acid is administered ex vivo to cells or tissues explanted from a patient, then returned to the patient. Examples of ex vivo administration of therapeutic gene constructs include Nolta et al., *Proc Natl. Acad. Sci. USA* 93(6):2414-9 (1996); Koc et al., *Seminars in Oncology* 23(1):46-65 (1996); Raper et al., *Annals of Surgery* 223(2): 116-26 (1996); Dalesandro et al., *J. Thorac. Cardi. Surg.,* 11(2):416-22 (1996); and Makarov et al., *Proc. Natl. Acad. Sci. USA* 93(1):402-6 (1996).

Effective dosage of the formulations will vary depending on many different factors, including means of administration, target site, physiological state of the patient, and other medicines administered. Thus, treatment dosages will need to be titrated to optimize safety and efficacy. In determining the effective amount of the vector to be administered, the physician should evaluate the particular nucleic acid used, the disease state being diagnosed; the age, weight, and overall condition of the patient, circulating plasma levels, vector toxicities, progression of the disease, and the production of anti-vector antibodies. The size of the dose also will be determined by the existence, nature, and extent of any adverse side-effects that accompany the administration of a particular vector. To practice the present invention, doses ranging from about 10 ng-1 g, 100 ng-100 mg, 1 μg-10 mg, or 30-300 μg inhibitory nucleic acid per patient are typical. Doses generally range between about 0.01 and about 50 mg per kilogram of body weight, preferably between about 0.1 and about 5 mg/kg of body weight or about $10^8$-$10^{10}$ or $10^{12}$ viral particles per injection. In general, the dose equivalent of a naked nucleic acid from a vector is from about 1 μg-100 μg for a typical 70 kg patient, and doses of vectors which include a retroviral particle are calculated to yield an equivalent amount of an inhibitory nucleic acid.

VIII. Kits

The invention also provides kits for treating or preventing an inflammatory condition or undesirable cell proliferation by inhibiting the specific binding between sPLA2-IIA and integrin according to the method of the present invention. The kits typically include a container that contains a pharmaceutical composition having an effective amount of an inhibitor for the specific binding between sPLA2-IIA and integrin, as well as informational material containing instructions on how to dispense the pharmaceutical composition, including description of the type of patients who may be treated (e.g., a person suffering from or at risk of developing a condition involving undesired inflammatory response or undesirable cell proliferation), the schedule (e.g., dose and frequency of administration) and route of administration, and the like.

EXAMPLES

The following examples are provided by way of illustration only and not by way of limitation. Those of skill in the art will readily recognize a variety of non-critical parameters that could be changed or modified to yield essentially the same or similar results.

Example 1

Experimental Procedures
  Materials—
  U937 monocytic cells and Chinese hamster ovary (CHO) cells were obtained from the American Type Culture Collection. K562 erythroleukemia cells that express human integrin αvβ3 (αvβ3-K562) (20) were provided by Eric Brown (University of California, San Francisco, Calif.). K562 cells that express human integrin α4 (α4-K562), CHO cells that express human integrin β3 (β3-CHO) or integrin α4 (α4-CHO) were described (14). Recombinant soluble αvβ3 was synthesized in CHO-K1 cells using the soluble αv and β3 expression constructs and purified by Ni-NTA affinity chromatography as described (21). Fibrinogen γ-chain C-terminal domain that lacks residues 400-411 (γC399tr) was synthesized as described (22). Fibronectin H120 fragment (FN-H120) (18), Fibronectin type III domains 8-11 (FN8-11) (19), and ADAM15 (23) were synthesized as GST fusion proteins as described in the cited references. Anti-human β3 mAb AV10 was provided by B. Felding-Habermann (The Scripps Research Institute, La Jolla, Calif.). HRP-conjugated anti-His tag antibody was purchased from Qiagen (Valencia, Calif.). Cmpd21 was synthesized as described (15).

Synthesis of sPLA2-IIA—

Recombinant sPLA2-IIA proteins (WT and mutants) were synthesized as described (14) using PET28a expression vector. The proteins were synthesized in *E. coli* BL21 and induced by isopropyl β-D-thiogalactoside as insoluble proteins. The proteins were solubilized in 8 M urea, purified by Ni-NTA affinity chromatography under denatured conditions, and refolded as previously described (14). The refolded proteins were >90% homogeneous upon SDS-PAGE.

Synthesis of Site 2 Peptides—

6His tag (SEQ ID NO: 12) was introduced to the BamHI site of pGEX-2T using 5'-GATCTCATCATCACCATCAC-CATG-3' (SEQ ID NO: 25) and 5'-GATCCATGGTGATG-GTGATGATGA-3' (SEQ ID NO: 26) (resulting vector is designated pGEX-2T6His). GST fusion protein of site 2 peptide (QPNDGQSHVGSDNHYSASTTM, residues 267-287 of β3, C273 is changed to S (SEQ ID NO: 27)) and a scrambled site 2 peptide (VHDSHYSGQGAMS-DNTNSPQT (SEQ ID NO: 28)) was synthesized by subcloning oligonucleotides that encodes these sequences into the BamHI/EcoRI site of pGEX-2T6His. The inventors synthesized the proteins in *E. coli* BL21 and purified using glutathione-Sepharose affinity chromatography (18). The corresponding β1, β2, and β4 peptides were generated as described (18).—please insert SEQ ID NOs in this paragraph Binding of Soluble αvβ3 to γC399tr—

ELISA-type binding assays were performed as described previously (18). Briefly, wells of 96-well Immulon 2 microtiter plates (Dynatech Laboratories, Chantilly, Va.) were coated with 100 μl 0.1 M NaHCO$_3$ containing γC399tr or ADAM15 for 2 h at 37° C. Remaining protein binding sites were blocked by incubating with PBS/0.1% BSA for 30 min at room temperature. After washing with PBS, soluble recombinant αvβ3 (5 μg/ml) in the presence or absence of sPLA2-IIA (WT or mutants) was added to the wells and incubated in HEPES-Tyrodes buffer (10 mM HEPES, 150 mM NaCl, 12 mM NaHCO$_3$, 0.4 mM NaH$_2$PO$_4$, 2.5 mM KCl, 0.1% glucose, 0.1% BSA) with 1 mM CaCl$_2$ for 2 h at room temperature. After unbound αvβ3 was removed by rinsing the wells with binding buffer, bound αvβ3 was measured using anti-integrin β3 mAb (AV-10) followed by HRP-conjugated goat anti-mouse IgG and peroxidase substrates.

Binding of Labeled Ligands to Integrins on the Cell Surface—

The cells were cultured to nearly confluent in RPMI 1640/10% FCS (K562 and U937) or DMEM/10% FCS (CHO cells). The cells were resuspended with RPMI 1640/0.02% BSA or DMEM/0.02% BSA and incubated for 30 min at room temperature to block remaining protein binding sites. The cells were then incubated with WT sPLA2-IIA or mutants for 5 min at room temperature and then incubated with FITC-labeled integrin ligands (γC399tr, FN-H120, FN8-11, and ADAM15) for 15 min at room temperature. For blocking experiments, sPLA-IIA was preincubated with S2-β1 peptide for 30 min at room temperature. The cells were washed with PBS/0.02% BSA and analyzed by FACSCalibur (Becton Dickinson, Mountain View, Calif.). For inhibition studies using Cmpd21, sPLA2-IIA was preincubated with Cmpd21 for 30 minutes at room temperature.

Binding of S2 Peptide to Proteins—

ELISA-type binding assays were performed as described previously (18). Briefly, wells of 96-well Immulon 2 microtiter plates (Dynatech Laboratories, Chantilly, Va.) were coated with 100 μl 0.1 M NaHCO$_3$ containing sPLA2-IIA, γC399tr, FN-H120 for 2 h at 37° C. Remaining protein binding sites were blocked by incubating with PBS/0.1% BSA for 30 min at room temperature. After washing with PBS, S2 peptides were added to the wells and incubated in PBS for 2 h at room temperature. After unbound S2 peptides were removed by rinsing the wells with PBS, bound S2 peptides (GST-tagged) were measured using HRP-conjugated anti-GST antibody and peroxidase substrates.

Adhesion Assays—

Adhesion assays were performed as described previously (18). Briefly, well of 96-well Immulon 2 microtiter plates were coated with 100 μl 0.1 M NaHCO$_3$ containing sPLA2-IIA (10 μg/ml) and were incubated for 2 h at 37° C. Remaining protein binding sites were blocked by incubating with PBS/0.1% BSA for 30 min at room temperature. After washing with PBS, α4-K562, or K562 cells in 100 μl RPMI 1640 were added to the wells and incubated at 37° C. for 1 hour in the presence of Cmpd21 (0-100 μM). After unbound cells were removed by rinsing the wells with RPMI 1640, bound cells were quantified by measuring endogenous phosphatase activity.

Chemotaxis—

Chemotaxis was measured in modified Boyden Chambers (Transwell). One μg/ml sPLA2-IIA and 20 μg/ml S2-β1 peptide or control peptides in 600 μl RPMI 1640 medium were placed in the lower chamber, and U937 cells (2×10$^5$ cells in 100 μl RPMI1640 medium) were placed in the upper chamber. After 5 h incubation at 37° C., cells in the lower chamber were counted.

Docking Simulation—

Docking simulation of interaction between sPLA2-IIA (1DCY.pdb) and integrin αvβ3 was performed using AutoDock3 as described (24). In the present study the inventors used the headpiece (residues 1-438 of αv and residues 55-432 of β3) of αvβ3 (closed-headpiece form, 1JV2.pdb). Cations were not present in αvβ3 during docking simulation, as in the previous studies using αvβ3 (open-headpiece form, 1L5G.pdb) (14, 24).

Other Methods—

Treatment differences were tested using ANOVA and a Tukey multiple comparison test to control the global type I error using Prism 5.0 (Graphpad Software). Surface plasmon resonance studies were performed as described (18).

Results sPLA2-IIA Activates Soluble Integrin αvβ3 in Cell-Free Conditions—

The inventors recently reported that FKN-CD can activate integrins in the absence of CX3CR1 through direct binding to site 2 of integrins (19). A peptide from site 2 of integrin β3 (S2-β3 peptide) directly binds to FKN-CD and suppresses FKN-CD-induced integrin activation (19). The newly identified site 2 is distinct from the classical RGD-binding site (site 1). The inventors propose that FKN-CD binding to site 2 induces activation of site 1 though conformational changes (in an allosteric mechanism). The site 2-mediated activation of integrins may not be limited to FKN-CD, and the inventors tested if other known integrin ligands activate αvβ3.

Figure 1:
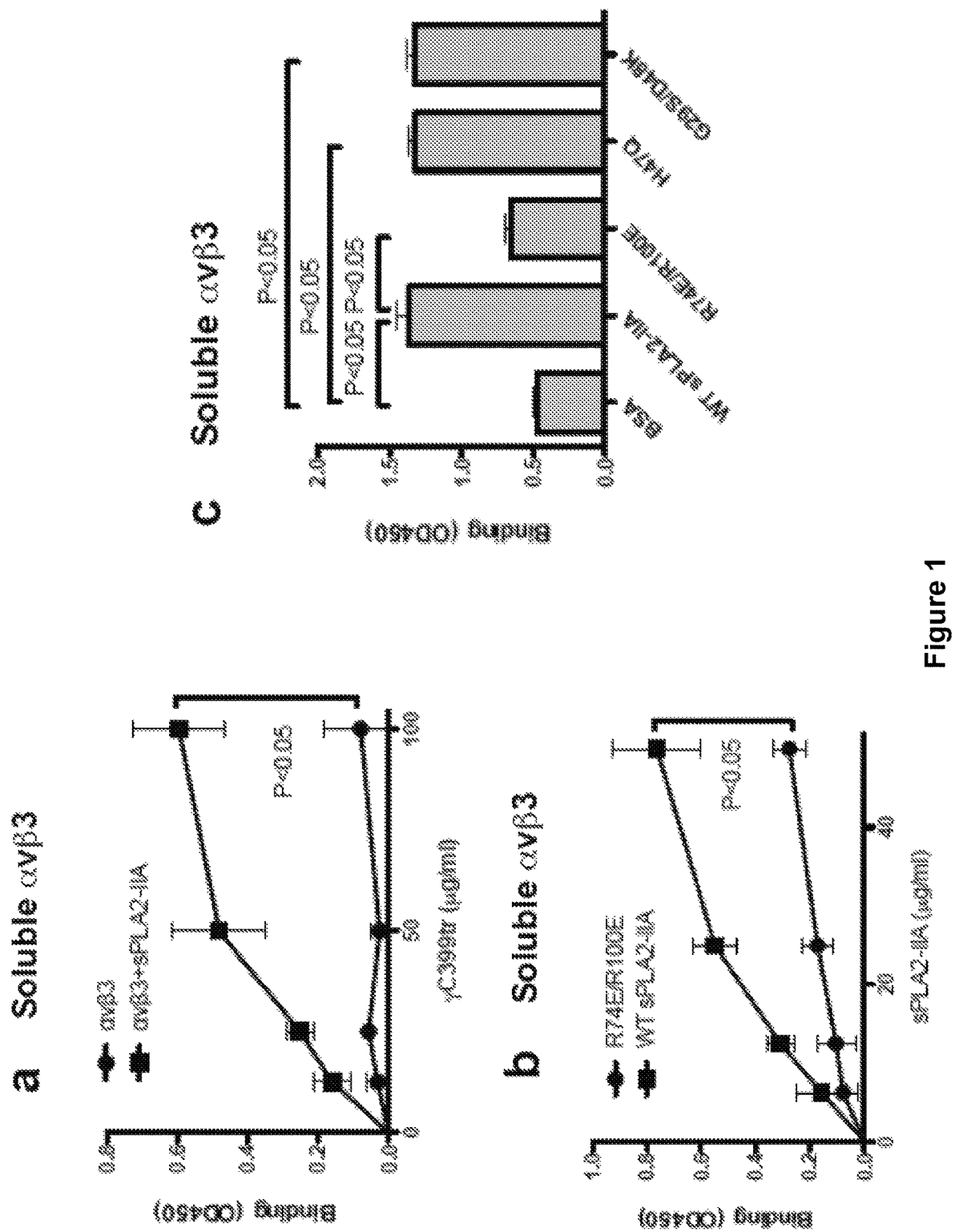
FIG. 1. sPLA2-IIA activates αvβ3 integrin in cell-free conditions (through direct integrin binding). a. Activation of soluble αvβ3 by sPLA2-IIA as a function of γC399tr concentration. Binding of soluble αvβ3 (5 μg/ml) to immobilized γC399tr in the presence or absence of WT sPLA2-IIA (50 μg/ml) was performed as described in the methods. Data are shown as means±SEM of three independent experiments. b. Activation of soluble αvβ3 by sPLA2-IIA as a function of sPLA2-IIA concentration. Wells of 96-well microtiter plates were coated with γC399tr (100 μg/ml) and incubated with soluble αvβ3 (5 μg/ml). Data are shown as means±SEM of three independent experiments. c. The effects of sPLA2-IIA mutations on integrin αvβ3 activation. Activation of soluble αvβ3 was measured as described above. SPLA2-IIA (50 μg/ml) and γC399tr (100 μg/ml for coating) were used. R74E/R100E, defective in integrin-binding; H74Q, catalytically inactive; G29S/D48K, defective in the binding to M-type receptor. d-f. The effects of sPLA2-IIA mutations on the binding of γC399tr to integrin αvβ3 on the cell surface. The binding of FITC-labeled γC399tr to the cells in the presence of sPLA2-IIA (up to 20 μg/ml in the case of U937 cells (d) and 20 μg/ml in αvβ3-K562 (e) and β3-CHO (f) cells) was measured using flow cytometry as described in the methods. Data are shown as means (median fluorescent intensity, MFI)±SEM of three independent experiments. g-i, The effects of sPLA2-IIA mutations on the binding of ADAM15 to integrin αvβ3. The binding of FITC-labeled ADAM15 to αvβ3 in the presence of sPLA2-IIA (20 μg/ml) in U937 (g), αvβ3-K562 (h) and β3-CHO (i) cells was measured using flow cytometry. Data are shown as means (MFI)±SEM of three independent experiments.
Figure 1:
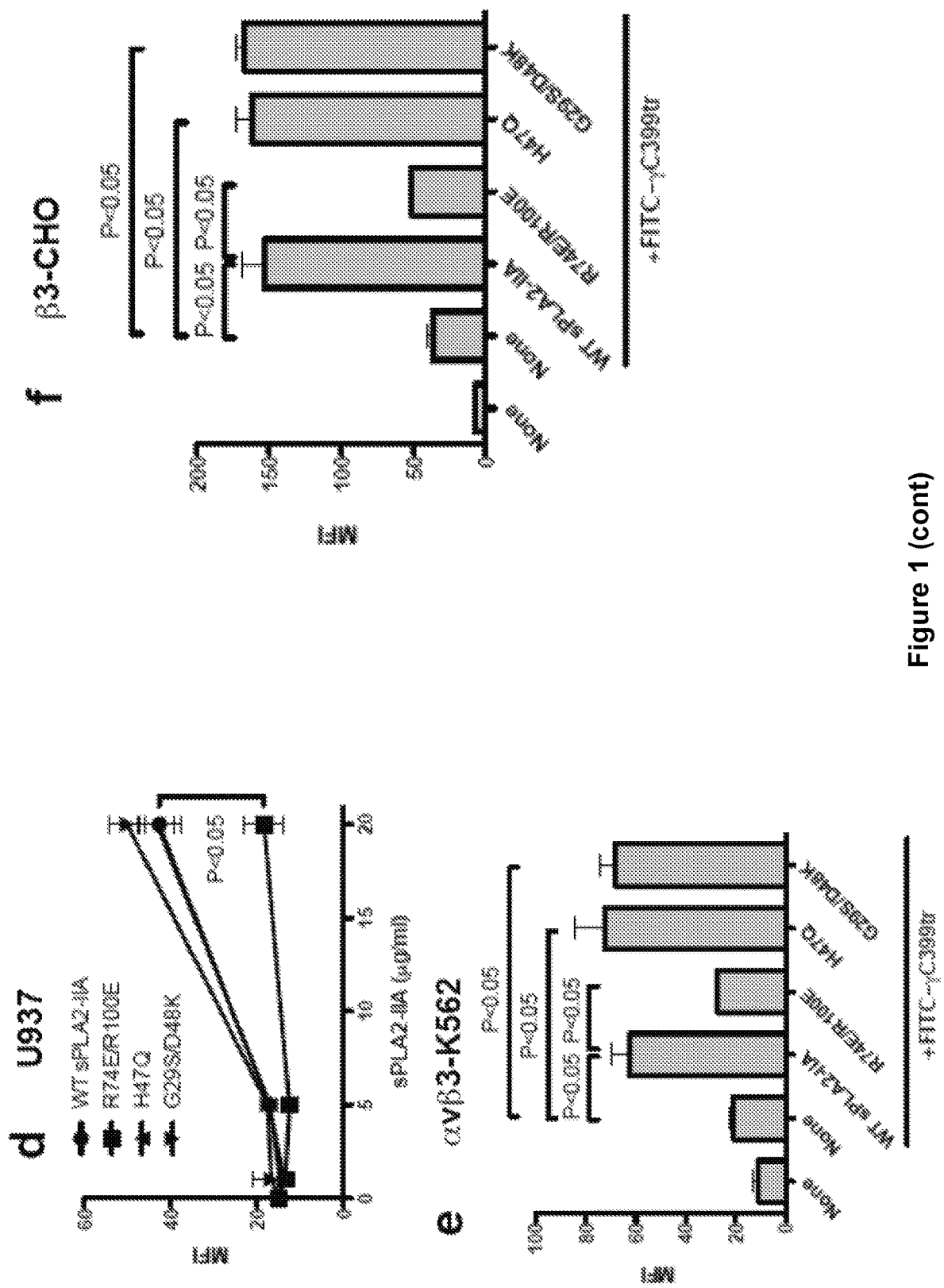
Figure 1:
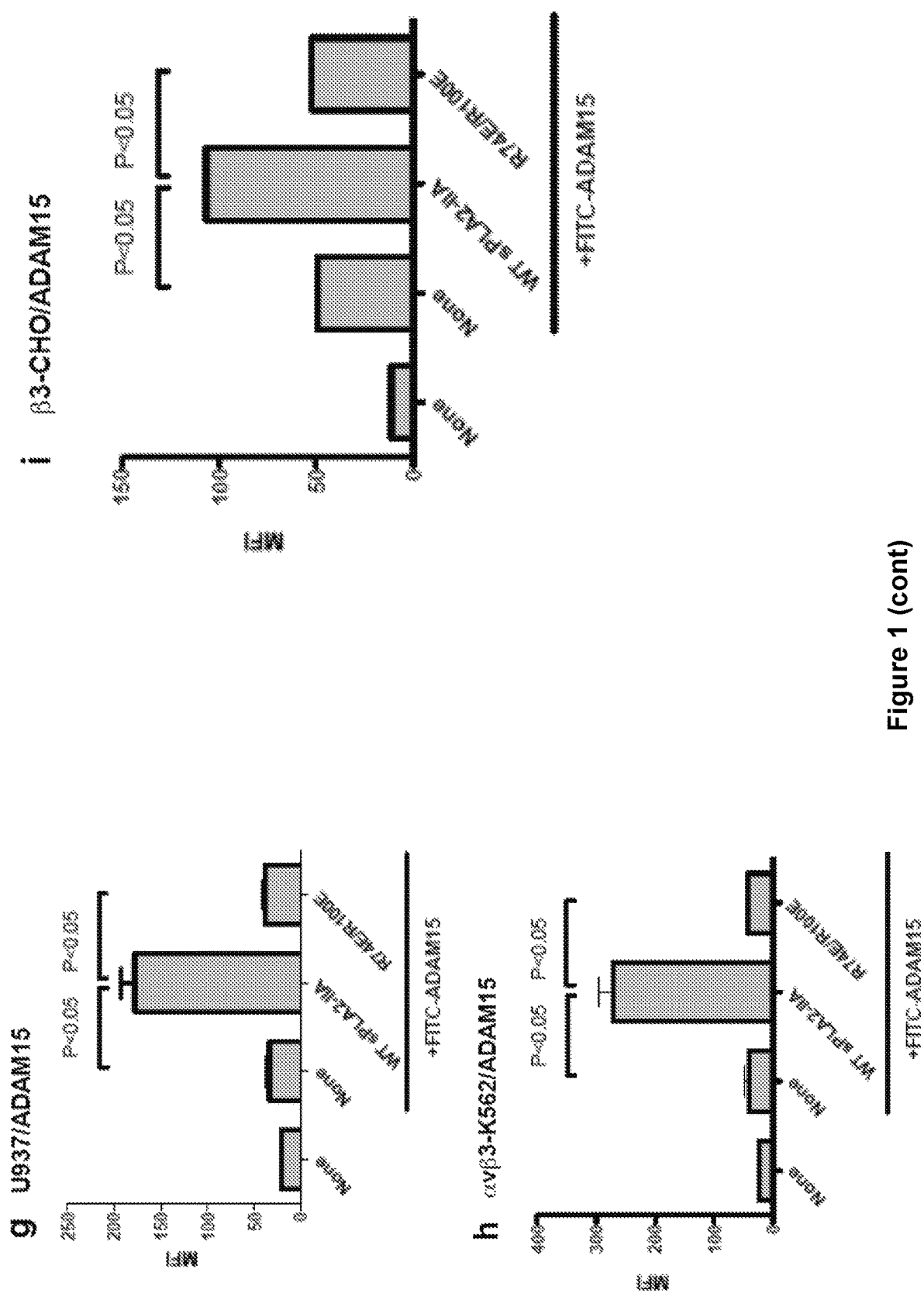

The inventors previously reported that sPLA2-IIA binds to integrins αvβ3 and α4β1 and induces signals through integrin pathways (14). The inventors studied if sPLA2-IIA enhances the binding of recombinant soluble αvβ3 to γC399tr, an αvβ3-specific ligand (22,25) in cell-free conditions. γC399tr was immobilized to wells of microtiter plates and measured the binding of soluble αvβ3 to γC399tr in the presence of sPLA2-IIA. To keep soluble integrin inactive 1 mM $Ca^{2+}$ was included in the assay. WT sPLA2-IIA enhanced the binding of γC399tr to αvβ3 in a concentration-dependent manner (FIGS. 1a and 1b). In contrast to WT sPLA2-IIA, the R74E/R100E mutant (integrin-binding defective) (14) was defective in this function (FIG. 1b). H47Q (catalytically inactive) and G29S/D48K (M-type receptor-binding defective) mutants behaved like WT sPLA2-IIA (FIG. 1c). These findings suggest that sPLA2-IIA activates αvβ3 in cell-free conditions and this activation requires the integrin-binding site of sPLA2-IIA but does not require catalytic activity or receptor binding.

The inventors studied if sPLA2-IIA activates integrins on the cell surface by measuring the binding of FITC-labeled γC399tr to cells using flow cytometry. WT sPLA2-IIA activated αvβ3 on U937 (αvβ3+)(FIG. 1d), K562 cells that express recombinant αvβ3 (αvβ3-K562 cells) (FIG. 1e), and CHO cells that express hamster αv/human β3 hybrid (β3-CHO cells) (FIG. 1f). The effects of sPLA2-IIA mutations on sPLA2-IIA-induced αvβ3 activation were similar to those in soluble αvβ3. These findings suggest that sPLA2-IIA activates αvβ3 on the cell surface in a manner similar to that of soluble αvβ3, and that the sPLA2-IIA-induced αvβ3 activation is not cell-type specific.

It is possible that the effect of sPLA2-IIA on αvβ3 may be specific to γC399tr. The inventors thus used the disintegrin domain of human ADAM15, which has an RGD motif and specifically binds to αvβ3 (23). The binding of FITC-labeled ADAM15 disintegrin domain was markedly enhanced by WT sPLA2-IIA, but not by R74E/R100E, in U937 (FIG. 1g), αvβ3-K562 (FIG. 1h) and β3-CHO cells (FIG. 1i), suggesting that the effect of sPLA2-IIA on the ligand binding to αvβ3 is not unique to γC399tr. It was confirmed that sPLA2-IIA does not directly interact with the integrin ligands used in this study (FIG. 10). sPLA2-IIA directly binds to integrins.

Docking simulation predicts that sPLA2-IIA binds to site 2 in an inactive form of αvβ3—

Figure 2:
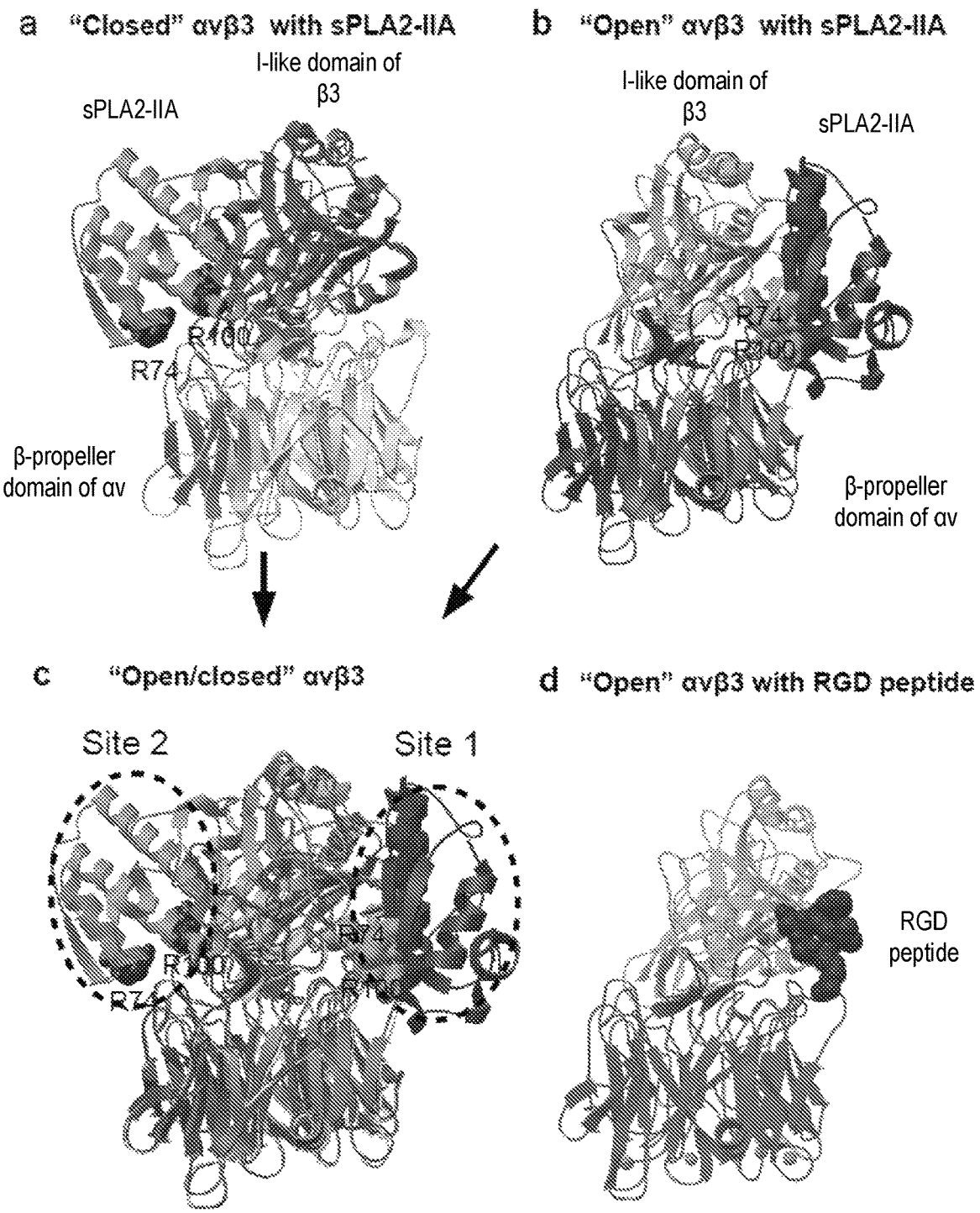
FIG. 2. Docking simulation predicts that sPLA2-IIA binds to a binding-site that is distinct from the classical RGD-binding site in closed-headpiece αvβ3. a. A docking model of sPLA2-IIA-integrin αvβ3 (inactive) interaction. The headpiece of an inactive form of integrin αvβ3 (PDB code 1JV2) was used as a target. b. A docking model of sPLA2-IIA-integrin αvβ3 (active) interaction (14). The headpiece of ligand-bound form of integrin αvβ3 (PDB code 1L5G) was used as a target. The model predicts that sPLA2-IIA (PDB code 1DCY) binds to the classical RGD-binding site of the integrin αvβ3 headpiece (site 1). The model predicts the position of the second sPLA2-IIA-binding site (site 2). c. Superposition of two models shows that the positions of two predicted sPLA2-IIA binding sites are distinct. d. open-headpiece αvβ3 structure (1L5G) with an RGD-containing peptide (site 1).

The inventors studied if sPLA2-IIA-induced activation of αvβ3 involves the binding of sPLA2-IIA to site 2 of αvβ3. Docking simulation of the interaction between sPLA2-IIA and the closed-headpiece form of αvβ3 (PDB code 1JV2) predicts that sPLA2-IIA binds to site 2 with high affinity (docking energy −22.1 kcal/mol) (FIG. 2a), as in the case of FKN-CD (19). Site 2 is located at the opposite side of site 1 (FIGS. 2b and 2c). The RGD peptide binds binds to site 1 in the open-headpiece αvβ3 (FIG. 2d). Amino acid residues in sPLA2-IIA and integrin αvβ3 that are involved in sPLA2-IIA-αvβ3 integrin are listed in Table 1. The docking model predicts that Arg74 and Arg100 are within the sPLA2-IIA/αvβ3 interface at site 2 (FIG. 1a), suggesting that the integrin binding interface in sPLA2-IIA at site 2 overlaps with that of site 1. This predicts that sPLA2-IIA may activate integrins through direct binding to site 2, and that the R74E/R100E mutant may be defective in this function.

sPLA2-IIA Directly Binds to a Peptide Derived from Site 2 of Integrin β1—

Figure 3:
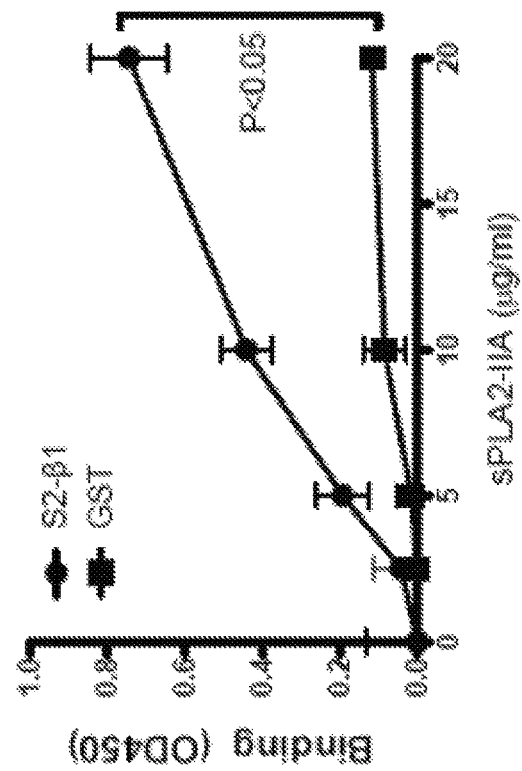
FIG. 3. Site 2 peptide from β1 binds to sPLA2-IIA. a. Alignment of peptides from site 2 from different integrin β subunits (β1 275-294=SEQ ID NO:1; β2 258-277=SEQ ID NO:2; β3 267-287=SEQ ID NO:3; β4 255-275=SEQ ID NO:4). b. Binding of site 2 peptides from different integrin β subunits (S2-β1, β2, β3, and (34) to immobilized sPLA2-IIA (20 μg/ml). The binding of peptides to immobilized sPLA2-IIA was measured as described in the methods. Data are shown as means±SEM of three independent experiments. c. Binding of S2-11 peptide to sPLA2-IIA as a function of sPLA2-II concentrations. The binding of the peptide to immobilized sPLA2-IIA was measured as described in (b). Data are shown as means±SEM of three independent experiments. d. Suppression of γC399tr to U937 cells by site 2 peptide. The binding of FITC-labeled γC399tr to αvβ3 on U937 was measured in flow cytometry as described in the Methods section. Data are shown as means±SEM of MFI of three independent experiments. e. Suppression of γC399tr to αvβ3-K562 cells by site 2 peptide. The binding of FITC-labeled γC399tr to αvβ3 on αvβ3-K562 was measured in flow cytometry as described in the Methods section. Data are shown as means±SEM of MFI of three independent experiments. sPLA2-IIA (20 μg/ml)
Figure 3:
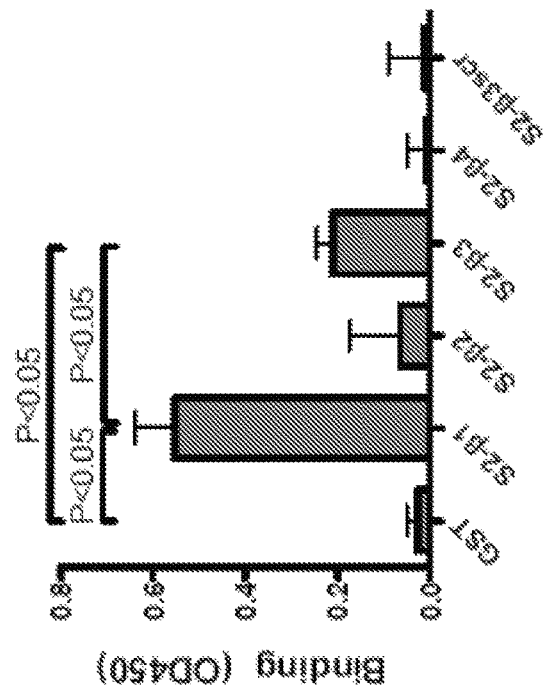
Figure 3:
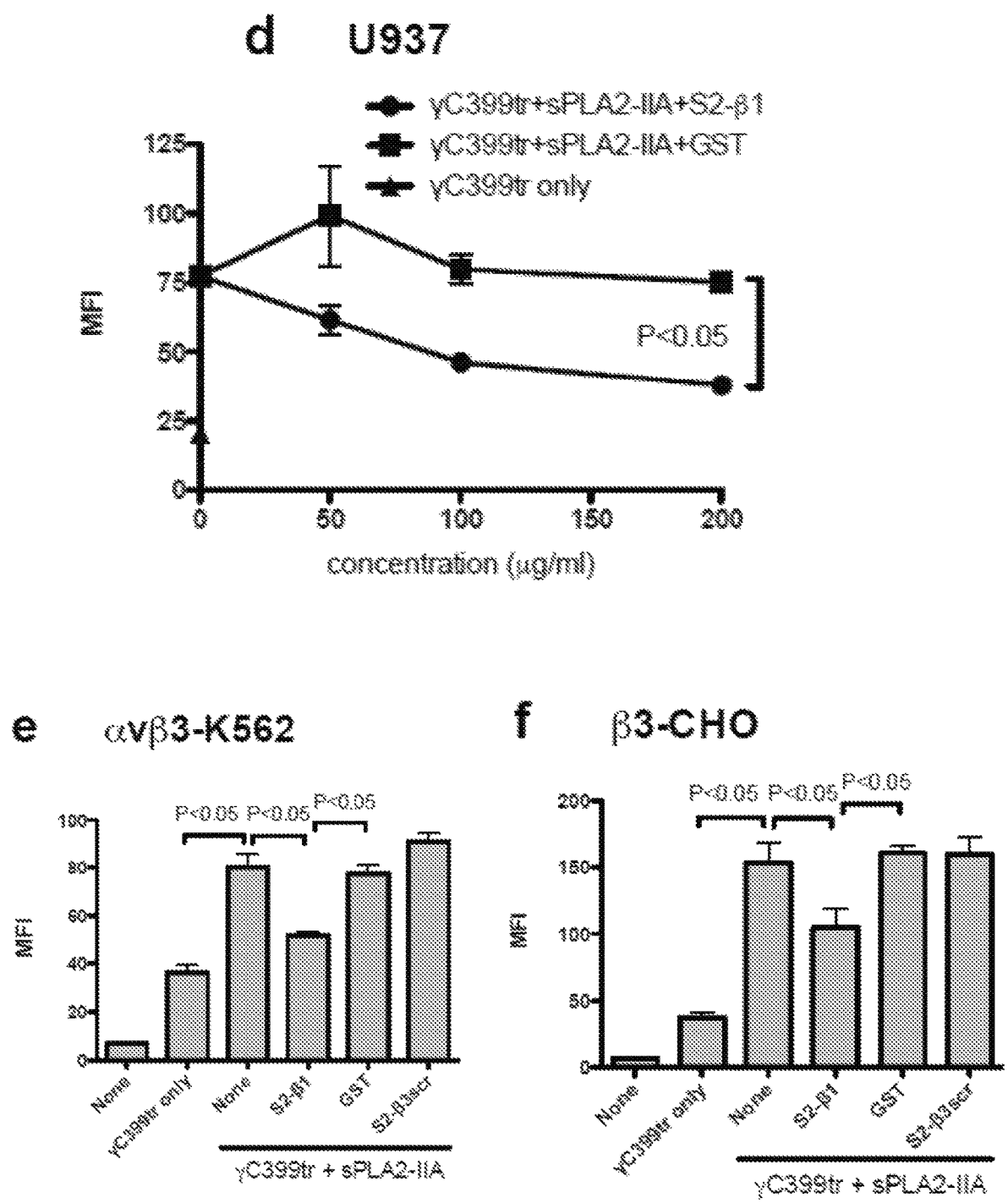

The inventors previously identified a peptide sequence (e.g., residues 256-288 of β3, S2-β3 peptide) from site 2 of αvβ3 that directly interacts with FKN-CD (FIG. 3a). The peptide suppresses FKN-CD-mediated integrin activation, but control scrambled peptide does not (19). The inventors studied if site 2-derived peptides bind to sPLA2-IIA. It was expected that S2-β3 peptide binds to sPLA2-IIA, because the amino acid residues in S2-β3 peptide are located within the integrin-binding interface of sPLA2-IIA in the docking model (Table 1). Interestingly, site 2 peptides from β1 (S2-β1 peptide) bound better to sPLA2-IIA in a concentration-dependent manner than S2-β3 peptide (FIGS. 3b and 3c). Control GST or scrambled S2-β3 peptide (S2-β3scr) did not bind to sPLA2-IIA. This suggests that site 2 has different binding specificity to FKN-CD and sPLA2-IIA. S2-β1 peptide suppressed sPLA2-IIA-mediated αvβ3 activation in U937 (FIG. 3d), αvβ3-K562 (FIG. 3e), and β3-CHO (FIG. 3f) cells, while control GST or S2-β3scr peptide did not. These findings suggest that sPLA2-IIA binds specifically to site 2 and that the binding of sPLA2-IIA to site 2 is critical for sPLA2-IIA-mediated αvβ3 activation.

sPLA2-IIA Activates α4β1 in a Site 2-Dependent Manner.—

The inventors have reported that sPLA2-IIA directly binds to another integrin, α4β1, and induces signals in an α4β1-dependent manner (14). The inventors found that sPLA2-IIA enhanced the binding of FITC-labeled fibronectin fragment specific to α4β1 (H120) to U937 cells (α4+) (FIG. 4a), K562 cells that express recombinant α4 (α4-K562) (FIG. 4c), and CHO cells that express recombinant α4 (α4-CHO) (FIG. 4e). This suggests that sPLA2-IIA activates α4β1. WT sPLA2-IIA markedly increased the binding of H120 to α4β1, while R74E/R100E did not (FIGS. 4a, 4c, and 4e). The H47Q or G29S/D48K mutants induced α4β1 activation, like WT sPLA2-IIA, suggesting that catalytic activity or receptor binding of sPLA2-IIA is not important. S2-β1 peptide suppressed the binding of H120 to α4β1 increased by sPLA2-IIA, while control GST or S2-β3scr peptide did not (FIGS. 4b, 4d and 4e). These results suggest that sPLA2-IIA activates integrin α4β1 through direct binding to site 2 in a manner similar to that of αvβ3.

Cmpd21 that Binds to sPLA2-IIA Inhibits sPLA2 IIA-Mediated αvβ3 and α4β1 Activation—

The inventors recently identified small compounds that bind to sPLA2-IIA and suppress sPLA2-IIA binding to αvβ3 (15), including compound 21 (Cmpd21) (FIG. 5a). Cmpd21 was selected because of its ability to bind to WT sPLA2-IIA, but not to R74E/R100E (15). Cmpd21 binds to the integrin-binding site of sPLA2-IIA and suppresses adhesion of αvβ3-K562 cells to γC399tr (15). Consistently, Cmpd21 suppressed the binding of sPLA2-IIA to αvβ3 in a concentration-dependent manner in surface plasmon resonance studies (FIG. 5b). The inventors found that Cmpd21 suppressed the γC399tr binding to αvβ3-K562, U937, and β3-CHO cells in a concentration-dependent manner in three different cell types (FIGS. 5c, 5d and 5e). Cmpd21 also suppressed the adhesion of α4-K562 cells to sPLA2-IIA in a concentration-dependent manner (FIG. 6a), suggesting that the effect of Cmpd21 is not limited to sPLA2-IIA-αvβ3 interaction. Cmpd21 suppressed sPLA2-IIA-induced binding of H120 to α4β1 in three different cell types (FIG. 6b-d). These findings suggest that Cmpd21 suppresses sPLA2-IIA-mediated αvβ3 and α4β1 activation through site 2 by binding to the integrin-binding site of sPLA2-IIA.

sPLA2-IIA Enhances the Binding of the Fibronectin Fragment that Contains the RGD Motif to α5β1.—

The interaction between the RGD-containing cell-binding fibronectin type III fragment and integrins has been extensively studied as a prototype cell-extracellular matrix interaction. The inventors decided to study if sPLA2-IIA enhances the binding of this fragment to integrin α5β1 using rat fibronectin domains 8-11 (FN8-11). The inventors thus studied FN8-11 binding to α5β1 and found that sPLA2-IIA bound to integrin α5β1 in K562 cells, in which α5β1 is the only β1 integrin, and that mAb KH72 specific to α5 suppressed the binding, suggesting that sPLA2-IIA is a ligand of β5β1 (FIG. 7a). The binding of sPLA2-IIA to U937 cells was suppressed by KH73 (anti-α5), 7E3 (anti-αvβ3), and SG73 (anti-α4), suggesting αvβ3, and α4β1, in addition to α5β1, are involved in sPLA2-IIA binding to U937 cells (FIG. 7b). Cmpd21 effectively suppressed the adhesion of K562 cells to sPLA2-IIA (FIG. 7c). These findings suggest that sPLA2-IIA interacts with α5β1. The inventors discovered that sPLA2-IIA markedly increased the binding of FITC-labeled FN8-11 to β5β1 on U937, K562, and CHO cells, while R74E/R100E did not (FIGS. 7d-f). The H47Q or G29S/D48K mutants induced α5β1 activation, like WT sPLA2-IIA. These findings suggest that sPLA2-IIA activates integrin α5β1, and that catalytic activity or receptor binding of sPLA2-IIA is not required for this process, as in the case of αvβ3 and α4β1. S2-β1 peptide suppressed the binding of FN8-11 to α5β1 increased by sPLA2-IIA, while control GST or scrambled β3 peptide did not (FIG. 7g-i). Cmpd21 suppressed sPLA2-IIA-induced binding of FN8-11 to α5β1 in three different cell types (FIG. 7j-1), suggesting Cmpd21 suppresses sPLA2-IIA-induced α5β1 activation through site 2 as well. Taken together, these results suggest that sPLA2-IIA enhances FN8-11 to integrin α5β1 through direct binding of sPLA2-IIA to site 2, as in the case of αvβ3 and α4β1.

sPLA2-IIA Suppresses H120 Binding to α4β1 at High Concentrations.—

If sPLA2-IIA binds to site 1 (14) and site 2 (the present study), it is predicted that sPLA2-IIA competes with ligands for binding to site 1. To address this question, the inventors determined the effect of sPLA2-IIA as a function of sPLA2-IIA concentrations up to 500 μg/ml. The binding of H120 to α4-CHO cells was maximum at 20 μg/ml sPLA2-IIA and then reduced as sPLA2-IIA concentration increases (FIG. 8). This suggests that 1) sPLA2-IIA at low concentrations binds to site 2 of closed α4β1 (site 1 closed, site 2 open) and activates α4β1 (site 1 open). 2) when site 2 is saturated with sPLA2-IIA, sPLA2-IIA competes with H120 for binding to site 1 (open) and reduce the binding of H120.

Discussion

The present study establishes that sPLA2-IIA activates integrins αvβ3, α4β1, and α5β1 through direct binding to site 2. sPLA2-IIA activated recombinant soluble αvβ3 in cell-free conditions, suggesting that inside-out signals or other molecules are not involved. This process does not include catalytic activity or receptor binding of sPLA2-IIA since mutating the catalytic center or receptor-binding site of sPLA2-IIA did not affect sPLA2-IIA-mediated integrin activation. sPLA2-IIA induced integrin activation through binding to site 2 is a novel mechanism of integrin activation and pro-inflammatory action by sPLA2-IIA. sPLA2-IIA may activate other integrins through direct binding.

sPLA2-IIA-mediated integrin activation happens in biological fluids (at least in tears). In the present study, >5 μg/ml sPLA2-IIA was required to detect sPLA2-IIA-induced integrin activation. Notably, the concentration of sPLA2-IIA is exceptionally high in human tears (26-28). In normal subjects, the concentration of sPLA2-IIA in tears is 54.5+/−33.9 μg/ml, one of the highest levels of sPLA2-IIA reported in any normal human secretions (29). Therefore integrin activation by sPLA2-IIA happens at least in tears. sPLA2-IIA appears to be secreted by both the lacrimal glands and the goblet cells of conjunctival epithelia (26,30). Since sPLA2-IIA is bacteriocidal and kills Listera at much lower concentrations (<0.1 nM), it is possible that the primary functions of sPLA2-IIA at such high concentrations in tears might be integrin activation. It is likely that sPLA2-IIA in tears may play a role in enhancing immune response to bacterial pathogens through local integrin activation in tears or perhaps in other tissues. Serum levels of sPLA2-IIA are increased only up to 1 μg/ml during systemic inflammation (2, 3). sPLA2-IIA may not effectively activate integrins at these concentrations. It is, however, possible that sPLA2-IIA may be highly concentrated in diseased tissues in chronic inflammation or on the cell surface through binding to proteoglycans.

The sPLA2-IIA-induced integrin activation is expected to enhance interaction between cells and extracellular matrix (e.g., fibrinogen and fibronectin) and thereby induce massive proliferative signals. Since integrins are involved in growth factor signaling through crosstalk with growth factor receptors, sPLA2-IIA-induced integrin activation is also expected to enhance cellular responsiveness to growth factors. The inventors have reported that integrins crosstalk with several growth factor receptors through direct binding to growth factors (e.g., fibroblast growth factor-1 (24, 31-33), insulin-like growth factor-1 (34-37), neuregulin-1 (38), and fractalkine (18)). The inventors propose that sPLA2-IIA-induced integrin activation indirectly affects intracellular signaling by these growth factors through enhancing integrin binding to growth factors.

The inventors establish that site 2 is involved in integrin activation by sPLA2-IIA (the current study) and FKN-CD (19) (FIG. 9). This is a new mechanism of integrin activation. It has previously been reported that the binding of a RGD-mimetic peptide induces changes in the tertiary structure of αvβ3 (39) and αIIbβ3 (40) in the β3 I-like domain. RGD or ligand-mimetic peptides activate purified, non-activated αIIbβ3 (41) and αvβ3 (42). This process does not require inside-out signal transduction and it appears that RGD or ligand-mimetic peptide triggers conformational changes that lead to full activation of integrins. These findings suggest that these peptides enhance integrin affinity by conformational changes in the headpiece possibly through additional ligand-binding sites in the integrin (41). A previous study suggests that there are two RGD-binding sites in integrin αIIbβ3, and that one binding site acts as an allosteric site based on binding kinetic studies (43). Also, another study suggests that two distinct cyclic RGD-mimetic peptides can simultaneously bind to distinct sites in αIIbβ3, and the estimated distance between two ligand-binding site is about 6.1+/−0.5 nm (44). The possible allosteric ligand-binding site has not been pursued probably because the αvβ3 structure (ligand occupied, open-headpiece) contains only one RGD-binding site (39). In our docking model the distance between site 1 and site 2 is about 6 nm. Thus, the position of site 2 is consistent with the previous report. Based on previous studies it is likely that the newly identified site 2 has ligand specificity that overlaps with that of site 1, interacts with integrin ligands other than FKN-CD (e.g., RGD), and is potentially involved in integrin regulation in an allosteric mechanism. It is reasonable to assume that FKN-CD or sPLA2-IIA binding to site 2 induces conformational changes in integrins. It was suspected that other proteins also bind to site 2 and affect integrin functions. Also it is likely that integrins other than αvβ3, α4β1, and α5β1 are activated by site 2-mediated mechanism. It would be interesting to address this question in future studies.

It is unclear whether sPLA2-IIA-induced integrin activation requires global conformational changes in integrins. In current models of integrin activation, activation of β1 integrins induces a swing-out movement of the hybrid domain and exposes epitopes recognized by activation-dependent antibodies (anti-human β1 HUTS4 and HUTS21)(45). The HUTS4 and HUTS21 epitopes are located in the hybrid domain of 31 (46,47). In our preliminary experiments, sPLA-IIA did not change reactivity of β1 integrins to HUTS4 and HUTS21 in U937, K562, and α4-K562 cells in RPMI1640 medium under the conditions in which sPLA2-IIA enhanced the binding of β1 integrins to ligands. It is possible that the binding of sPLA2-IIA to site 2 induces only local conformational changes within the headpiece of integrins. Interestingly, the open-headpiece (PDB code 1L5G) and closed-headpiece (PDB code 1JV2) conformations of αvβ3 are very similar (39,48). Surprisingly, the docking simulation distinguished the two conformations and predicted the position of site 2 in the closed-headpiece form. It was shown that sPLA2-IIA (the current study) FKN-CD (19) actually bind to site 2 and the binding of sPLA2-IIA and FKN to site 2 is required for integrin activation using the peptides from site 2. It is likely that integrins that are activated by sPLA2-IIA and FKN-CD through site 2 have conformations similar to the open-headpiece αvβ3 that has no global conformational changes compared to the closed-headpiece form. The open- and closed-headpiece conformations of αvβ3 may really reflect the fact that integrins can be activated without global conformational changes through allosteric mechanism.

The site 2-derived integrin peptides were used for establishing that sPLA2-IIA really binds to site 2, and the interaction is involved in integrin activation. It was studied if S2-β1 peptide acts as an antagonist for sPLA2-IIA-mediated pro-inflammatory signals (FIG. 11). S2-β1 peptide suppressed chemotaxis induced by sPLA2-IIA. Although it is unclear if S2-β1 peptide suppressed the binding of sPLA2-IIA to site 1 or site 2 at this point, the results suggest that S2-β1 peptide has potential as a therapeutic.

Specific inhibitors of sPLA2-IIA catalytic activity S-5920/LY315920Na and S-3013/LY333013 failed to demonstrate a significant therapeutic effect in rheumatoid arthritis (49) and asthma (50). Our previous study suggests that sPLA2-IIA-integrin interaction may be a potential target for chronic inflammatory diseases (14). Cmpd21 was screened for its ability to bind to the integrin-binding site of sPLA2-IIA (15). Indeed Cmpd21 suppressed the binding of sPLA2-IIA to integrins, and, in the present study, the inventors demonstrated that Cmpd21 suppressed the sPLA2-IIA-induced integrin activation via site 2 as well. It would be interesting to study if Cmpd21 or its variants suppress inflammation in vivo in future studies.

Example 2

ELISA binding assays were performed to test and compare the binding ability of peptides comprising the amino acid sequences of SEQ ID NO:1 and SEQ ID NO:3. either as linear peptides (linear b1 and linear b3 in FIG. 12) or cyclic peptides (cyclic b1 and cyclic b3 in FIG. 12). to sPLA2-IIA and fractalkine (FKN). Wells of 96-well microtiter plates were coated with sPLA2-IIA or FKN at 10 ug-ml coating concentrations, while remaining protein binding sites were blocked with BSA. Wells were incubated with site 2 peptides (GST fusion) in PBS for 1 hour and bound GST was determined using anti-GST antibodies (HRP-conjugated) and peroxidase substrate.

Data are shown in FIG. 12 comparing cyclic site 2 peptides (β1 and β3) binding to sPLA2-IIA or FKN. Cyclic β1 peptide showed binding ability very similar to linear β1 peptide in its binding to sPLA2-IIA or FKN, but cyclic β3 peptide showed a stronger binding ability to sPLA2-IIA and FKN than linear β3 peptide. In additional testing, linear β1 and β3 peptides did not bind to other ligands (e.g., SDF-1, IGF-1), whereas both cyclic β1 and β3 peptides bound to the ligands.

All patents, patent applications, and other publications cited in this application, including published amino acid or polynucleotide sequences, are incorporated by reference in the entirety for all purposes.

TABLE 1

Amino acid residues involved in the interaction between sPLA2-IIA and integrin αvβ3.
Amino acid residues within 6 angstrom between sPLA2-IIA and αvβ3 were selected using
pdb viewer (version 4.1). Amino acid residues in β3 site 2 peptide (S2-β3) are shown in bold.

| αv | β3 | sPLA2-IIA |
|---|---|---|
| Glu15, Lys42, Asn44, Gly49, Ile50, Val51, Glu52, Asn77, Ser90, His91, Trp93, Arg122, Ala397, Arg398, Ser399 | Pro160, Val161, Ser162, Met165, Ser168, Pro169, Pro170, Glu171, Ala172, Leu173, Glu174, Asn175, Leu185, Pro186, Met187, Phe188, His192, Val193, Leu194, Glu206, Ala263, Gly264, Gln267, Gly276, Ser277, Asp278, Asn279, His280, Ser282, Ala283, Thr285, Thr286 | Lue11, Thr13, Gly14, Lys15, Ser35, Pro36, Lys37, Asp38, Ala39, Arg42, Val45, Thr46, His47, Cy49, Cy50, Arg53, Ser71, Gly72, Ser73, Arg74, Cys97, Arg100, Asn101, Lys102, Thr103, Thr104, Tyr105, Asn106, Lys107, Lys108, Tyr109, Tyr112, Arg118, Ser120, Pro122, Arg123, Cys124 |

REFERENCES

1. Vadas, P., Stefanski, E., and Pruzanski, W. (1985) Characterization of extracellular phospholipase A2 in rheumatoid synovial fluid. *Life Sci* 36, 579-587
2. Jaross, W., Eckey, R., and Menschikowski, M. (2002) Biological effects of secretory phospholipase A(2) group IIA on lipoproteins and in atherogenesis. *Eur J Clin Invest* 32, 383-393
3. Niessen, H. W., Krijnen, P. A., Visser, C. A., Meijer, C. J., and Erik Hack, C. (2003) Type II secretory phospholipase A2 in cardiovascular disease: a mediator in atherosclerosis and ischemic damage to cardiomyocytes? *Cardiovasc Res* 60, 68-77

4. Jiang, J., Neubauer, B. L., Graff, J. R., Chedid, M., Thomas, J. E., Roehm, N. W., Zhang, S., Eckert, G J., Koch, M. O., Eble, J. N., and Cheng, L. (2002) Expression of group IIA secretory phospholipase A2 is elevated in prostatic intraepithelial neoplasia and adenocarcinoma. *The American journal of pathology* 160, 667-671
5. Dong, Q., Patel, M., Scott, K. F., Graham, G G, Russell, P. J., and Sved, P. (2006) Oncogenic action of phospholipase A2 in prostate cancer. *Cancer letters* 240, 9-16
6. Sved, P., Scott, K. F., McLeod, D., King, N. J., Singh, J., Tsatralis, T., Nikolov, B., Boulas, J., Nallan, L., Gelb, M. H., Sajinovic, M., Graham, G G, Russell, P. J., and Dong, Q. (2004) Oncogenic action of secreted phospholipase A2 in prostate cancer. *Cancer research* 64, 6934-6940
7. Tada, K., Murakami, M., Kambe, T., and Kudo, I. (1998) Induction of cyclooxygenase-2 by secretory phospholipases A2 in nerve growth factor-stimulated rat serosal mast cells is facilitated by interaction with fibroblasts and mediated by a mechanism independent of their enzymatic functions. *J Immunol* 161, 5008-5015
8. Triggiani, M., Granata, F., Balestrieri, B., Petraroli, A., Scalia, G, Del Vecchio, L., and Marone, G (2003) Secretory phospholipases A2 activate selective functions in human eosinophils. *J Immunol* 170, 3279-3288
9. Lambeau, G, Ancian, P., Barhanin, J., and Lazdunski, M. (1994) Cloning and expression of a membrane receptor for secretory phospholipases A2. *The Journal of biological chemistry* 269, 1575-1578
10. Nicolas, J. P., Lambeau, G, and Lazdunski, M. (1995) Identification of the binding domain for secretory phospholipases A2 on their M-type 180-kDa membrane receptor. *The Journal of biological chemistry* 270, 28869-28873
11. Cupillard, L., Mulherkar, R., Gomez, N., Kadam, S., Valentin, E., Lazdunski, M., and Lambeau, G (1999) Both group IB and group IIA secreted phospholipases A2 are natural ligands of the mouse 180-kDa M-type receptor. *The Journal of biological chemistry* 274, 7043-7051
12. Hynes, R. O. (2002) Integrins: bidirectional, allosteric signaling machines. *Cell* 110, 673-687
13. Takada, Y, Ye, X., and Simon, S. (2007) The integrins. *Genome Biol* 8, 215
14. Saegusa, J., Akakura, N., Wu, C. Y, Hoogland, C., Ma, Z., Lam, K. S., Liu, F. T., Takada, Y K., and Takada, Y (2008) Pro-inflammatory secretory phospholipase A2 type IIA binds to integrins alphavbeta3 and alpha4beta1 and induces proliferation of monocytic cells in an integrin-dependent manner. *The Journal of biological chemistry* 283, 26107-26115
15. Ye, L., Dickerson, T., Kaur, H., Takada, Y K., Fujita, M., Liu, R., Knapp, J. M., Lam, K. S., Schore, N. E., Kurth, M. J., and Takada, Y (2013) Identification of inhibitors against interaction between pro-inflammatory sPLA2-IIA protein and integrin alphavbeta3. *Bioorg Med Chem Lett* 23, 340-345
16. Zhu, J., Zhu, J., and Springer, T. A. (2013) Complete integrin headpiece opening in eight steps. *J Cell Biol* 201, 1053-1068
17. Xiong, J. P., Mahalingham, B., Alonso, J. L., Borrelli, L. A., Rui, X., Anand, S., Hyman, B. T., Rysiok, T., Muller-Pompalla, D., Goodman, S. L., and Arnaout, M. A. (2009) Crystal structure of the complete integrin alphaVbeta3 ectodomain plus an alpha/beta transmembrane fragment. *J Cell Biol* 186, 589-600
18. Fujita, M., Takada, Y. K., and Takada, Y. (2012) Integrins alphavbeta3 and alpha4beta1 Act as Coreceptors for Fractalkine, and the Integrin-Binding Defective Mutant of Fractalkine Is an Antagonist of CX3CR1. *J Immunol* 189, 5809-5819
19. Fujita, M., Takada, Y K., and Takada, Y (2014) The Chemokine Fractalkine Can Activate Integrins without CX3CR1 through Direct Binding to a Ligand-Binding Site Distinct from the Classical RGD-Binding Site. *PLoS One* 9, e96372
20. Blystone, S. D., Graham, I. L., Lindberg, F. P., and Brown, E. J. (1994) Integrin alpha v beta 3 differentially regulates adhesive and phagocytic functions of the fibronectin receptor alpha 5 beta 1. *J Cell Biol* 127, 1129-1137
21. Takagi, J., Erickson, H. P., and Springer, T. A. (2001) C-terminal opening mimics 'inside-out' activation of integrin alpha5beta1. *Nat Struct Biol* 8, 412-416
22. Yokoyama, K., Zhang, X. P., Medved, L., and Takada, Y. (1999) Specific binding of integrin alpha v beta 3 to the fibrinogen gamma and alpha E chain C-terminal domains. *Biochemistry* 38, 5872-5877
23. Zhang, X. P., Kamata, T., Yokoyama, K., Puzon-McLaughlin, W., and Takada, Y (1998) Specific interaction of the recombinant disintegrin-like domain of MDC-15 (metargidin, ADAM-15) with integrin alphavbeta3. *The Journal of biological chemistry* 273, 7345-7350
24. Mori, S., Wu, C. Y, Yamaji, S., Saegusa, J., Shi, B., Ma, Z., Kuwabara, Y, Lam, K. S., Isseroff, R. R., Takada, Y K., and Takada, Y (2008) Direct Binding of Integrin {alpha}v{beta}3 to FGF1 Plays a Role in FGF1 Signaling. *The Journal of biological chemistry* 283, 18066-18075
25. Yokoyama, K., Erickson, H. P., Ikeda, Y, and Takada, Y (2000) Identification of amino acid sequences in fibrinogen gamma-chain and tenascin C C-terminal domains critical for binding to integrin alpha vbeta 3. *The Journal of biological chemistry* 275, 16891-16898
26. Nevalainen, T. J., Aho, H. J., and Peuravuori, H. (1994) Secretion of group 2 phospholipase A2 by lacrimal glands. *Investigative ophthalmology & visual science* 35, 417-421
27. Qu, X. D., and Lehrer, R. I. (1998) Secretory phospholipase A2 is the principal bactericide for staphylococci and other gram-positive bacteria in human tears. *Infection and immunity* 66, 2791-2797
28. Birts, C. N., Barton, C. H., and Wilton, D. C. (2010) Catalytic and non-catalytic functions of human IIA phospholipase A2. *Trends Biochem Sci* 35, 28-35
29. Saari, K. M., Aho, V., Paavilainen, V., and Nevalainen, T. J. (2001) Group II PLA(2) content of tears in normal subjects. *Investigative ophthalmology & visual science* 42, 318-320
30. Aho, H. J., Saari, K. M., Kallajoki, M., and Nevalainen, T. J. (1996) Synthesis of group II phospholipase A2 and lysozyme in lacrimal glands. *Investigative ophthalmology & visual science* 37, 1826-1832
31. Yamaji, S., Saegusa, J., Ieguchi, K., Fujita, M., Takada, Y K., and Takada, Y (2010) A novel fibroblast growth factor-1 (FGF1) mutant that acts as an FGF antagonist. *PLoS One* 5, e10273
32. Mori, S., and Takada, Y (2013) Crosstalk between Fibroblast Growth Factor (FGF) Receptor and Integrin through Direct Integrin Binding to FGF and Resulting Integrin-FGF-FGFR Ternary Complex Formation. *Medical Sciences* 1, 20-36
33. Mori, S., Tran, V., Nishikawa, K., Kaneda, T., Hamada, Y, Kawaguchi, N., Fujita, M., Takada, Y K., Matsuura, N., Zhao, M., and Takada, Y (2013) A Dominant-Negative 34. Saegusa, J., Yamaji, S., Ieguchi, K., Wu, C. Y, Lam, K. S., Liu, F. T., Takada, Y K., and Takada, Y (2009) The direct binding of insulin-like growth factor-1 (IGF-1) to integrin alphavbeta3 is involved in IGF-1 signaling. *The Journal of biological chemistry* 284, 24106-24114
35. Fujita, M., Ieguchi, K., Davari, P., Yamaji, S., Taniguchi, Y, Sekiguchi, K., Takada, Y K., and Takada, Y (2012) Cross-talk between integrin alpha6beta4 and insulin-like growth factor-1 receptor (IGF1R) through direct alpha6beta4 binding to IGF1 and subsequent alpha6beta4-IGF1-IGF1R ternary complex formation in anchorage-independent conditions. *The Journal of biological chemistry* 287, 12491-12500
36. Fujita, M., Ieguchi, K., Cedano-Prieto, D. M., Fong, A., Wilkerson, C., Chen, J. Q., Wu, M., Lo, S. H., Cheung, A. T., Wilson, M. D., Cardiff, R. D., Borowsky, A. D., Takada, Y K., and Takada, Y (2013) An Integrin Binding-defective Mutant of Insulin-like Growth Factor-1 (R36E/R37E IGF1) Acts as a Dominant-negative Antagonist of the IGF1 Receptor (IGF1R) and Suppresses Tumorigenesis but Still Binds to IGF1R. *The Journal of biological chemistry* 288, 19593-19603
37. Fujita, M., Takada, Y K., and Takada, Y (2013) Insulin-like Growth Factor (IGF) Signaling Requires alphavbeta3-IGF1-IGF Type 1 Receptor (IGF1R) Ternary Complex Formation in Anchorage Independence, and the Complex Formation Does Not Require IGF1R and Src Activation. *The Journal of biological chemistry* 288, 3059-3069
38. Ieguchi, K., Fujita, M., Ma, Z., Davari, P., Taniguchi, Y, Sekiguchi, K., Wang, B., Takada, Y K., and Takada, Y (2010) Direct binding of the EGF-like domain of neuregulin-1 to integrins ({alpha}v{beta}3 and {alpha}6{beta}4) is involved in neuregulin-1/ErbB signaling. *The Journal of biological chemistry* 285, 31388-31398
39. Xiong, J. P., Stehle, T., Zhang, R., Joachimiak, A., Frech, M., Goodman, S. L., and Arnaout, M. A. (2002) Crystal structure of the extracellular segment of integrin alpha Vbeta3 in complex with an Arg-Gly-Asp ligand. *Science* 296, 151-155.
40. Xiao, T., Takagi, J., Coller, B. S., Wang, J. H., and Springer, T. A. (2004) Structural basis for allostery in integrins and binding to fibrinogen-mimetic therapeutics. *Nature* 432, 59-67
41. Du, X. P., Plow, E. F., Frelinger, A. L., 3rd, O'Toole, T. E., Loftus, J. C., and Ginsberg, M. H. (1991) Ligands "activate" integrin alpha IIb beta 3 (platelet GPIIb-IIIa). *Cell* 65, 409-416
42. Legler, D. F., Wiedle, G, Ross, F. P., and Imhof, B. A. (2001) Superactivation of integrin alphavbeta3 by low antagonist concentrations. *J Cell Sci* 114, 1545-1553
43. Hu, D. D., White, C. A., Panzer-Knodle, S., Page, J. D., Nicholson, N., and Smith, J. W. (1999) A new model of dual interacting ligand binding sites on integrin alphaIIbbeta3. *The Journal of biological chemistry* 274, 4633-4639
44. Cierniewski, C. S., Byzova, T., Papierak, M., Haas, T. A., Niewiarowska, J., Zhang, L., Cieslak, M., and Plow, E. F. (1999) Peptide ligands can bind to distinct sites in integrin alphaIIbbeta3 and elicit different functional responses. *The Journal of biological chemistry* 274, 16923-16932
45. Luo, B. H., Carman, C. V., and Springer, T. A. (2007) Structural Basis of Integrin Regulation and Signaling. *Annu Rev Immunol* 25, 619-647
46. Luque, A., Gomez, M., Puzon, W., Takada, Y, Sanchez-Madrid, F., and Cabanas, C. (1996) Activated conformations of very late activation integrins detected by a group of antibodies (HUTS) specific for a novel regulatory region (355-425) of the common beta 1 chain. *The Journal of biological chemistry* 271, 11067-11075
47. Mould, A. P., Barton, S. J., Askari, J. A., McEwan, P. A., Buckley, P. A., Craig, S. E., and Humphries, M. J. (2003) Conformational changes in the integrin beta A domain provide a mechanism for signal transduction via hybrid domain movement. *The Journal of biological chemistry* 278, 17028-17035
48. Xiong, J. P., Stehle, T., Diefenbach, B., Zhang, R., Dunker, R., Scott, D. L., Joachimiak, A., Goodman, S. L., and Amaout, M. A. (2001) Crystal structure of the extracellular segment of integrin alpha Vbeta3. *Science* 294, 339-345
49. Bradley, J. D., Dmitrienko, A. A., Kivitz, A. J., Gluck, O. S., Weaver, A. L., Wiesenhutter, C., Myers, S. L., and Sides, G D. (2005) A randomized, double-blinded, placebo-controlled clinical trial of LY333013, a selective inhibitor of group II secretory phospholipase A2, in the treatment of rheumatoid arthritis. *J Rheumatol* 32, 417-423
50. Bowton, D. L., Dmitrienko, A. A., Israel, E., Zeiher, B. G, and Sides, G D. (2005) Impact of a soluble phospholipase A2 inhibitor on inhaled allergen challenge in subjects with asthma. *J Asthma* 42, 65-71

What is claimed is:

1. A composition comprising (1) an effective amount of an inhibitor for sPLA2-IIA and integrin binding and (2) a pharmaceutically acceptable carrier, wherein the inhibitor is a circular peptide consisting of the amino acid sequence set forth in SEQ ID NO:1, 2, 3, or 4.

2. The composition of claim 1, wherein the inhibitor is a circular peptide consisting of the amino acid sequence set forth in SEQ ID NO:1.

3. The composition of claim 1, wherein the inhibitor is a cyclic peptide consisting of the amino acid sequence set forth in SEQ ID NO:3.

4. The composition of claim 1, further comprising an additional therapeutic compound.

5. A method for inhibiting inflammation or suppressing cell proliferation, comprising the step of administering to a subject the composition of claim 1.

6. The method of claim 5, wherein the inhibitor is a circular peptide consisting of the amino acid sequence set forth in SEQ ID NO:1.

7. The method of claim 5, wherein the inhibitor is a circular peptide consisting of the amino acid sequence set forth in SEQ ID NO:3.

8. A method for identifying an inhibitor for integrin-sPLA2-IIA binding, comprising the steps of:

(a) contacting a test compound with sPLA2-IIA and a circular peptide consisting of the amino acid sequence set forth in SEQ ID NO:1, 2, 3, or 4, under conditions that permit specific binding between sPLA2-IIA and the circular peptide;

(b) determining the level of specific binding between sPLA2-IIA and the circular peptide, wherein a decrease in the level of specific binding compared to a control level of specific binding between sPLA2-IIA and the circular peptide under the same conditions but in the absence of the test compound indicates the compound as an inhibitor for integrin-sPLA2-IIA binding.

9. The method of claim 8, wherein sPLA2-IIA or the circular peptide is immobilized on a solid support.

10. The method of claim 8, wherein sPLA2-IIA is labelled with a fluorescent dye.

11. The method of claim 10, wherein the fluorescent dye is fluorescein isothiocyanate (FITC).

12. The method of claim 8, wherein the circular peptide consists of the amino acid sequence set forth in SEQ ID NO:1.

13. The method of claim 8, wherein the circular peptide consists of the amino acid sequence set forth in SEQ ID NO:3.

* * * * *